US011517369B2

(12) United States Patent
Jinno et al.

(10) Patent No.: US 11,517,369 B2
(45) Date of Patent: Dec. 6, 2022

(54) BLOOD VESSEL DISSECTING DEVICE

(71) Applicant: TERUMO KABUSHIKI KAISHA, Tokyo (JP)

(72) Inventors: Makoto Jinno, Kanagawa (JP); Tatsunori Fujii, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1019 days.

(21) Appl. No.: 15/652,568

(22) Filed: Jul. 18, 2017

(65) Prior Publication Data

US 2017/0312011 A1  Nov. 2, 2017

Related U.S. Application Data

(63) Continuation of application No. PCT/JP2015/071669, filed on Jul. 30, 2015.

(30) Foreign Application Priority Data

Jan. 19, 2015 (JP) .............................. JP2015-008184

(51) Int. Cl.
*A61B 17/00* (2006.01)
*A61B 18/14* (2006.01)
(Continued)

(52) U.S. Cl.
CPC ........ *A61B 18/14* (2013.01); *A61B 17/00008* (2013.01); *A61B 17/3205* (2013.01);
(Continued)

(58) Field of Classification Search
CPC ................ A61B 18/14; A61B 18/1492; A61B 17/00008; A61B 17/3205; A61B 17/3211;
(Continued)

(56) References Cited

U.S. PATENT DOCUMENTS 5,634,935 A * 6/1997 Taheri .............. A61B 17/00008
604/96.01
6,193,653 B1 * 2/2001 Evans .............. A61B 17/00008
600/210
(Continued)

FOREIGN PATENT DOCUMENTS

| JP | 2003-199765 A | 7/2003 |
| JP | 2005-246058 A | 9/2005 |
| WO | WO 2007/021010 A1 | 2/2007 |

OTHER PUBLICATIONS

International Search Report (PCT/ISA/210) dated Oct. 27, 2015, by the Japan Patent Office as the International Searching Authority for International Application No. PCT/JP2015/071669.
(Continued)

*Primary Examiner* — Joanne M Hoffman
*Assistant Examiner* — Rachel A. Vierra
(74) *Attorney, Agent, or Firm* — Buchanan Ingersoll & Rooney P.C.

(57) ABSTRACT

A blood vessel dissecting device is disclosed, which includes a dissecting device which, when being inserted into a living body along a blood vessel, dissects tissue in a direction of alignment thereof with the blood vessel, and a cutting device which, when being inserted into the living body along the blood vessel, cuts tissue surrounding the blood vessel in a direction of alignment thereof with the blood vessel. The cutting device includes a main body section which is inserted into the living body and holds the tissue between itself and the dissecting device, and a cutting section which cuts the tissue held between the main body section and the dissecting device.

20 Claims, 42 Drawing Sheets

(51) Int. Cl.
*A61B 17/32* (2006.01)
*A61B 17/3205* (2006.01)
*A61B 90/00* (2016.01)
*A61B 18/00* (2006.01)

(52) U.S. Cl.
CPC .. *A61B 17/320016* (2013.01); *A61B 18/1492* (2013.01); *A61B 90/361* (2016.02); *A61B 2017/00778* (2013.01); *A61B 2017/00969* (2013.01); *A61B 2018/00428* (2013.01); *A61B 2018/00589* (2013.01); *A61B 2018/00595* (2013.01); *A61B 2018/00601* (2013.01); *A61B 2018/00982* (2013.01); *A61B 2018/1467* (2013.01)

(58) Field of Classification Search
CPC ........ A61B 90/361; A61B 2017/00778; A61B 2017/00969; A61B 2018/00428; A61B 2018/00589; A61B 2018/00595; A61B 2018/00607; A61B 2018/00982; A61B 2018/1467; A61B 2018/1412; A61B 2017/320044; A61B 17/0008; A61B 17/320783; A61B 17/32075; A61B 2017/320016; A61B 2017/320036
See application file for complete search history.

(56) References Cited

U.S. PATENT DOCUMENTS

| | | | |
|---|---|---|---|
| 2002/0099375 A1* | 7/2002 | Hess | A61B 18/1445 606/51 |
| 2003/0130654 A1 | 7/2003 | Kasahara et al. | |
| 2004/0097921 A1 | 5/2004 | Hess et al. | |
| 2004/0186492 A1 | 9/2004 | Hess et al. | |
| 2005/0192613 A1 | 9/2005 | Lindsay | |
| 2006/0173474 A1 | 8/2006 | Wellman et al. | |
| 2006/0276815 A1 | 12/2006 | Lotti et al. | |
| 2008/0208193 A1 | 8/2008 | Yamatani et al. | |
| 2009/0024121 A1 | 1/2009 | Kasahara et al. | |
| 2011/0251613 A1* | 10/2011 | Guerra | A61B 18/1445 606/52 |

OTHER PUBLICATIONS

Written Opinion (PCT/ISA/237) dated Oct. 27, 2015, by the Japan Patent Office as the International Searching Authority for International Application No. PCT/JP2015/071669.

* cited by examiner

BLOOD VESSEL DISSECTING DEVICE

CROSS-REFERENCES TO RELATED APPLICATIONS

This application is a continuation of International Application No. PCT/JP2015/071669 filed on Jul. 30, 2015, which claims priority to Japanese Application No. 2015-008184 filed on Jan. 19, 2015, the entire contents of which are incorporated herein by reference.

TECHNICAL FIELD

The present disclosure relates to a blood vessel dissecting device.

BACKGROUND DISCUSSION

It is known to use an artery graft represented by internal thoracic artery, gastroepiploic artery and radial artery or a vein graft represented by great saphenous vein as a bypass vessel in performing vascular bypass grafting at the heart (CABG: coronary artery bypass grafting). In addition, at present, it has been reported that artery grafts (particularly, internal thoracic artery) offer higher long-term patency rates than vein grafts. Thus, vein grafts are commonly said to be poor in long-term patency rate. In recent years, however, it has been reported that the long-term patency rate concerning a vein graft is enhanced when the vein graft is harvested in the state of being covered with surrounding tissue (for example, fat, connective tissue, tissue between a skin layer and a muscle layer, tissue between a skin layer and an interosseous membrane, branch vessels, etc.) and is used as a bypass vessel while remaining covered with the tissue. In addition, as a device by which a vein graft can be harvested in the state of being covered with the surrounding tissue, there is known a device disclosed in US 2006/0276815 (hereinafter referred to as Patent Document 1), for example.

In using the device disclosed in Patent Document 1, a guide wire (support member 50) is inserted into a blood vessel to be harvested as a bypass vessel, and a tubular member (portion 40) is pushed forward while guiding it with the guide wire, whereby the blood vessel can be harvested in the state of being covered with the surrounding tissue. The device disclosed in Patent Document 1, however, has drawbacks in that the guide wire may damage the internal wall of the blood vessel being harvested and that the workability in blood vessel harvesting (blood vessel dissection) can be poor.

SUMMARY

A blood vessel dissecting device is disclosed, by which a blood vessel can be dissected with good workability.

In an aspect, a blood vessel dissecting device is disclosed, which includes a dissecting device which, when being inserted into a living body along a blood vessel, dissects tissue in a direction of alignment thereof with the blood vessel, and a cutting device which, when being inserted into the living body along the blood vessel, cuts tissue surrounding the blood vessel in a direction of alignment thereof with the blood vessel. The cutting device includes a main body section, which is inserted into the living body and holds the tissue between itself and the dissecting device, and a cutting section which cuts the tissue held between the main body section and the dissecting device.

In the blood vessel dissecting device as above, preferably, the main body section has a guide section which guides the tissue to between the main body section and the dissecting device.

In the blood vessel dissecting device as above, preferably, the main body section has a groove opening to the dissecting device side, and the cutting section is movable in the groove.

In the blood vessel dissecting device as above, preferably, the tissue held between the main body section and the dissecting device includes a branch vessel branched from the blood vessel, and the cutting device cuts the branch vessel.

The blood vessel dissecting device as above may further include a first electrode and a second electrode which apply an electric field to the branch vessel.

In the blood vessel dissecting device as above, preferably, the first electrode and the second electrode are both provided in the cutting device.

In the blood vessel dissecting device as above, preferably, the cutting section functions also as the second electrode.

In the blood vessel dissecting device as above, preferably, the first electrode is provided in the cutting device, and the second electrode is provided in the dissecting device.

In another aspect, a blood vessel dissecting device is disclosed, which includes a dissecting device which, when being inserted into a living body along a blood vessel, dissects tissue in a direction of alignment thereof with the blood vessel; a cutting device which, when being inserted into the living body along the blood vessel, cuts tissue surrounding the blood vessel in a direction of alignment thereof with the blood vessel, wherein the cutting device includes a main body section which is inserted into the living body and holds the tissue between itself and the dissecting device, and a cutting section which cuts the tissue held between the main body section and the dissecting device; and a treating device configured to be inserted into a cavity section of the dissection device, the treating device includes a bar-shaped elongated operation section, an electrode provided at a proximal portion of the operation section, and a cutting section provided at a proximal portion of the electrode.

In a further aspect, a blood vessel dissecting method is disclosed, which includes inserting a dissecting device into a living body along a blood vessel, the dissecting device configured to dissect tissue in a direction of alignment thereof with the blood vessel; inserting a cutting device into the living body along the blood vessel, the cutting device configured to cut tissue surrounding the blood vessel in a direction of alignment thereof with the blood vessel, wherein the cutting device includes a main body section which is inserted into the living body and holds the tissue between itself and the dissecting device, and cutting the tissue being held between the main body section and the dissecting device with a cutting section of the cutting device.

According to the described aspect, the branch vessel held between the dissecting device and the main body section of the cutting device is cut. Therefore, displacement or the like of the branch vessel is restrained, and the branch vessel can be easily cut. For this reason, a blood vessel dissecting device excellent in workability in blood vessel dissection can be realized.

DETAILED DESCRIPTION OF THE PREFERRED EMBODIMENTS

A blood vessel dissecting device and a blood vessel dissecting method according to the described aspects of the present disclosure will be described in detail below, referring to preferred embodiments thereof illustrated in the attached drawings.

Figure 1:
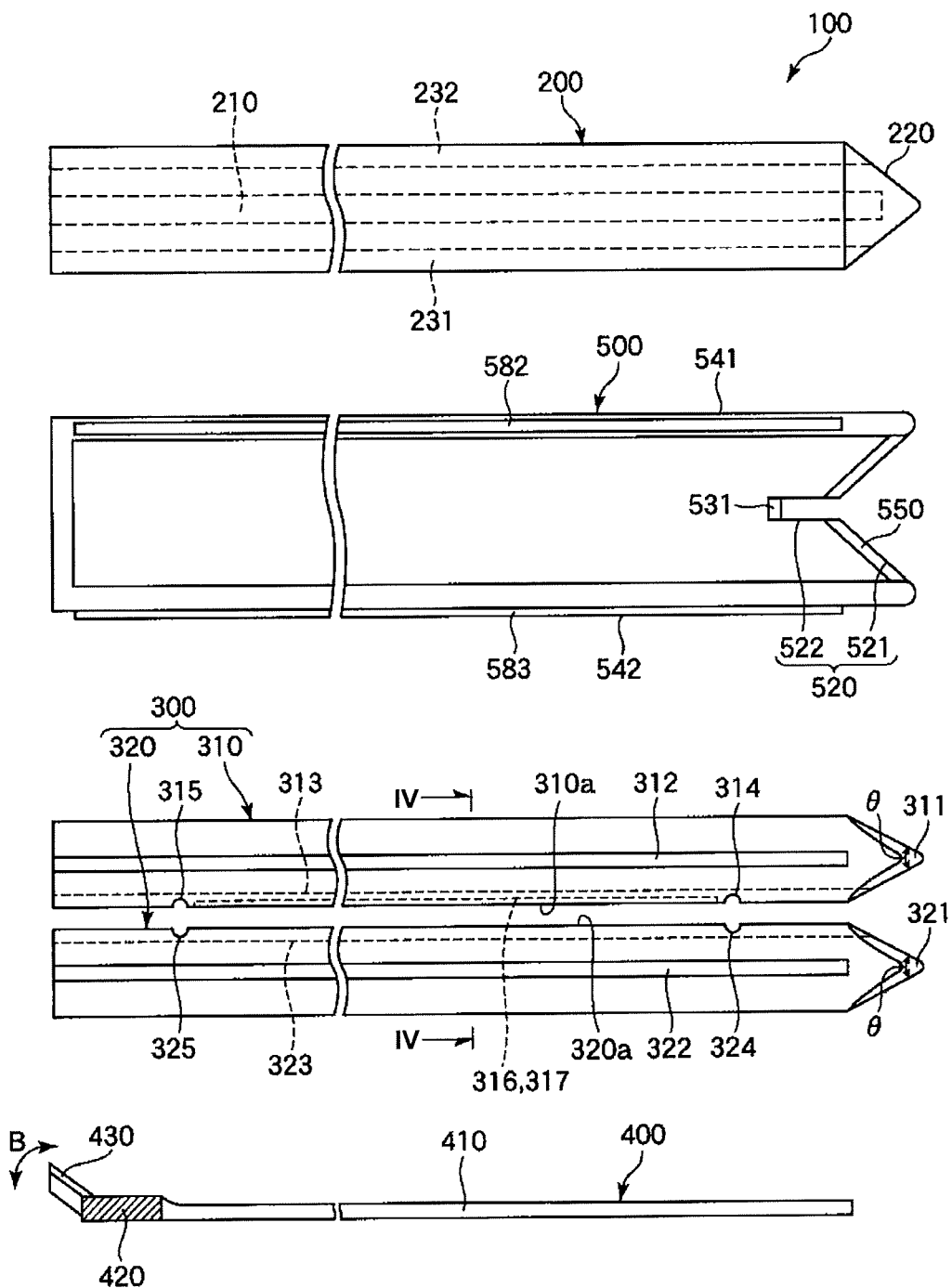
FIG. 1 is a plan view depicting constituent members of a blood vessel dissecting device according to a first embodiment of the present disclosure.
Figure 2:
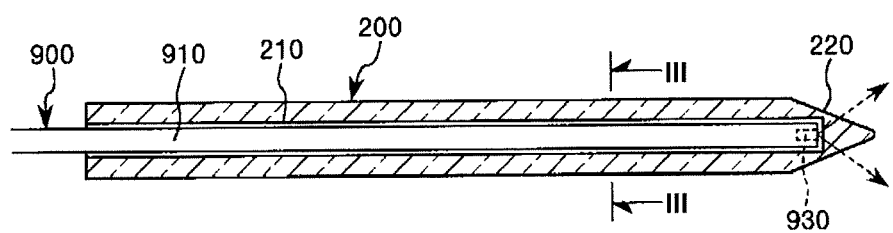
FIG. 2 is a sectional view depicting a skin-side dissecting device.
Figure 3:
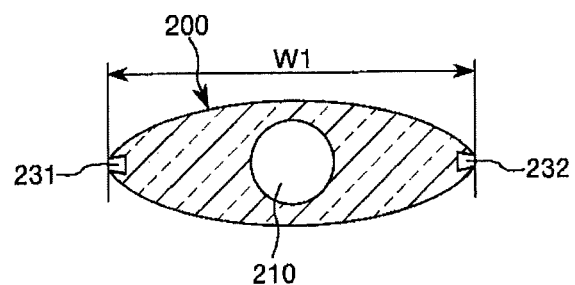
FIG. 3 is a sectional view taken along line III-III of FIG. 2.
Figure 4:
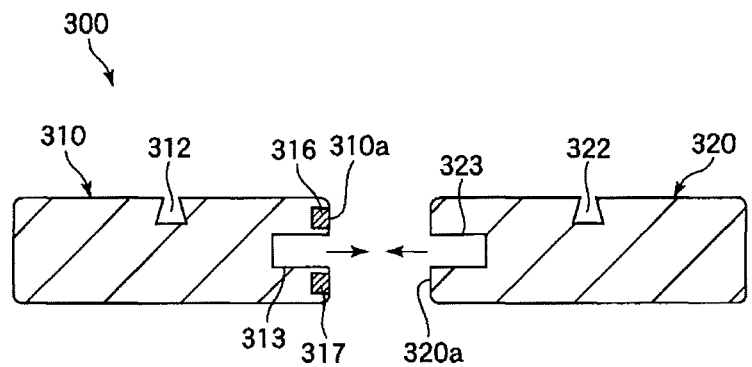
FIG. 4 is a sectional view taken along line IV-IV of FIG. 1.
Figure 5:
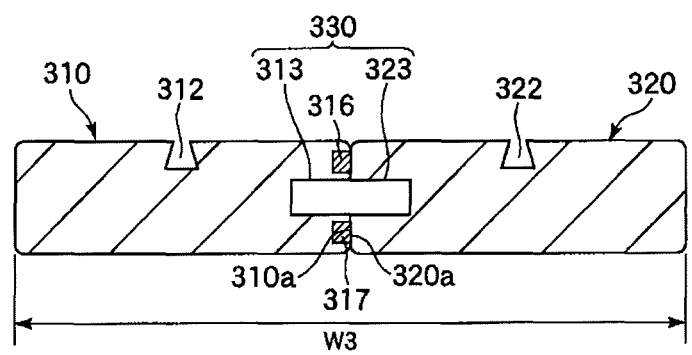
FIG. 5 is a sectional view depicting a state in which a first dissecting device and a second dissecting device depicted in FIG. 4 are abutted on each other.
Figure 6:
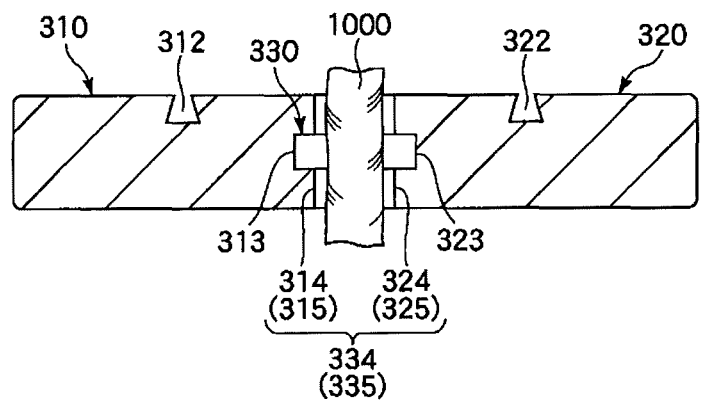
FIG. 6 is a sectional view depicting a state in which the first dissecting device and the second dissecting device depicted in FIG. 4 are abutted on each other.
Figure 7:
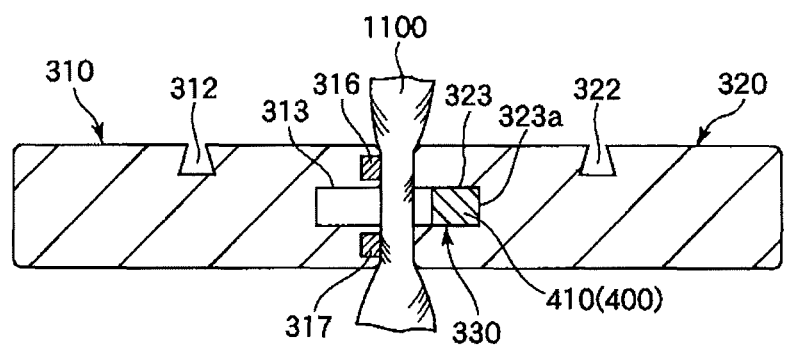
FIG. 7 is a sectional view depicting a treating device.
Figure 8:
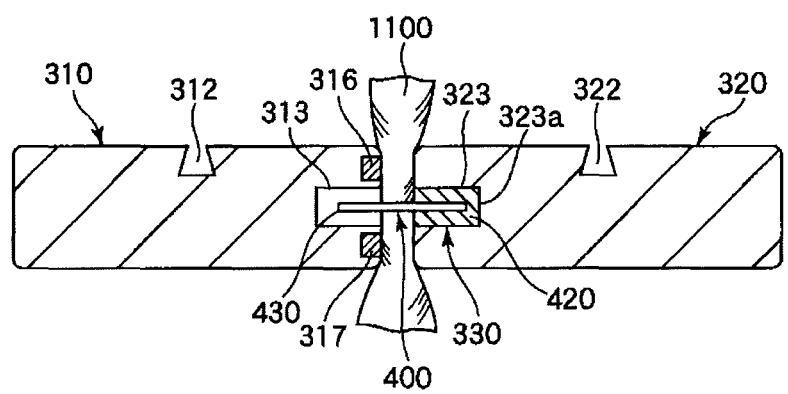
FIG. 8 is a sectional view depicting the treating device.
Figure 9:
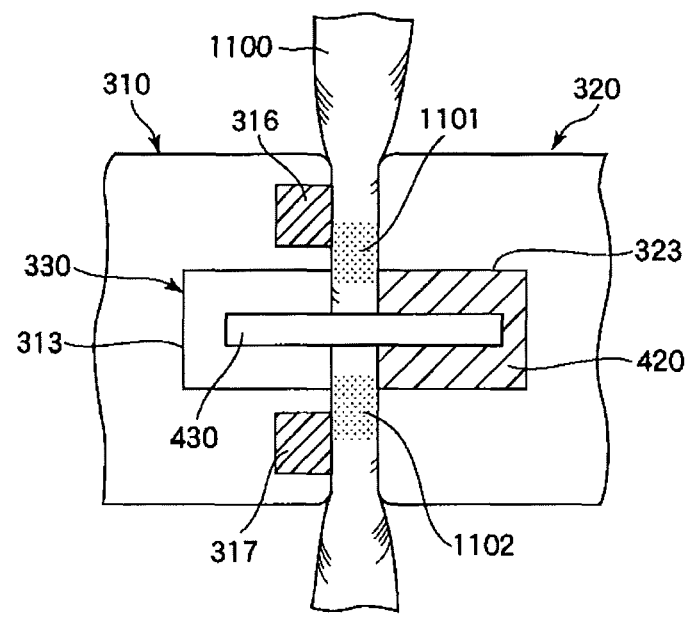
FIG. 9 is a sectional view illustrating a cutting position of a branch vessel in cutting by the treating device.
Figure 10:
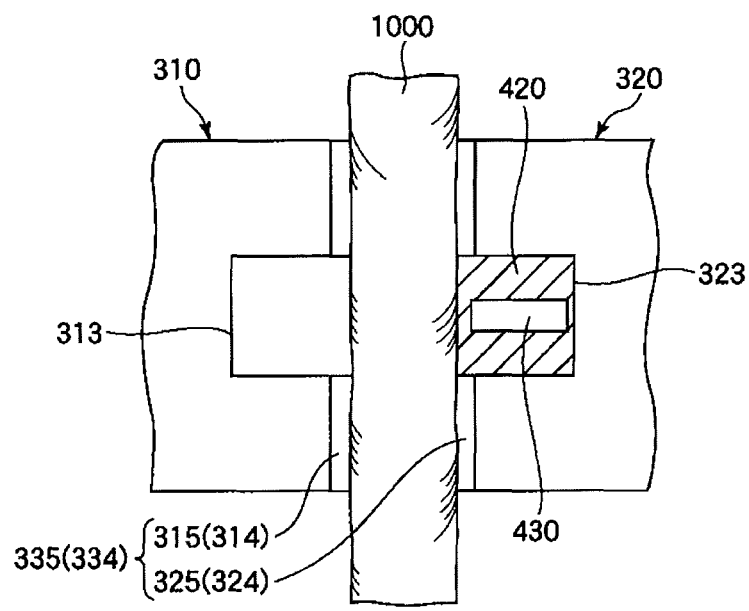
FIG. 10 is a sectional view depicting displacement of a cutting section possessed by the treating device.
Figure 11:
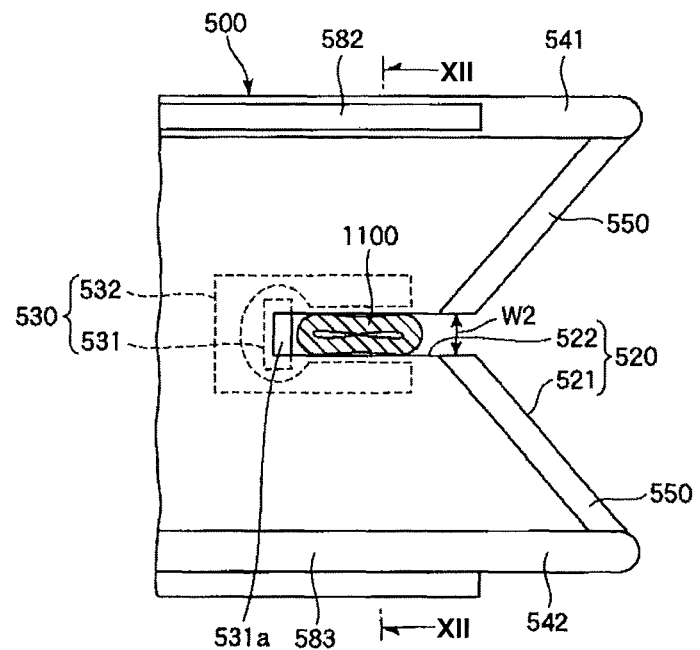
FIG. 11 is a lateral view of a cutting device.
Figure 12:
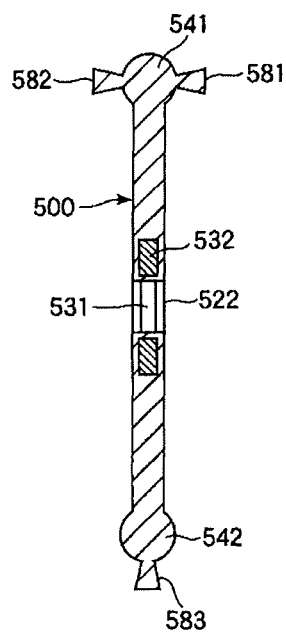
FIG. 12 is a sectional view taken along line XII-XII of FIG. 11.

FIG. 1 is a plan view depicting constituent members of a blood vessel dissecting device according to a first embodiment of the present disclosure. FIG. 2 is a sectional view depicting a skin-side dissecting device. FIG. 3 is a sectional view taken along line III-III of FIG. 2. FIG. 4 is a sectional view taken along line IV-IV of FIG. 1. FIGS. 5 and 6 are sectional views depicting a state in which a first dissecting device and a second dissecting device depicted in FIG. 4 are abutted on each other. FIGS. 7 and 8 are sectional views depicting a treating device. FIG. 9 is a sectional view illustrating a cutting position of a branch vessel in cutting by the treating device. FIG. 10 is a sectional view depicting displacement of a cutting section possessed by the treating device. FIG. 11 is a lateral view of a cutting device. FIG. 12 is a sectional view taken along line XII-XII of FIG. 11. FIGS. 13 to 19 illustrate a blood vessel dissecting method. Note that in the following, for convenience of explanation, the right side in FIG. 1 will be referred to as "distal" side, and the left side as "proximal" side.

Blood Vessel Dissecting Device

A blood vessel dissecting device 100 depicted in FIG. 1 is a device, which can be used for harvesting a blood vessel for use as a bypass vessel in blood vessel bypass grafting (particularly, CABG: coronary artery bypass grafting). By use of the blood vessel dissecting device 100, a blood vessel can be harvested in the state of being covered with surrounding tissue (fat, connective tissue, etc.). Note that the blood vessel to be harvested by use of the blood vessel dissecting device 100 is not particularly limited so long as it is a blood vessel that can be used as a bypass vessel. Examples of the applicable blood vessel include internal thoracic artery, gastroepiploic artery, radial artery, and great saphenous vein.

Among others, the great saphenous vein is preferred as the blood vessel to be harvested. Since the use of the blood vessel dissecting device 100 facilitates harvesting of a blood vessel in the state of being covered with surrounding tissue as aforementioned, when a great saphenous vein is harvested by use of the blood vessel dissecting device 100 and used as a bypass vessel, it is considered that long-term patency rate after the operation will be relatively high. Therefore, in the following, an example of harvesting a great saphenous vein by use of the blood vessel dissecting device 100 will be described on a representative basis.

As illustrated in FIG. 1, the blood vessel dissecting device 100 can include a skin-side dissecting device 200, a fascia-side dissecting device 300, a treating device 400, and a cutting device 500. Of these devices, the skin-side dissecting device 200, the fascia-side dissecting device 300, and the cutting device 500 are devices, which are inserted into a living body along a great saphenous vein, and the treating device 400 is a device, which is inserted into the fascia-side dissecting device 300. These devices will be sequentially described below.

Skin-Side Dissecting Device

As depicted in FIG. 2, the skin-side dissecting device 200 has an elongated bar-like shape extending substantially straight, and is provided at its distal portion with a dissecting section 220 for dissecting tissue. In addition, as depicted in FIG. 3, the skin-side dissecting device 200 has a flat shape (vertically flattened shape) in section. The sectional shape of the skin-side dissecting device 200 is not particularly limited; for example, it may be a crushed-circle-like shape, such as an oblong and an ellipse, or a rectangle rounded at corners.

In addition, the width (the length in the major axis direction of the cross section) W1 of the skin-side dissecting device 200 is greater than the outside diameter of the blood vessel to be harvested (in this embodiment, the great saphenous vein). Specifically, for example, the width W1 is preferably greater than the outside diameter of the blood vessel to be harvested by approximately 4 mm to 4 cm, which helps ensure that when inserting the cutting device 500 into a living body along the skin-side dissecting device 200, the possibility of contact between the cutting device 500 and the great saphenous vein can be effectively reduced, as will be explained in the "blood vessel harvesting method" described later.

In addition, the skin-side dissecting device 200 can be provided, at both ends of the major axis direction of the sectional shape thereof, with rails 231 and 232 in the form of linear stretches of recess (or trenches) which extend in the axial direction of the skin-side dissecting device 200. In accordance with an exemplary embodiment, these rails 231 and 232 are rails for use in connecting the cutting device 500 to the skin-side dissecting device 200. Note that the configuration of the rails 231 and 232 is not particularly limited so long as connection with the cutting device 500 is enabled thereby.

In addition, as depicted in FIG. 2, the skin-side dissecting device 200 is provided with an insertion hole 210 opening at the proximal end and extending to a distal portion (the dissecting section 220). Into the insertion hole 210 is inserted an imaging device 900. The imaging device 900 is not particularly limited. For instance, the imaging device 900 in this embodiment has an elongated main body section 910, and is provided, at a distal portion of the main body section 910, with an illuminating section (not depicted) for emitting illumination light and an imaging section 930 for imaging the front side of the skin-side dissecting device 200. The imaging section 930 can include, for example, an objective lens system provided at a distal portion of the main body section 910, and an imaging element (for example, solid state imaging element such as complementary metal oxide semiconductor (CMOS) image sensor or charge-coupled device (CCD) sensor) disposed opposite to the objective lens system.

In addition, the dissecting section 220 can be tapered off toward the distal end of the skin-side dissecting device 200. More specifically, the dissecting section 220 is in a tapered roughly conical shape such that the length in the minor axis direction and the length in the major axis direction of the cross sectional shape of the dissecting section 220 are both gradually decreased towards the distal side. In accordance with an exemplary embodiment, such a dissecting section 220 is blunt in the thickness direction, and has such a degree of sharpness (bluntness) as to be able to dissect tissues having different properties (for example, fat and skin, fat and fascia, fat and blood vessel, fat and bone) from each other without cutting branch vessels branched from a great saphenous vein, which helps ensure that the dissecting section 220 can sufficiently exhibit a dissecting function, and damaging or cutting of the branch vessel by the dissecting section 220 is restrained. Therefore, bleeding can be suppressed, and the intended procedure can be performed relatively safely and smoothly. Note that the shape of the dissecting section 220 is not particularly limited so long as the dissecting section 220 can dissect tissue in the thickness direction (minor axis direction) thereof. For example, the dissecting section 220 may be tapered in a duckbill shape such that the length in the minor axis direction of the cross-sectional shape of the dissecting section 220 gradually decreases toward the distal side and that its distal end is a linear shape along the major axis direction.

In addition, in accordance with an exemplary embodiment, the dissecting section 220 is substantially colorless and transparent and is light-transmitting. Therefore, with the imaging device 900 inserted in the aforementioned insertion hole 210, the front side of the skin-side dissecting device 200 can be observed through the dissecting section 220 by the imaging device 900. For this reason, the dissecting section 220 has a function as an observing section for observation of the inside of a living body, in addition to the aforementioned dissecting function. Note that the dissecting section 220 is not limited to a colorless and transparent state so long as it is light-transmitting; for example, the dissecting section 220 may be colored in red, blue, green or the like.

Fascia-Side Dissecting Device

As depicted in FIG. 1, the fascia-side dissecting device 300 can include a first dissecting device (insertion device) 310 and a second dissecting device (insertion device) 320. As will be described later, the first dissecting device 310 and the second dissecting device 320 are used by being disposed in a living body in such a manner that their side surfaces are abutted on each other. Note that in this embodiment the first dissecting device 310 and the second dissecting device 320 are the same in configuration, except that electrodes are disposed in the first dissecting device 310.

The first dissecting device 310 has an elongated bar-like shape extending substantially straight, and is provided at its distal portion with a dissecting section 311 for dissecting tissue. Similarly, the second dissecting device 320 also has an elongated bar-like shape extending substantially straight, and is provided at its distal portion with a dissecting section 321 for dissecting tissue. The dissecting sections 311 and 321 can be tapered off toward the distal ends thereof. More specifically, the dissecting sections 311 and 321 are each tapered in such a manner that the length in the minor direction and the length in the major axis direction of the cross-sectional shape thereof are both gradually decreasing towards the distal side. Such dissecting sections 311 and 321 are blunt in the thickness direction thereof, and have such a degree of sharpness (bluntness) as to be able to dissect tissues having different properties (for example, fat and skin, fat and fascia, fat and blood vessel, fat and bone, and so on) from each other without cutting branch vessels branched from a great saphenous vein, which helps ensure that the dissecting sections 311 and 321 can sufficiently exhibit a dissecting function and that damaging or cutting of branch vessels by the dissecting sections 311 or 321 is restrained. Therefore, bleeding can be suppressed, and the intended procedure can be performed relatively safely and smoothly. Note that the taper angles θ of the dissecting sections 311 and 321 in plan view are not particularly limited, and may be approximately 50° to 70°. In addition, the shapes of the dissecting sections 311 and 321 are not particularly limited so long as the dissecting sections 311 and 321 can dissect tissue in the thickness direction thereof; for example, a duck bill shape may be adopted.

In addition, the first dissecting device 310 and the second dissecting device 320 each have a flat shape (vertically flattened shape), as depicted in FIG. 4. Note that in this embodiment, sectional shapes of the first dissecting device 310 and the second dissecting device 320 are each a rectangle rounded at corners. It is to be noted, however, that the sectional shapes of the first dissecting device 310 and the second dissecting device 320 are not particularly limited, and examples of each of the sectional shapes may include not only the rectangle but also a crushed-circle-like shape, such as an oblong and an ellipse.

In addition, an upper surface (a main surface on one side) of the first dissecting device 310 is provided with a rail 312 in the form of a linear stretch of recess (or trench) extending in the axial direction. Similarly, an upper surface of the second dissecting device 320 is also provided with a rail 322 in the form of a linear stretch of recess (or trench) extending in the axial direction. These rails 312 and 322 are rails for use in connecting the dissecting devices to the cutting device 500. Note that the configuration of the rails 312 and 322 is not particularly limited, so long as connection with the cutting device 500 is enabled thereby.

The first dissecting device 310 and the second dissecting device 320 are used in such a manner that their side surfaces are abutted on each other. As illustrated in FIG. 4, the first dissecting device 310 is provided with a groove (second groove) 313 opening in a butt surface (a side surface on the second dissecting device 320 side) 310a thereof. In accordance with an exemplary embodiment, the groove 313 extends in the axial direction of the first dissecting device 310, and is open at both the distal end and the proximal end of the first dissecting device 310. Similarly, the second dissecting device 320 is provided with a groove (first groove) 323 opening in a butt surface (a side surface on the first dissecting device 310 side) 320a thereof. The groove 323 extends in the axial direction of the second dissecting device 320, and is open at both the distal end and the proximal end of the second dissecting device 320. The grooves 313 and 323 communicate with each other and form a cavity section 330 when the butt surfaces 310a and 320a are abutted on each other, as illustrated in FIG. 5. The cavity section 330 functions as an insertion section into which the treating device 400 is inserted. Such a configuration can enable the treating device 400 to be moved inside the first and second dissecting devices 310 and 320, so that a treatment by the treating device 400 can be performed relatively smoothly and accurately.

Note that the overall width W3 when the first dissecting device 310 and the second dissecting device 320 are abutted on each other is greater than the outside diameter of a blood vessel to be harvested. Specifically, for example, the first dissecting device 310 and the second dissecting device 320 each preferably have a width of approximately 20 mm to 40 mm.

In addition, as depicted in FIG. 1, the first dissecting device 310 has cutouts 314 and 315 opening in the butt surface 310a. The cutouts 314 and 315 are disposed respectively on the distal side and the proximal side of the first dissecting device 310, with a spacing therebetween. Similarly, the second dissecting device 320 has cutouts 324 and 325 opening in the butt surface 320a. The cutouts 324 and 325 are disposed respectively on the distal side and the proximal side of the second dissecting device 320, with a spacing therebetween. When the first dissecting device 310 and the second dissecting device 320 are abutted on each other, as depicted in FIG. 6, the cutouts 314 and 324 are connected together, to thereby form a through-hole 334, which penetrates the first and second dissecting devices 310 and 320 in the vertical direction. Similarly, the cutouts 315 and 325 are connected together, to thereby form a through-hole 335, which penetrates the first and second dissecting devices 310 and 320 in the vertical direction. These through-holes 334 and 335 function as inserting and passing sections in and through which a great saphenous vein 1000 is inserted and passed when the first dissecting device 310 and the second dissecting device 320 are abutted on each other, which helps prevent the great saphenous vein 1000 from being clamped between the first dissecting device 310 and the second dissecting device 320, so that it is possible to prevent damaging or cutting of the great saphenous vein 1000, a lowering in blood flow, or the like trouble. Note that while both the first dissecting device 310 and the second dissecting device 320 are provided with the cutouts in this embodiment, a configuration may be adopted wherein only one of the first dissecting device 310 and the second dissecting device 320 is provided with the cutouts.

In addition, on the butt surface 310a side of the first dissecting device 310, a pair of electrodes 316 and 317 can be provided. In accordance with an exemplary embodiment, the electrodes 316 and 317 extend in the axial direction between the cutouts 314 and 315, and are disposed opposite to each other, with the groove 313 therebetween. In addition, the electrodes 316 and 317 are connected to be the same in potential. These electrodes 316 and 317 are electrodes for generating an electric field for cauterization of the branch vessel 1100, as will be described later. Note that while the electrodes 316 and 317 are exposed at the butt surface 310a in this embodiment, a configuration may be adopted wherein the electrodes 316 and 317 are not exposed at the butt surface 310a but implanted in the first dissecting device 310.

While the first and second dissecting devices 310 and 320 have been described above, the first and second dissecting devices 310 and 320 may be provided with an insertion hole in which to insert the imaging device 900, like the aforementioned skin-side dissecting device 200, which helps ensure that the insertion of the first dissecting device 310 and the second dissecting device 320 into a living body can be carried out smoothly.

In addition, while the fascia-side dissecting device 300 is configured to have the two dissecting devices in this embodiment, the number of the dissecting devices is not particularly limited so long as the number is two or more.

Treating Device

As illustrated in FIG. 1, the treating device 400 can include a bar-shaped elongated operation section 410, an electrode 420 provided at a proximal portion of the operation section 410, and a cutting section 430 provided at a proximal portion of the electrode 420.

The operation section 410 can be inserted into the cavity section 330 of the fascia-side dissecting device 300. In addition, in the cavity section 330, the operation section 410 can be slid in the groove 323 without protruding to the side of the groove 313 of the first dissecting device 310. As will be described later, the branch vessel 1100 is held between the first dissecting device 310 and the second dissecting device 320, and, therefore, the branch vessel 1100 is located between the grooves 313 and 323, as depicted in FIG. 7. For this reason, with the operation section 410 slid in the groove 323, the contact between the operation section 410 and the branch vessel 1100 can be restrained, and the treating device 400 can be operated smoothly. In addition, the possibility of damaging or cutting the branch vessel 1100 can be reduced.

In addition, in a state where the operation section 410 is inserted in the groove 323, as depicted in FIG. 8, the electrode 420 is disposed opposite to the electrodes 316 and 317, with the branch vessel 1100 therebetween. In addition, the electrode 420 is disposed such as to make contact with the branch vessel 1100. Therefore, when a high-frequency alternating voltage is impressed between the electrode 420 and the electrodes 316 and 317, an electric field generated therebetween acts on the branch vessel 1100, whereby the branch vessel 1100 can be cauterized and thermal coagulation (stanching) can be achieved.

In addition, in a state where the operation section 410 is inserted in the groove 323, the cutting section 430 is disposed across a boundary between the groove 313 and the groove 323. Therefore, the part between the electrode 420 and the electrodes 316 and 317 has a bipolar structure. Accordingly, in accordance with an exemplary embodiment, when the operation section 410 is slid toward the distal side while impressing the high-frequency alternating voltage, the branch vessels 1100 held between the first and second dissecting devices 310 and 320 can be sequentially thermally coagulated, and, further, the thermally coagulated branch vessels 1100 can be cut by the cutting section 430. Here, a bottom surface (a surface opposed to the opening) of the groove 323 constitutes a guide surface (sliding surface) 323a for guiding the operation section 410. With the operation section 410 slid on the guide surface 323a, the operation section 410 can be prevented from protruding excessively to the groove 313 side, and the cutting section 430 can be maintained in the state of being situated across the boundary between the grooves 313 and 323. For this reason, the aforesaid operation can be carried out relatively smoothly and accurately. Note that the guide surface 323a may be subjected, for example, to a coating treatment (a treatment for imparting hydrophilicity, or the like) such as to reduce frictional resistance and enhance slidability.

A part cut by the cutting section 430 will now be described specifically. As depicted in FIG. 9, in accordance with an exemplary embodiment, the branch vessel 1100 is thermally coagulated at a part (a part flattened by being clamped between the butt surfaces 310a and 320a) 1101 between the electrode 420 and the electrode 316 and at a part (a part flattened by being clamped between the butt surfaces 310a and 320a) 1102 between the electrode 420 and the electrode 317, and is cut between these parts 1101 and 1102 by the cutting section 430. Therefore, bleeding from the branch vessel 1100 after the cutting can be prevented. According to such a treating device 400 as this, the branch vessel 1100 held between the first dissecting device 310 and the second dissecting device 320 can be easily stanched and cut.

Note that electrodes may be disposed also on the second dissecting device 320 side. With electrodes disposed also on the second dissecting device 320 side in such a manner as to be opposed to the electrodes 316 and 317, the electrodes can be brought into contact with a pressed part of the branch vessel 1100 from both sides of the pressed part, so that efficient thermal coagulation can be performed when a current is passed. In addition, when the cutting section 430 is also provided with the same electrode function as that of the electrode 420, cutting in a current-passing state can be performed.

In addition, in accordance with an exemplary embodiment, the cutting section 430 is preferably configured in such a manner that, for example, it can be rotated as indicated by arrows B in FIG. 1, whereby it can be switched between a state of coming across the boundary between the grooves 313 and 323 to enter into the groove 313 as depicted in FIG. 9 and a state of not entering into the groove 313 but being retracted into the groove 323 as depicted in FIG. 10, which helps ensure that, by setting the cutting section 430 in the retracted state when inserting the treating device 400 into the cavity section 330, cutting of the great saphenous vein 1000 (the part inserted in and passed through the through-holes 334 and 335) by the cutting section 430 can be prevented. Note that in the following, for convenience of explanation, the state depicted in FIG. 9 will be referred to also as "operating state" and the state depicted in FIG. 10 will be referred to also as "retracted state."

Cutting Device

The cutting device 500, at the time of moving along a great saphenous vein 1000, cuts fat (inclusive of connective tissue) surrounding the great saphenous vein 1000 and cuts and stanches the branch vessels branched from the great saphenous vein 1000.

In accordance with an exemplary embodiment, the cutting device 500 is elongated plate-like in shape. In addition, the cutting device 500 has a groove 520 opening in a distal portion thereof, as depicted in FIG. 1. The groove 520 can include a tapered blood vessel guide groove 521 having a width gradually decreasing toward the proximal side, and a blood vessel treating groove 522, which is located on the proximal side of the blood vessel guide groove 521 and is substantially constant in width. The blood vessel guide groove 521 is a groove for guiding the branch vessel 1100 into the blood vessel treating groove 522 when the cutting device 500 is pushed forward within a living body, and the blood vessel guide groove 521 is tapered for the purpose of performing the guiding smoothly. On the other hand, the blood vessel treating groove 522 is a groove for cutting and stanching the branch vessel 1100 guided by the blood vessel guiding groove 521. The blood vessel treating groove 522 is provided with a treating section 530 for cutting and stanching the branch vessel 1100.

As depicted in FIG. 11, the treating section 530 is of a bipolar structure including a pair of electrodes 531 and 532 for generating an electric field inside the blood vessel treating groove 522. The electrode 531 is provided at a proximal portion of the blood vessel treating groove 522, whereas the electrode 532 is provided on both sides of the blood vessel treating groove 522. With a high-frequency alternating voltage impressed between the electrodes 531 and 532 as above, the branch vessel 1100 guided into the blood vessel treating groove 522 can be cauterized, thereby stanching through thermal coagulation, and to cut the branch vessel 1100. Note that a distal portion 531a of the electrode 531 is preferably sharp to such an extent as to be able to cut the branch vessel 1100. This configuration helps ensure that if at least the branch vessel 1100 can be thermally coagulated by the electric field, the branch vessel 1100 can be physically cut by the distal portion 531a of the electrode 531. Accordingly, the assuredness of the treatment by the treating section 530 can be enhanced.

Note that the width W2 of the blood vessel treating groove 522 is not particularly limited, but it is preferably smaller than the outside diameter of the branch vessel 1100, which configuration helps ensure that the branch vessel 1100 can be pressed flat inside the blood vessel treating groove 522, as depicted in FIG. 11, so that the treatment (particularly, stanching) at the treating section 530 can be reliably performed.

In addition, the cutting device 500 has a cutting edge section 550 for cutting fat surrounding the great saphenous vein 1000. The cutting edge section 550 is provided at a distal portion of the cutting device 500, and is provided along the blood vessel guide groove 521 in this embodiment. The cutting edge section 550 preferably has such a degree of sharpness as to be able to cut the fat without cutting the branch vessel 1100. With this configuration, cutting of the branch vessel 1100 by the cutting edge section 550 is restrained, so that bleeding can be suppressed, and the intended procedure can be performed relatively safely and smoothly.

In addition, as depicted in FIG. 12, the cutting device 500 has a pair of protection sections 541 and 542 provided on both sides of the cutting device 500. The protection sections 541 and 542 extend along the axial direction of the cutting device 500, and their peripheral surfaces (side surfaces and distal end surfaces) are rounded. As will be explained also in the "blood vessel harvesting method" described later, the protection section 541 is moved along and between fat and skin while dissecting them when the cutting device 500 is pushed toward the distal side in a living body. Since the fat and the skin having different properties are easy to dissect, even if the distal portion of the protection section 541 is rounded it can sufficiently exhibit a dissecting function for dissecting the fat and the skin. In addition, the rounding helps ensure that damaging or cutting of the branch vessel 1100 by the protection section 541 can be restrained, and, further, damaging (cauterization) of the skin by frictional contact with the protection section 541 can be restrained. Similarly, the protection section 542 can be moved along and between fat and fascia while dissecting them when the cutting device 500 is pushed toward the distal side in the living body. Since the fat and the fascia having different properties are easy to dissect, even if the distal portion of the protection section 542 is rounded it can sufficiently exhibit a dissecting function for dissecting the fat and the fascia. In addition, the rounding helps ensure that damaging or cutting of the branch vessel 1100 by the protection section 542 can be restrained, and, further, damaging of the fascia by frictional contact with the protective section 542 can be restrained.

In addition, the cutting device 500 has connection sections 581 and 582 capable of connection with the rails 231 and 232 of the skin-side dissecting device 200, and a connection section 583 capable of connection with the rails 312 and 322 of the fascia-side dissecting device 300. The connection sections 581 and 582 are provided at the protection section 541, and the connection section 583 is provided at the protection section 542. These connection sections 581, 582 and 583 include projected portions corresponding to the shapes of the rails 231, 232, 312, and 322. With the connection sections 581, 582 and 583 thus provided, unintentional detachment of the cutting device 500 from the skin-side dissecting device 200 and the fascia-side dissecting device 300 can be prevented, and the intended procedure can be performed relatively smoothly and accurately.

Blood Vessel Harvesting Method

In accordance with an exemplary embodiment, a blood vessel harvesting method using the blood vessel dissecting device 100 can include a first step of dissecting a great saphenous vein 1000 in the state of being covered with surrounding fat 1200 by use of the blood vessel dissecting device 100, a second step of ligating the great saphenous vein 1000 and then cutting the great saphenous vein 1000, and a third step of extracting the great saphenous vein 1000 from the living body in the state of being covered with the surrounding fat 1200.

First Step

Figure 13:
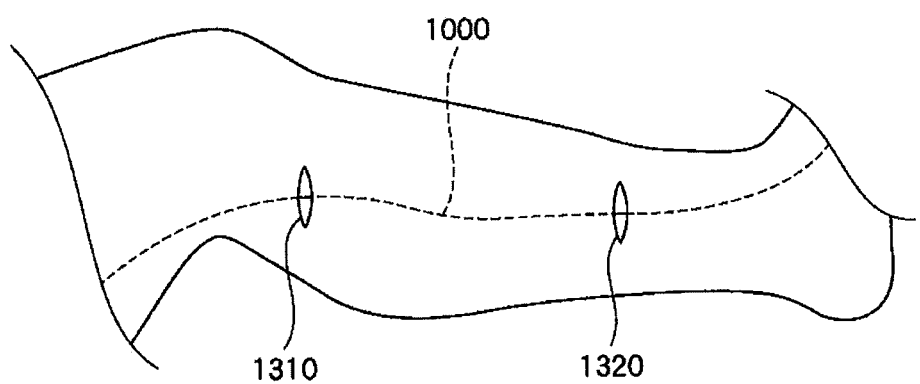
FIG. 13 is a view illustrating a blood vessel dissecting method.

First, the position of the great saphenous vein 1000 to be harvested is confirmed, and skin is incised based on the position. Note that in this operation two parts of the skin are incised, and the great saphenous vein 1000 between the incisions 1310 and 1320 is harvested, as illustrated in FIG. 13.

Figure 14:
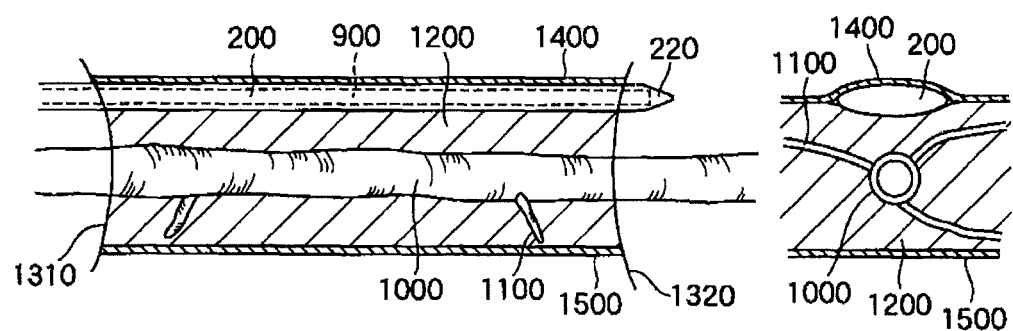
FIG. 14 is a view illustrating the blood vessel dissecting method.

Next, the skin-side dissecting device 200 with the imaging device 900 inserted therein is prepared. Subsequently, while observing the inside of the living body by the imaging device 900, the skin-side dissecting device 200 is inserted into the living body along the great saphenous vein 1000 with a spacing between the skin-side dissecting device 200 and the great saphenous vein 1000. Then, the skin-side dissecting device 200 is located on the upper side (the skin 1400 side) of the great saphenous vein 1000, as depicted in FIG. 14. In this instance, the skin-side dissecting device 200 is disposed in such a manner that the thickness direction thereof coincides substantially with the direction of alignment of the skin-side dissecting device 200 and the great saphenous vein 1000. Note that in this operation, the skin-side dissecting device 200 is inserted through the incision 1310 and a distal portion of the skin-side dissecting device 200 is protruded from the incision 1320. In addition, in this operation, the skin-side dissecting device 200 is inserted between the fat 1200 and the skin 1400 (between tissues having different properties), and the skin 1400 and the fat 1200 are dissected in the thickness direction of the skin-side dissecting device 200 (in the direction of alignment of the skin-side dissecting device 200 and the great saphenous vein 1000). Since such a part as this is easy to dissect, this operation can be performed smoothly and accurately.

Figure 15:
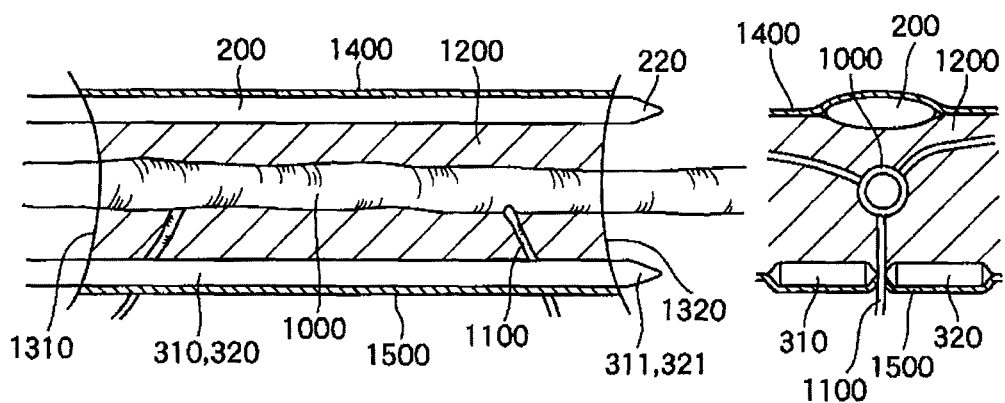
FIG. 15 is a view illustrating the blood vessel dissecting method.

Next, the fascia-side dissecting device 300 (the first and second dissecting devices 310 and 320) is prepared, and the first and second dissecting devices 310 and 320 are sequentially inserted into the living body along the great saphenous vein 1000 with a spacing between them and the great saphenous vein 1000. Then, the first and second dissecting devices 310 and 320 are disposed on the lower side (the fascia 1500 side) of the great saphenous vein 1000, as depicted in FIG. 15. Note that in this operation, the first and second dissecting devices 310 and 320 are inserted via the incision 1310, and their distal portions are protruded from the incision 1320. At this stage, the first dissecting device 310 and the second dissecting device 320 are juxtaposed laterally and are disposed with a spacing therebetween. In addition, the first dissecting device 310 and the second dissecting device 320 are disposed such that the great saphenous vein 1000 is located between them in plan view. In addition, the branch vessels 1100 branched downward from the great saphenous vein 1000 are passing between the first dissecting device 310 and the second dissecting device 320. Note that in this operation, the first and second dissecting devices 310 and 320 are inserted between the fat 1200 and the fascia 1500 (boundary between tissues having different properties), and the fat 1200 and the fascia 1500 are dissected in the thickness direction of the first and second dissecting devices 310 and 320. Since such a part as this is easy to dissect, this operation can be conducted smoothly and appropriately.

Figure 16:
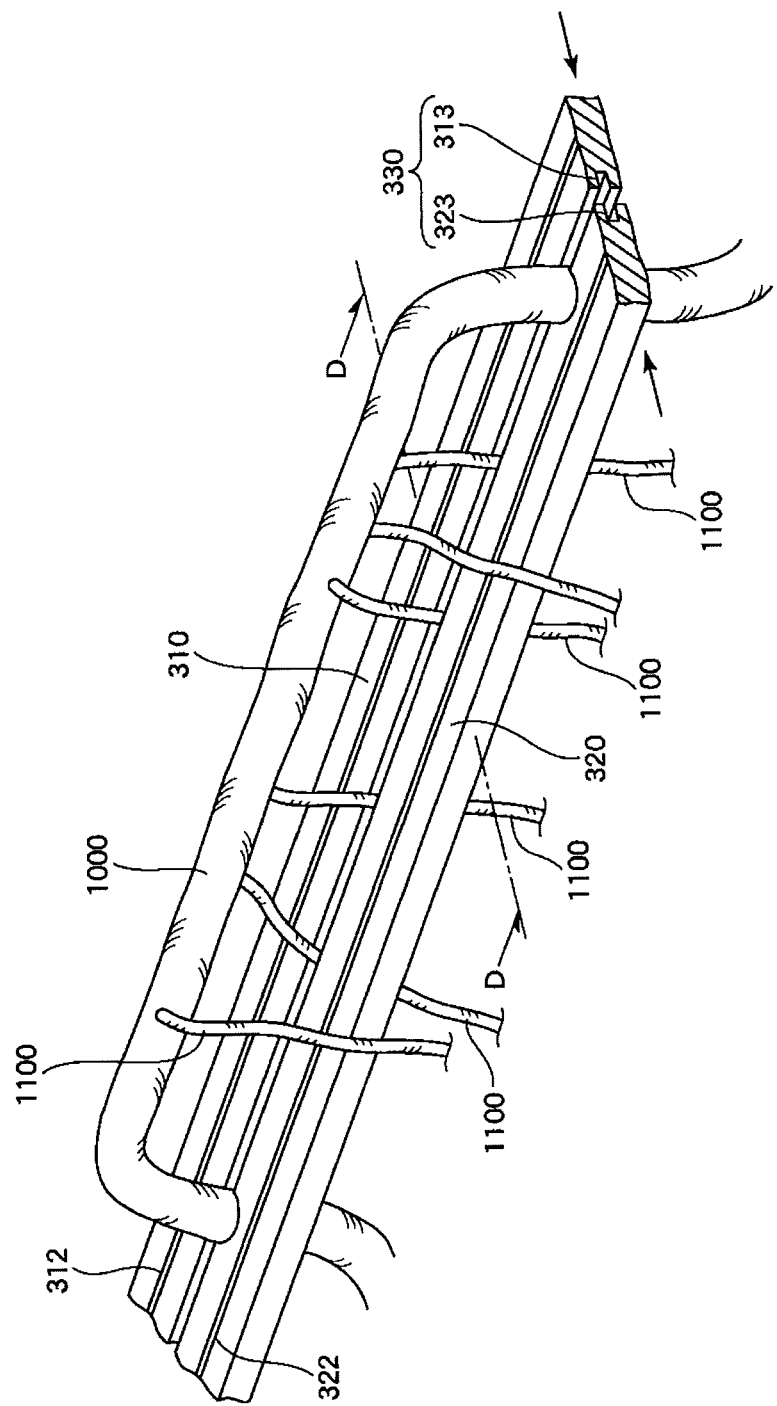
FIG. 16 is a view illustrating the blood vessel dissecting method.

Subsequently, as illustrated in FIG. 16, the first dissecting device 310 and the second dissecting device 320 are abutted on each other (brought close to each other), and they are fixed in such a manner that the abutted state is maintained. It follows that the branch vessels 1100 passing between the first dissecting device 310 and the second dissecting device 320 are held between the devices, and the thus held branch vessels 1100 are exposed in the cavity section 330 in the manner of extending across the cavity section 330. Here, at the time of fixing the first dissecting device 310 and the second dissecting device 320, the distal side of the great saphenous vein 1000 is inserted in and passed through the through-hole 334 composed of the cutouts 314 and 324, and the proximal side of the great saphenous vein 1000 is inserted in and passed through the through-hole 335 including the cutouts 315 and 325, which helps ensure that the great saphenous vein 1000 is not clamped between the first and second dissecting devices 310 and 320, so that damaging or cutting of the great saphenous vein 1000, a lowering in blood flow and the like trouble can be prevented.

Note that the method for fixing the first dissecting device 310 and the second dissecting device 320 is not particularly limited; since both end portions of the first dissecting device 310 and the second dissecting device 320 are exposed from the living body, however, it is preferable to fix the devices by use of fixtures or the like at both end portions. By this method, this operation is facilitated.

Figure 17:
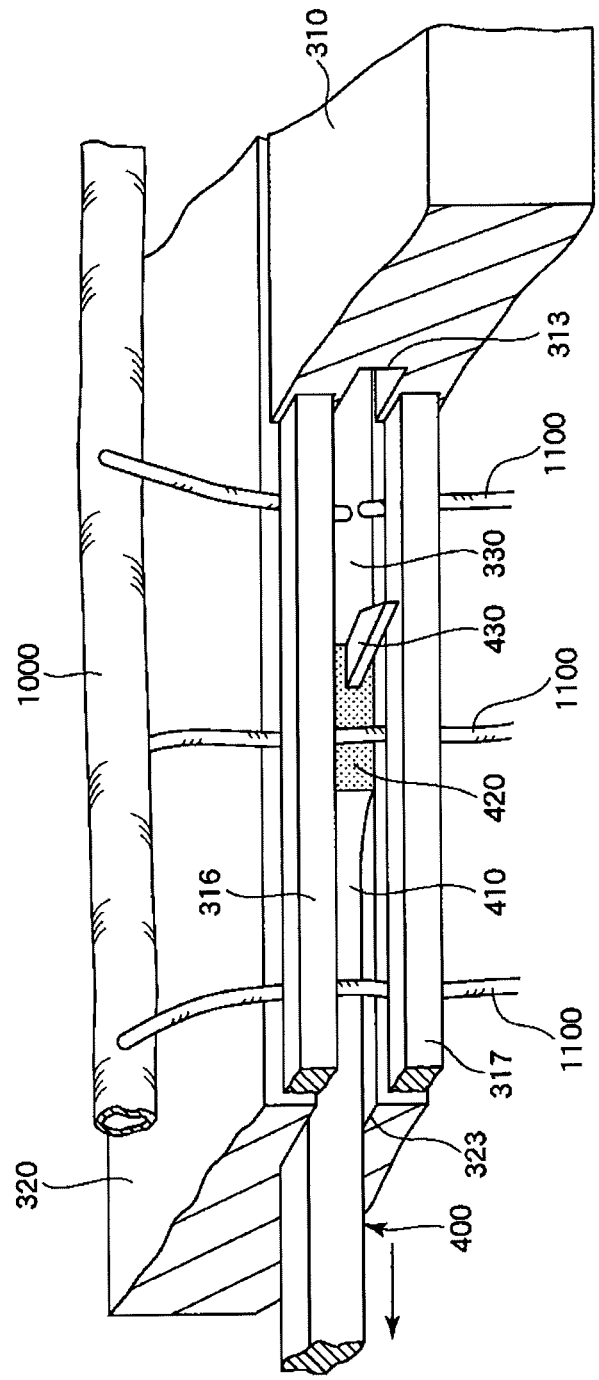
FIG. 17 is a view illustrating the blood vessel dissecting method.

Next, the treating device 400 is prepared, and is inserted into the cavity section 330 (groove 323), starting from its distal side. Subsequently, while impressing a high-frequency alternating voltage between the electrodes 316 and 317 possessed by the first dissecting device 310 and the electrode 420 possessed by the treating device 400, the treating device 400 is moved toward the distal side, as depicted in FIG. 17. By this, the branch vessels 1100 are sequentially stanched and cut, as aforementioned. Here, since the branch vessels 1100 are held between the first and second dissecting devices 310 and 320, displacement of the branch vessels 1100 is restrained, and the treatment of the branch vessels 1100 can be performed relatively assuredly.

Figure 18:
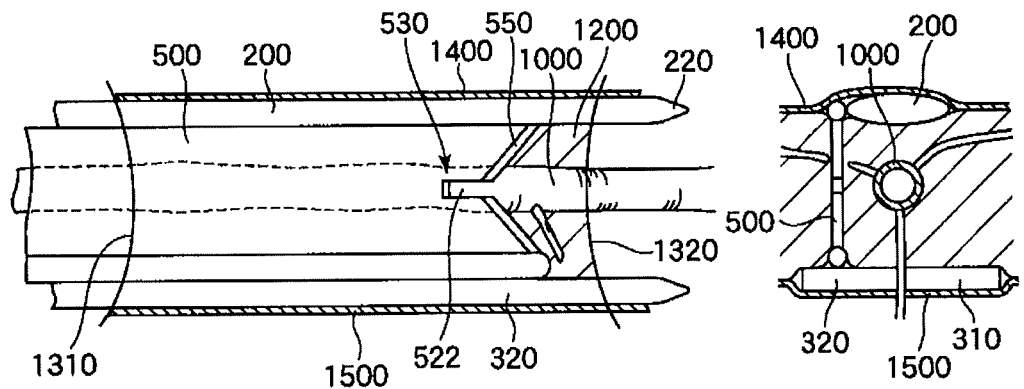
FIG. 18 is a view illustrating the blood vessel dissecting method.

Subsequently, the cutting device 500 is prepared, the connection section 581 is connected to the rail 231 of the skin-side dissecting device 200, and the connection section 583 is connected to the rail 322 of the second dissecting device 320. Then, the cutting device 500 is inserted into the living body while guiding the cutting device 500 with the skin-side dissecting device 200 and the second dissecting device 320, and the cutting device 500 is disposed on one lateral side of the great saphenous vein 1000, as depicted in FIG. 18. In this instance, the cutting device 500 dissects the skin 1400 from the fat 1200 by the protection section 541. Furthermore, the cutting device 500 cuts the fat 1200 present on a lateral side of the great saphenous vein 1000 in the left-right direction (the direction of alignment of the cutting device 500 and the great saphenous vein 1000) by the cutting edge section 550, and stanches and cuts the branch vessels 1100 by the treating section 530.

Here, in accordance with an exemplary embodiment, since the width W1 of the skin-side dissecting device 200 is greater than the outside diameter of the great saphenous vein

1000 as aforementioned, the cutting device 500 can be pushed forward along the great saphenous vein 1000 with a lateral spacing between the cutting device 500 and the great saphenous vein 1000, as depicted in FIG. 18, so that damaging of the great saphenous vein 1000 during this operation can be prevented. In addition, since the protection sections 541 and 542 are rounded, the possibility of damaging of the skin 1400 and the fascia 1500 by contact with the cutting device 500 can be reduced.

Figure 19:
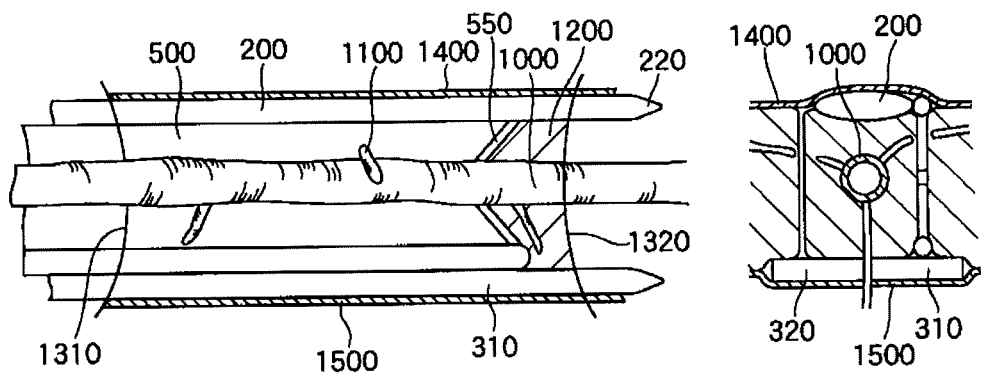
FIG. 19 is a view illustrating the blood vessel dissecting method.

Next, the cutting device 500 is withdrawn, the connection section 582 of the thus withdrawn cutting device 500 is connected to the rail 232 of the skin-side dissecting device 200, and the connection section 583 is connected to the rail 312 of the first dissecting device 310. Then, like in the preceding operation, the cutting device 500 is inserted into the living body while guiding the cutting device 500 with the skin-side dissecting device 200 and the first dissecting device 310, and the cutting device 500 is disposed on the other lateral side of the great saphenous vein 1000, as depicted in FIG. 19. By this, the fat 1200 is cut in the left-right direction, and the branch vessels 1100 are stanched and cut by the treating section 530.

By the above operations, the fat 1200 surrounding the great saphenous vein 1000 is dissected over the entire circumference thereof, and the great saphenous vein 1000 is dissected in the state of being covered with the surrounding fat 1200. Note that the thickness of the fat 1200 dissected together with the great saphenous vein 1000 and located in the surroundings of the great saphenous vein 1000 is not particularly limited, but is preferably, for example, approximately 0.1 mm to 10 mm, more preferably approximately 1 mm to 8 mm, and further preferably approximately 3 mm to 5 mm.

Second Step

Subsequently, the skin-side dissecting device 200, the first dissecting device 310, the second dissecting device 320 and the cutting device 500 are withdrawn from the living body, and both ends of the part to be harvested of the great saphenous vein 1000 are ligated and cut.

Third Step

Next, the great saphenous vein 1000 is taken out of the living body in the state of being covered with the surrounding fat 1200, through the incision 1310 or the incision 1320.

By the first step, the second step and the third step as above, the great saphenous vein 1000 can be harvested in the state of being covered with the surrounding fat 1200. In the method as above-described, for the part which is easy to dissect, the skin-side dissecting device 200 and the fascia-side dissecting device 300 are used for reducing damage such as bleeding, whereas for the fat 1200, which is difficult to dissect, the cutting device 500 is used. Therefore, the great saphenous vein 1000 can be harvested relatively smoothly and with low invasiveness. In addition, since the first step can be conducted without cutting the great saphenous vein 1000, blood is permitted to flow through to the great saphenous vein 1000 for a prolonged time. As a result, the great saphenous vein 1000 put in an ischemic state for a shorter time and, hence, suffering less damage can be harvested.

Particularly, in this embodiment, the dissection on the upper side (the skin 1400 side) of the great saphenous vein 1000 is performed by the skin-side dissecting device 200. Since the number of branch vessels 1100 tends to be smaller on the upper side of the great saphenous vein 1000 than on the lower side of the great saphenous vein 1000, only the dissection by the skin-side dissecting device 200 is conducted without performing the treatment of the branch vessels 1100 on the upper side of the great saphenous vein 1000. On the other hand, a comparatively larger number of branch vessels 1100 are disposed on the lower side of the great saphenous vein 1000; therefore, not only the dissection by the fascia-side dissecting device 300 but also the treatment of the branch vessels 1100 by the treating device 400 is performed on the lower side of the great saphenous vein 1000. With the dissecting devices different in configuration being thus used on the upper side and the lower side of the great saphenous vein 1000, the operation can be carried out smoothly. It is to be noted, however, that the dissection by use of the fascia-side dissecting device 300 may be performed also on the upper side of the great saphenous vein 1000 like on the lower side of the great saphenous vein 1000.

Here, the great saphenous vein 1000 covered with the fat 1200 may become a bypass vessel having a long-term patency rate superior to that of the great saphenous vein 1000 not covered with the fat 1200. This is considered to be for the following reason. The great saphenous vein 1000 is to be used as a bypass vessel for an artery, and in the artery the blood pressure (the internal pressure exerted by blood) is higher than in a vein. Therefore, when a naked great saphenous vein not covered with tissue is used as a bypass vessel, the great saphenous vein may be unable to endure the blood pressure and may expand, with the result of a lowering in blood flow. In addition, the blood vessel wall may be thickened during remodeling (structural modification) or in the process of repairing tissue damages. Such thickening of the blood vessel wall is considered to have an influence on progress of arterial sclerosis. For such a reason, when a naked great saphenous vein not covered with tissue is used as a bypass vessel, blood vessel occlusion may result in the long run.

On the other hand, when the great saphenous vein 1000 is covered with the fat 1200, an effect can thereby be expected in that expansion of the great saphenous vein 1000 is restrained by the fat 1200, and bending or the like of the great saphenous vein 1000 is restrained. Therefore, the aforesaid lowering in blood flow may possibly be restrained. In addition, covering with the fat 1200 can reduce damages to the great saphenous vein 1000, specifically damages to endotheliocytes, smooth muscles, nutrient vessels (capillary plexus) and the like. This may be the reason why the aforesaid thickening of the blood vessel wall can be restrained. These may be the reason why an excellent long-term patency rate can be exhibited when a great saphenous vein 1000 covered with fat 1200 is used as a bypass vessel. Especially in this embodiment, nutrient vessels are remaining at the blood vessel wall of the great saphenous vein 1000 and in the fat 1200; therefore, it is considered that even after bypass grafting, nutrients are supplied to the great saphenous vein 1000 as the bypass vessel, leading to further enhancement of the aforesaid effect.

While this embodiment has been described above, the configuration of the blood vessel dissecting device 100 is not limited to this embodiment. For example, a configuration may be adopted wherein the rails 231 and 232 are omitted from the skin-side dissecting device 200, the rails 312 and 322 are omitted from the fascia-side dissecting device 300, and the connection sections 581, 582 and 583 are omitted from the cutting device 500. In this case, for example, the cutting device 500 may be inserted into the living body along the skin-side dissecting device 200 and the fascia-side dissecting device 300 which have precedingly been inserted into the living body.

In addition, the cutting device 500 is not specifically restricted so long as it can cut the fat 1200. For example, a configuration wherein the fat 1200 is cut by a device, for example, like a pair of scissors may be adopted.

In addition, the blood vessel harvesting method is not limited to the procedure in this embodiment. For instance, the order in which the skin-side dissecting device 200, the fascia-side dissecting device 300 and the cutting device 500 are inserted is not particularly restricted, and any one of the parts on the left side, the right side, the upper side and the lower side of the great saphenous vein 1000 may be dissected first. Specifically, for example, the fascia-side dissecting device 300, the skin-side dissecting device 200 and the cutting device 500 may be inserted in this order. In addition, the skin-side dissecting device 200, the cutting device 500 and the fascia-side dissecting device 300 may be inserted in this order. Further, and the cutting device 500, the skin-side dissecting device 200 and the fascia-side dissecting device 300 may be inserted in this order. In addition, at least two of the cutting device 500, the skin-side dissecting device 200 and the fascia-side dissecting device 300 may be inserted simultaneously.

In addition, while only one cutting device 500 is used in this embodiment, two cutting devices 500 may be used. In that case, for example, first, the first cutting device 500 may be disposed on one of the left and right sides of the great saphenous vein 1000, and then the second cutting device 500 may be disposed on the other of the left and right sides of the great saphenous vein 1000. According to such a procedure, it is unnecessary to withdraw the cutting device 500 in the course of the procedure, so that the aforesaid procedure can be performed smoothly.

While the skin-side dissecting device 200 is inserted between the fat 1200 and the skin 1400 in this embodiment, the insertion position of the skin-side dissecting device 200 is not specifically restricted; for example, the insertion position may be between such tissues having different properties as the fat 1200 and a blood vessel (a blood vessel other than the great saphenous vein 1000). In addition, the insertion position is not limited to the position between tissues having different properties (at the boundary between tissues having different properties, at a tissue between tissues having different properties, or the like); for example, the skin-side dissecting device 200 may be inserted into fat 1200, and the fat 1200 may be dissected.

Similarly, while the fascia-side dissecting device 300 is inserted between the fat 1200 and the fascia 1500 in this embodiment, the insertion position of the fascia-side dissecting device 300 is not particularly limited. For example, the insertion position may be between such tissues having different properties as fat 1200 and a bone, or fascia 1500 and a bone. In addition, the insertion position is not limited to the position between tissues having different properties (at the boundary between tissues having different properties, at a tissue between tissues having different properties, or the like); for example, the fascia-side dissecting device 300 may be inserted into fat 1200, and the fat 1200 may be dissected.

In addition, while the fat 1200 is cut by the cutting device 500 in this embodiment, the tissue to be cut by the cutting device 500 is not limited to the fat, but may be, for example, a tissue between a skin-fat boundary and a fat-muscle boundary, a tissue between a skin-fat boundary and a fat-interosseous membrane boundary, a connective tissue, a tissue between a skin layer and a muscle layer, a tissue between a skin layer and an interosseous membrane, or a branch vessel.

While the skin-side dissecting device 200 and the fascia-side dissecting device 300 are disposed in a spaced state such as not to make contact with the great saphenous vein 1000 in this embodiment, the skin-side dissecting device 200 and the fascia-side dissecting device 300 may be disposed in contact with the great saphenous vein 1000. Specifically, the skin-side dissecting device 200 and the fascia-side dissecting device 300 may be inserted between the great saphenous vein 1000 and the fat 1200.

Figure 20:
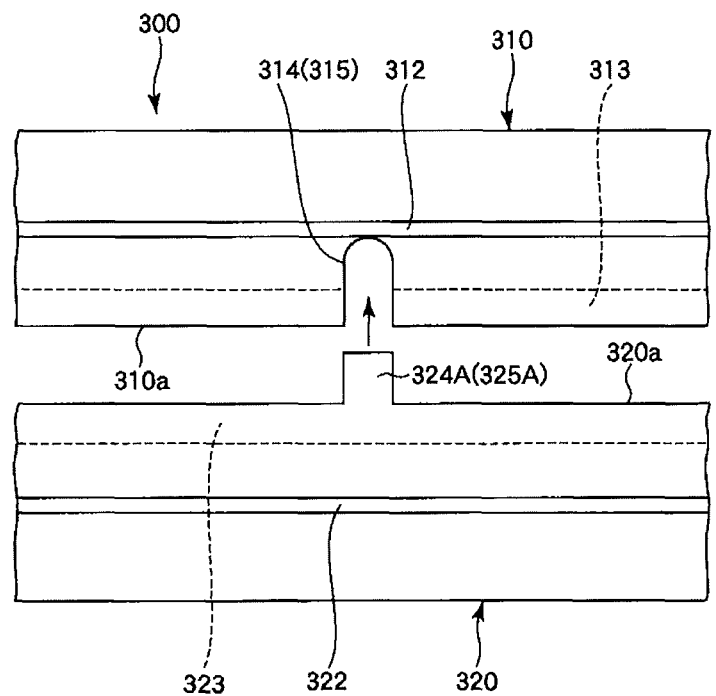
FIG. 20 is a plan view depicting a fascia-side dissecting device possessed by a blood vessel dissecting device according to a second embodiment of the present disclosure.
Figure 21:
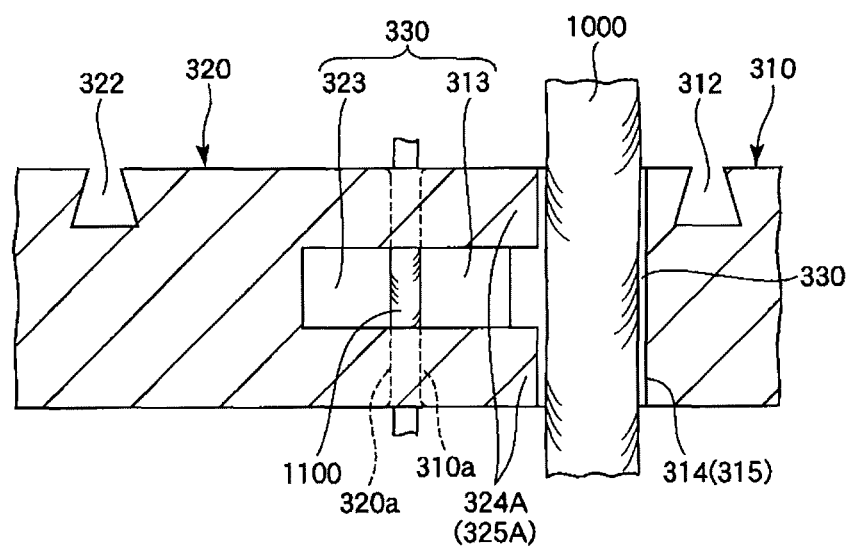
FIG. 21 is a sectional view of the fascia-side dissecting device depicted in FIG. 20.

FIG. 20 is a plan view of a fascia-side dissecting device possessed by a blood vessel dissecting device according to a second embodiment of the present disclosure. FIG. 21 is a sectional view of the fascia-side dissecting device depicted in FIG. 20.

In describing the second embodiment below referring to these figures, differences from the aforementioned first embodiment will be described primarily, and descriptions of the same items as above will be omitted.

This embodiment is the same as the aforementioned first embodiment, except mainly for a difference in the configuration of the fascia-side dissecting device.

As depicted in FIG. 20, a first dissecting device 310 in this embodiment has cutouts 314 and 315 provided to extend to an outer side (to the side of a side surface opposite to a butt surface 310a) than a groove 313 in plan view. On the other hand, in a second dissecting device 320, cutouts 324 and 325 are omitted, and, instead, there are provided projected portions 324A and 325A which enter into the cutouts 314 and 315 when the second dissecting device 320 is abutted on the first dissecting device 310. When the first dissecting device 310 and the second dissecting device 320 as above are abutted on each other, as depicted in FIG. 21, the projected portion 324A enters the cutout 314, and a through-hole 334 is formed therebetween. Similarly, the projected portion 325A enters the cutout 315, and a through-hole 335 is formed therebetween.

According to this configuration, the through-holes 334 and 335 are formed at positions deviated from a cavity section 330, so that contact between a great saphenous vein 1000 inserted in and passed through the through-holes 334 and 335 and a treating device 400 (particularly, a cutting section 430) inserted in the cavity section 330 is prevented. Therefore, damaging or cutting of the great saphenous vein 1000 by the cutting section 430 can be prevented. In addition, according to such a configuration, it is unnecessary for the cutting section 430 to be configured such as to be displaceable between an operating state and a retracted state as in the aforementioned first embodiment, and the cutting section 430 can be fixed in the operating state. Therefore, the configuration of the treating device 400 is simplified, and the treatment by the treating device 400 can be performed smoothly.

By the second embodiment, also, the same or equivalent effects to those of the aforementioned first embodiment can be exhibited.

Alternatively, the treating device 400 may be configured to cut and stanch branch vessels 1100 when it is pushed forward from the proximal portion side toward the distal portion side. In that case, an electrode 420 may be disposed on the distal portion side of the treating device 400, and the cutting section 430 may be disposed on the proximal portion side. Furthermore, where a groove 323 on the proximal portion side of the second dissecting device 320 is enlarged in depth, the treating device 400 can be inserted while avoiding the great saphenous vein 1000. Accordingly, it is unnecessary for the cutting section 430 to have a rotating function, and the treating device 400, for example, can be simplified.

Figure 22:
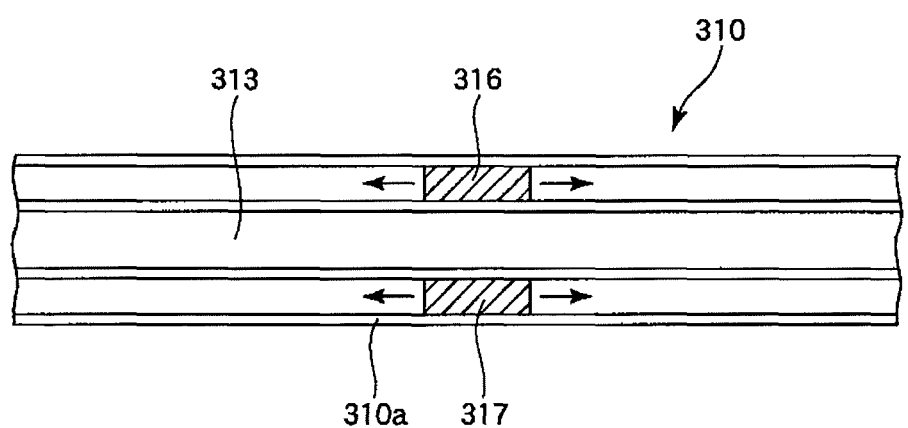
FIG. 22 is a lateral view of a first dissecting device possessed by a blood vessel dissecting device according to a third embodiment of the present disclosure.
Figure 23:
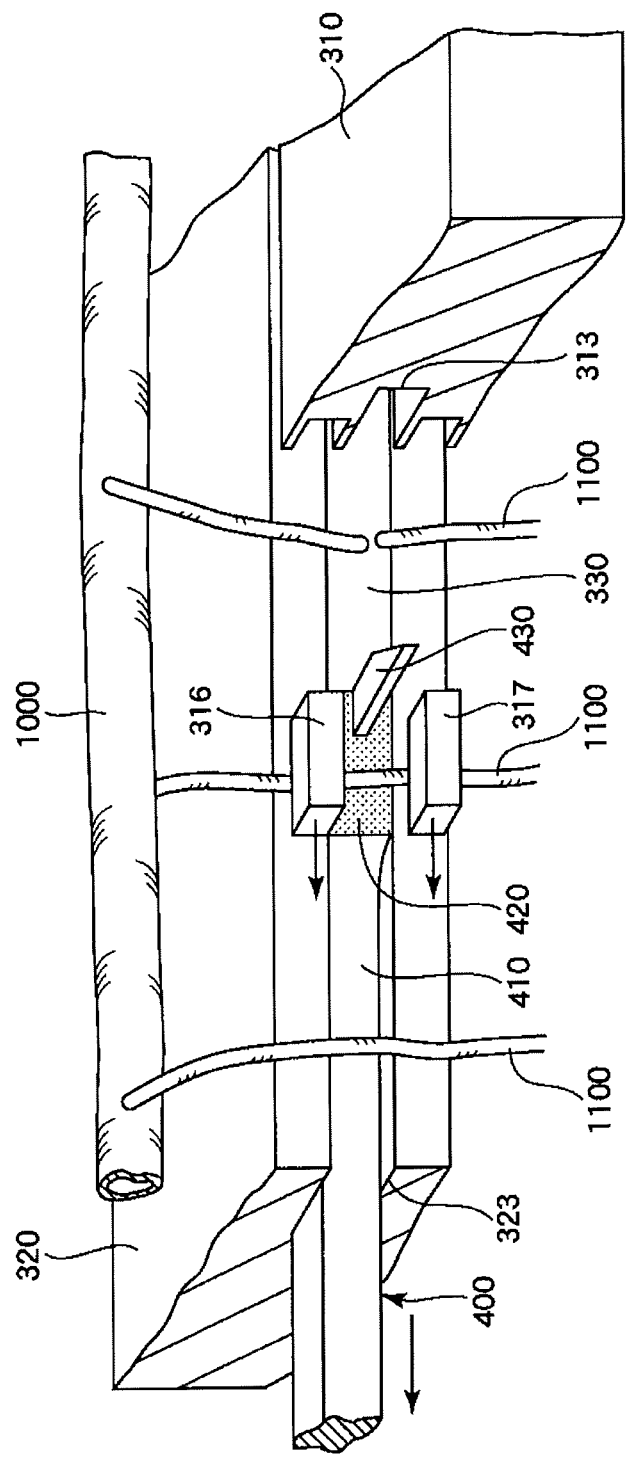
FIG. 23 illustrates a branch vessel treating method.

FIG. 22 is a lateral view of a first dissecting device possessed by a blood vessel dissecting device according to a third embodiment of the present disclosure. FIG. 23 illustrates a branch vessel treating method.

In describing the third embodiment below referring to these figures, differences from the aforementioned embodiments will be described primarily, and descriptions of the same items as above will be omitted.

This embodiment is the same as the aforementioned first embodiment except mainly for a difference in the configuration of the first dissecting device.

As illustrated in FIG. 22, in a first dissecting device 310 in this embodiment, electrodes 316 and 317 are formed to be shorter than in the aforementioned first embodiment. The length of the electrodes 316 and 317 is not particularly limited, and may be, for example, approximately 5 mm to 2 cm. In addition, the electrodes 316 and 317 are integrally movable in the axial direction of the first dissecting device 310 (in the directions of arrows in FIG. 22).

In such a configuration, as depicted in FIG. 23, a treating device 400 is inserted in a cavity section 330, and an electrode 420 is disposed to face the electrodes 316 and 317. With the relative positional relationship between the electrodes 316 and 317 and the electrode 420 maintained, a treating device 400 is slid toward the distal side while impressing a high-frequency alternating voltage between the electrodes 316 and 317 and the electrode 420, whereby branch vessels 1100 can sequentially be thermally coagulated and cut.

According to such a configuration, a region in which an electric field is generated can be narrowed, so that the electric field can be made to act on the branch vessels 1100 more effectively, and the branch vessels 1100 can be reliably stanched.

By the third embodiment as above, also, the same or equivalent effects to those of the aforementioned first embodiment can be exhibited.

Figure 24:
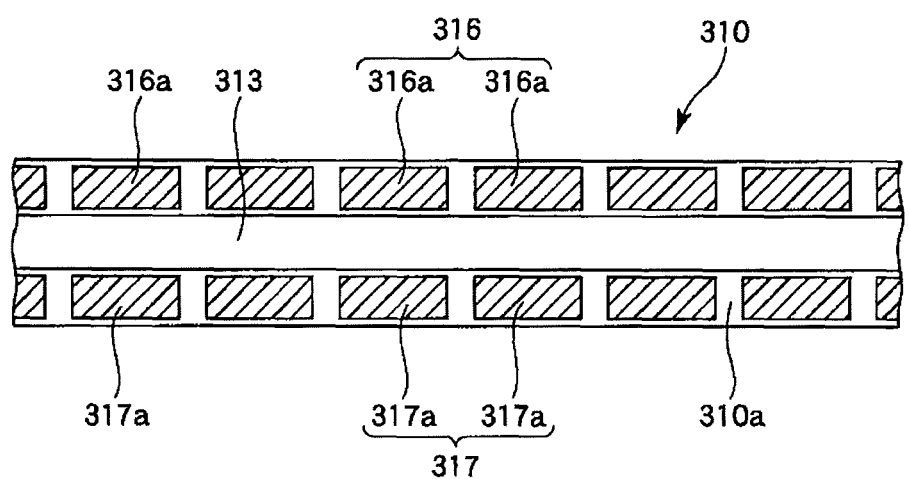
FIG. 24 is a lateral view of a first dissecting device possessed by a blood vessel dissecting device according to a fourth embodiment of the present disclosure.
Figure 25:
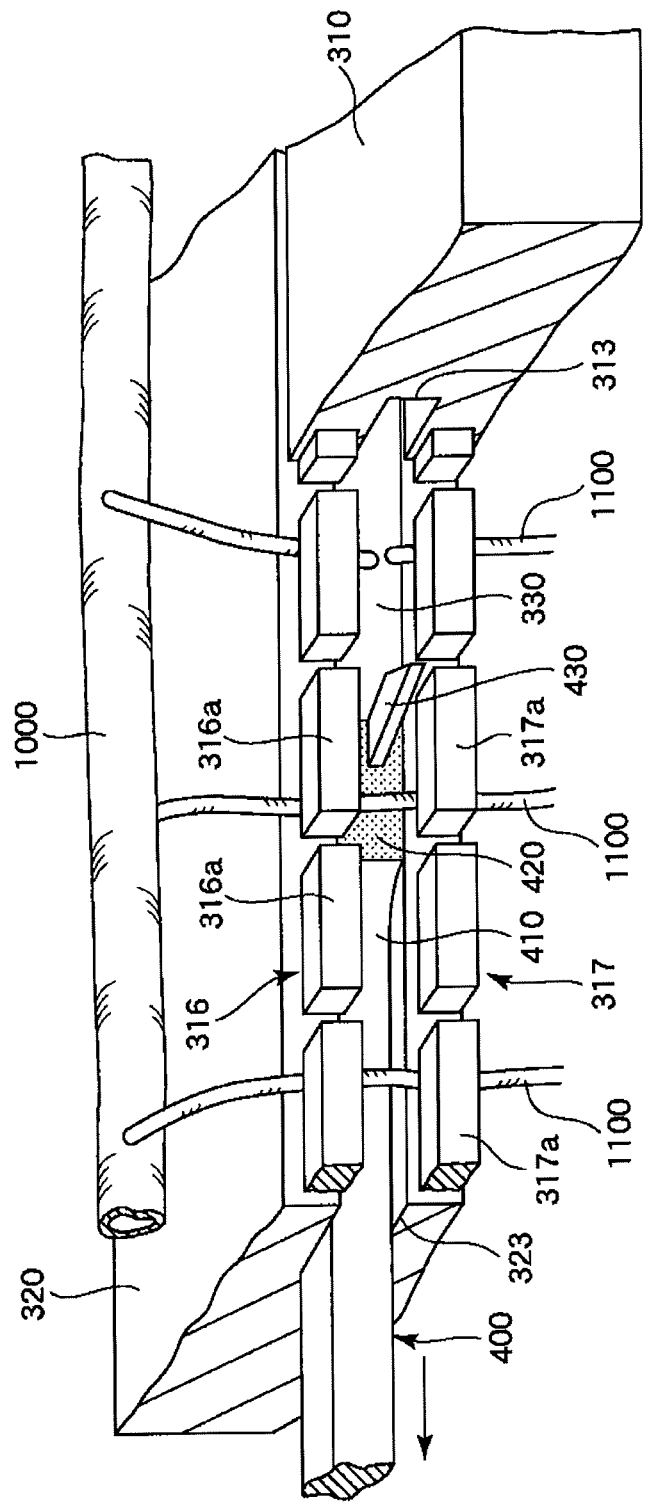
FIG. 25 illustrates a branch vessel treating method.
Figure 26:
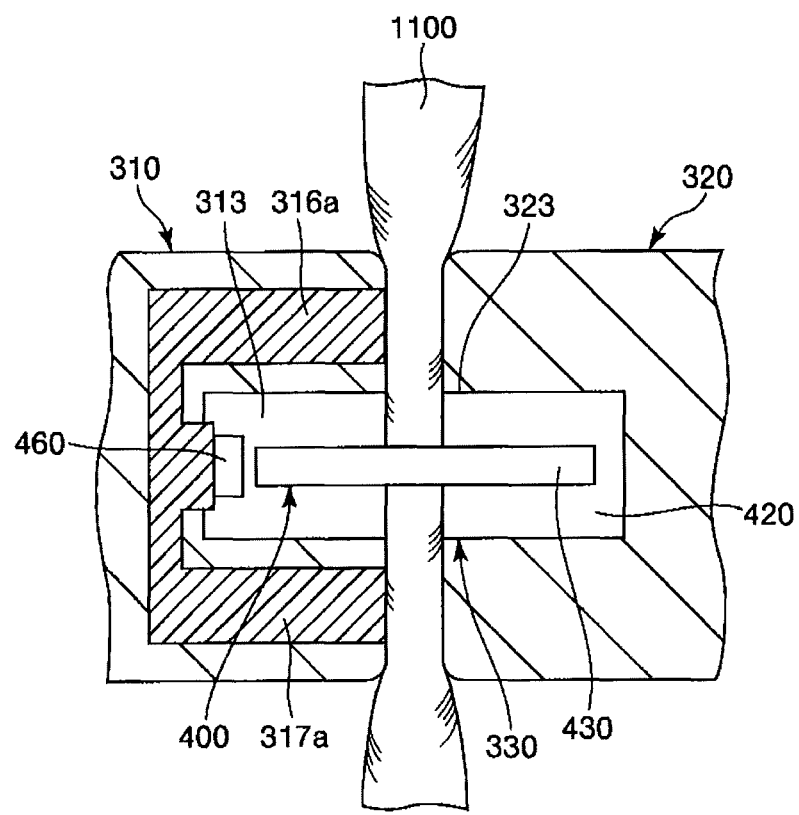
FIG. 26 is a sectional view depicting an example of a treating device.

FIG. 24 is a lateral view of a first dissecting device possessed by a blood vessel dissecting device according to a fourth embodiment of the present disclosure. FIG. 25 illustrates a branch vessel treating method. FIG. 26 is a sectional view depicting an example of a treating device.

In describing the fourth embodiment below referring to these figures, differences from the aforementioned embodiments will be described primarily, and descriptions of the same items as above will be omitted.

This embodiment is the same as the aforementioned first embodiment except mainly for a difference in the configuration of the first dissecting device.

As illustrated in FIG. 24, in a first dissecting device 310 in this embodiment, electrodes 316 and 317 are each divided into a plurality of portions. The electrodes 316 and 317 have pluralities of electrode pieces 316a and 317a, which are aligned in a spaced manner in the axial direction of the first dissecting device 310. The electrode pieces 316a and 317a opposed to each other with a groove 313 therebetween are connected to be the same in potential. Note that the length of the electrode pieces 316a and 317a is not particularly limited, and may be, for example, approximately 5 mm to 2 cm.

According to such a configuration, as depicted in FIG. 25, when a treating device 400 inserted in a cavity section 330 is slid toward the distal side, the electrode pieces 316a and 317a on which a voltage is impressed are switched according to the movement of the treating device 400 in such a manner that a high-frequency alternating voltage is impressed between an electrode 420 being moved and the electrode pieces 316a and 317a facing the electrode 420. By this, branch vessels 1100 can sequentially be thermally coagulated and cut.

According to such a configuration, a region in which an electric field is generated can be narrowed, so that the electric field can be made to effectively act on the branch vessels 1100, and the branch vessels 1100 can be reliably thermally coagulated (stanched).

Note that a mechanism for switching the electrode pieces 316a and 317a on which the high-frequency alternating voltage is impressed is not specifically restricted. For example, the switching mechanism may have a configuration including a detection section for detecting the position of the electrode 420, and a switching section for switching the electrode pieces 316a and 317a on which to impress the voltage, wherein the electrode pieces 316a and 317a on which to impress the voltage are switched according to the results of detection by the detection section. In addition, as depicted in FIG. 26, the treating device 400 may have a configuration wherein a conductive lead wire 460 is provided which is opposed to the electrode 420 and is moved within the groove 313 together with the electrode 420, and a voltage is impressed between the electrode pieces 316a and 317a contacted by the lead wire 460 and the electrode 420.

By the fourth embodiment as above, also, the same or equivalent effects to those of the aforementioned first embodiment can be exhibited.

Note that the layout of the electrodes is not limited to those in the aforementioned first to fourth embodiments. For example, a configuration may be adopted wherein the treating device 400 is not provided with the electrode 420, the electrodes depicted in FIG. 22 are disposed on the side of the second dissecting device 320, and a bipolar structure is configured between a first dissecting device 310 side and the second dissecting device 320 side. In this case, that part of a branch vessel 1100, which is pressed can be thermally coagulated in a reliable manner.

Figure 27:
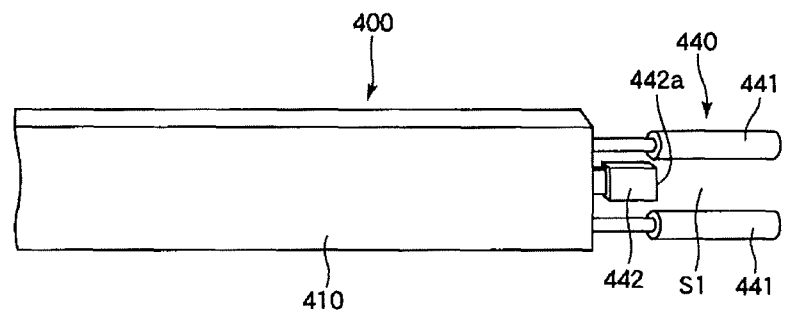
FIG. 27 is a perspective view of a treating device possessed by a blood vessel dissecting device according to a fifth embodiment of the present disclosure.
Figure 28:
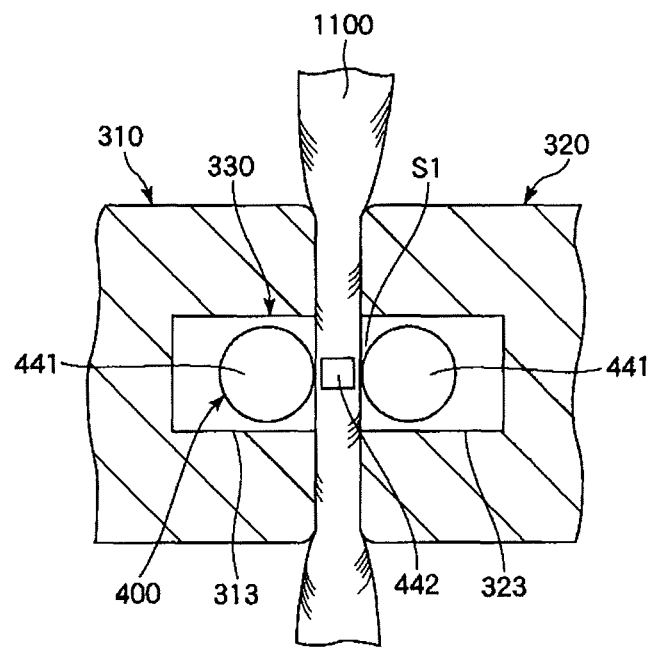
FIG. 28 is a sectional view depicting a state in which the treating device depicted in FIG. 27 is inserted in a cavity section.

FIG. 27 is a perspective view of a treating device possessed by a blood vessel dissecting device according to a fifth embodiment of the present disclosure. FIG. 28 is a sectional view illustrating a state in which the treating device depicted in FIG. 27 is inserted in a cavity section.

In describing the fifth embodiment below referring to these figures, differences from the aforementioned embodiments will be described primarily, and descriptions of the same items as above will be omitted.

This embodiment is the same as the aforementioned first embodiment except mainly for differences in the configurations of the first dissecting device and the treating device.

A first dissecting device 310 in this embodiment has a configuration obtained by omitting the electrodes 316 and 317 from the configuration in the aforementioned first embodiment.

A treating device 400 in this embodiment includes an operation section 410, and a treating section 440 provided at a distal portion of the operation section 410, as depicted in FIG. 27. In addition, the treating section 440 has a bipolar structure including electrodes 441 and 442.

The electrodes (first electrodes) 441 are provided in a pair opposed in a width direction (a direction orthogonal to the axial direction) of the operation section 410. A space S1 for guiding a branch vessel 1100 is formed between the electrode 441 on one side and the electrode 441 on the other side.

In addition, the electrode (second electrode) 442 is located between the electrode 441 on the one side and the electrode 441 on the other side when viewed in the axial direction of the operation section 410, and its distal end is located on the more proximal side than the distal end of the electrode 441 in lateral view. In other words, the electrode 442 is disposed on the proximal side (the rear side in regard of the moving direction) of the space S1. In addition, a distal portion 442a of the electrode 442 functions also as a cutting section 430, and is sharp to such an extent as to be able to cut the branch vessel 1100.

As illustrated in FIG. 28, in a state in which the treating device 400 is inserted in the cavity section 330, the electrode 441 on one side is located in a groove 313, whereas the electrode 441 on the other side is located in a groove 323, and the electrode 442 is disposed to be situated across the boundary between the grooves 313 and 323. Therefore, with the treating device 400 slid toward the distal side while impressing a high-frequency alternating voltage between the electrodes 441 and 442, branch vessels 1100 can sequentially be guided into the space S1 and thermally coagulated, and the thermally coagulated branch vessels 1100 can be cut by the electrode 442.

In this embodiment, a configuration wherein a branch vessel 1100 is flattened by pressing and the flattened part is thermally coagulated is not adopted. Instead, the treating device 400 is slid toward the distal side to exert a tension on the branch vessel 1100, whereby that part of the blood vessel which is to be thermally coagulated is flattened, and the thus flattened part is thermally coagulated and is stanched and cut.

According to this configuration, it is sufficient for the electrodes 441 and 442 for generating an electric field to be disposed only in the treating device 400, so that the configuration of the first dissecting device 310, for example, is simplified.

By the fifth embodiment as above, also, the same or equivalent effect as that in the aforementioned first embodiment can be produced.

Figure 29:
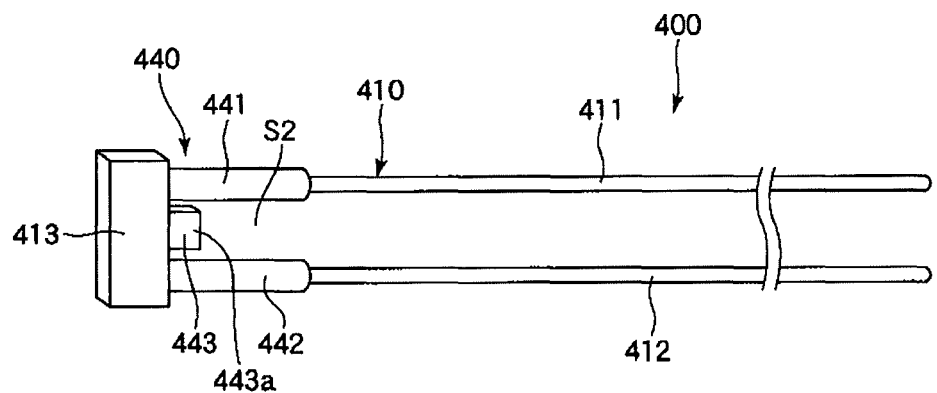
FIG. 29 is a perspective view of a treating device possessed by a blood vessel dissecting device according to a sixth embodiment of the present disclosure.
Figure 30:
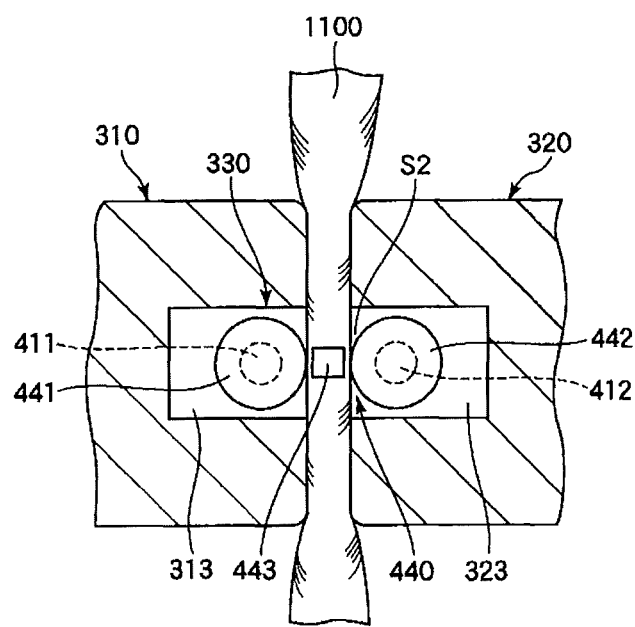
FIG. 30 is a sectional view depicting a state in which the treating device depicted in FIG. 29 is inserted in a cavity section.

FIG. 29 is a perspective view of a treating device possessed by a blood vessel dissecting device according to a sixth embodiment of the present disclosure. FIG. 30 is a sectional view depicting a state where the treating device depicted in FIG. 29 is inserted in a cavity section.

In describing the sixth embodiment below referring to these figures, differences from the aforementioned embodiments will be described primarily, and descriptions of the same items as above will be omitted.

This embodiment is the same as the aforementioned first embodiment except mainly for differences in the configurations of the first dissecting device and the treating device.

A first dissecting device 310 in this embodiment has a configuration obtained by omitting the electrodes 316 and 317 from the configuration in the aforementioned first embodiment.

As depicted in FIG. 29, a treating device 400 in this embodiment includes an operation section 410, and a treating section 440 provided at a proximal portion of the operation section 410. The operation section 410 includes a pair of bar-shaped portions (operating pieces) 411 and 412 disposed to face each other with a spacing therebetween, and a connection section 413 for connecting the bar-shaped portions 411 and 412 on the proximal side.

In addition, the treating section 440 includes a pair of electrodes 441 and 442, and a cutting section 443. The electrode (first electrode) 441 is provided at a proximal portion of the bar-shaped portion 411, while the electrode (second electrode) 442 is provided at a proximal portion of the bar-shaped portion 412. Between the electrode 441 and the electrode 442 is formed a space S2 for guiding a branch vessel 1100.

In addition, the cutting section 443 is provided to project toward the distal side from the connection section 413. In addition, the cutting section 443 is located between the electrodes 441 and 442 when viewed in the axial direction of the operation section 410, and its distal end is located on the more proximal side than the distal end of the electrodes 441 and 442 in lateral view. In other words, the cutting section 443 is disposed on the proximal side (the rear side in regard of the moving direction) of the space S2. In addition, a distal portion 443a of the cutting section 443 is sharp to such an extent as to be able to cut the branch vessel 1100.

As depicted in FIG. 30, in a state where the treating device 400 is inserted in a cavity section 330, the bar-shaped portion 411 and the electrode 441 are located in a groove 313, whereas the bar-shaped portion 412 and the electrode 442 are located in a groove 323, and the cutting section 443 is disposed to be situated across the boundary between the grooves 313 and 323. Therefore, with the treating device 400 slid toward the distal side while impressing a high-frequency alternating voltage between the electrodes 441 and 442, the branch vessels 1100 can sequentially be guided into the space S2 and thermally coagulated, and the thermally coagulated branch vessels 1100 can be cut by the cutting section 443.

According to this configuration, it is sufficient for the electrodes 441 and 442 for generating an electric field to be disposed only in the treating device 400, so that the configuration of the first dissecting device 310, for example, is simplified.

By the sixth embodiment as above, also, the same or equivalent effects to those of the aforementioned first embodiment can be exhibited.

Figure 31:
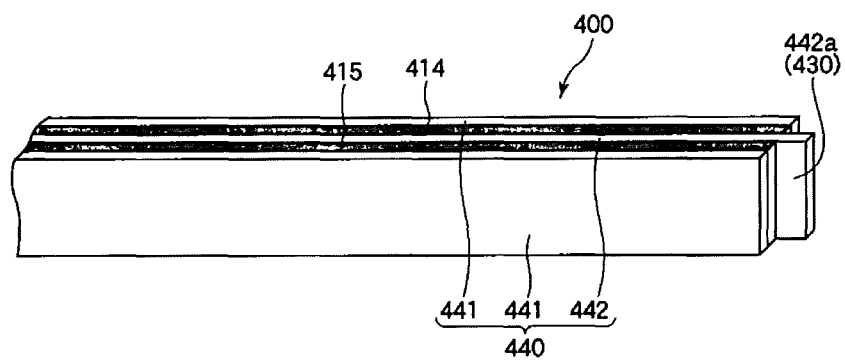
FIG. 31 is a perspective view of a treating device possessed by a blood vessel dissecting device according to a seventh embodiment of the present disclosure.
Figure 32:
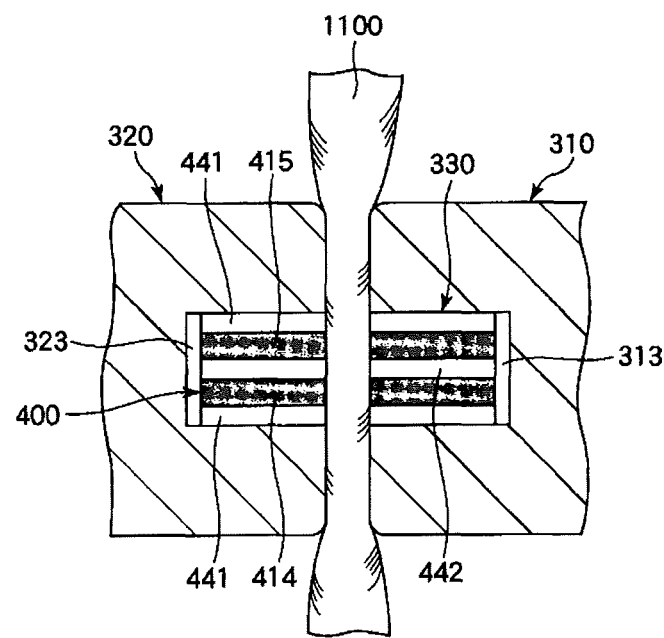
FIG. 32 is a sectional view depicting a state in which the treating device depicted in FIG. 31 is inserted in a cavity section.
Figure 33:
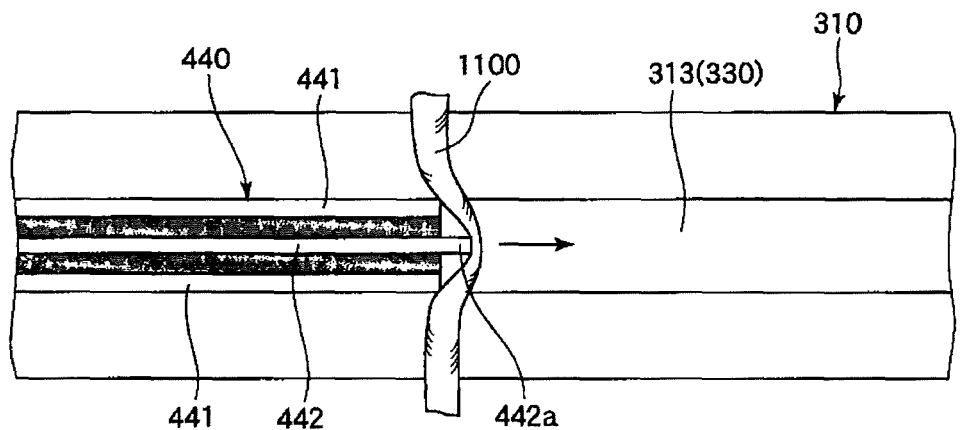
FIG. 33 is a sectional view illustrating a branch vessel treating method.
Figure 34:
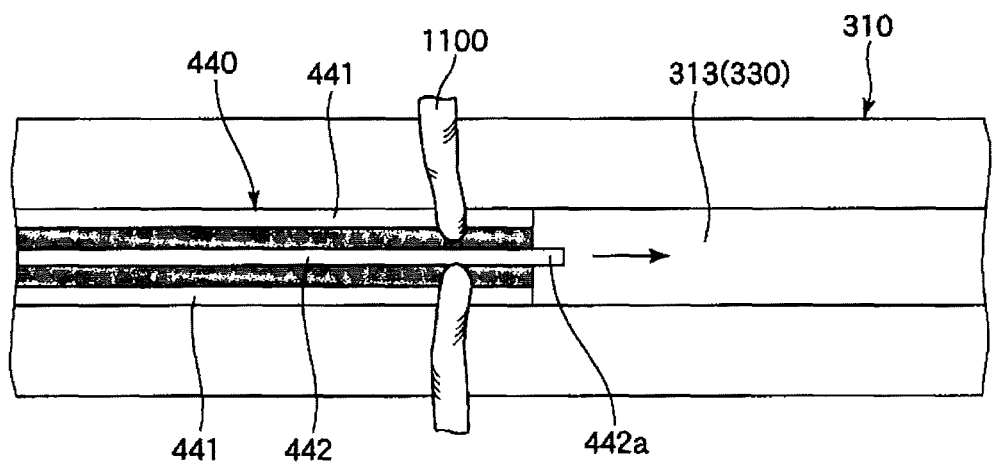
FIG. 34 is a sectional view illustrating the branch vessel treating method.

FIG. 31 is a perspective view of a treating device possessed by a blood vessel dissecting device according to a seventh embodiment of the present disclosure. FIG. 32 is a sectional view illustrating a state in which the treating device depicted in FIG. 31 is inserted in a cavity section. FIGS. 33 and 34 are sectional views illustrating a branch vessel treating method.

In describing the seventh embodiment below referring to these figures, differences from the aforementioned embodiments will be described primarily, and descriptions of the same items as above will be omitted.

This embodiment is the same as the aforementioned first embodiment except mainly for differences in the configurations of the first dissecting device and the treating device.

A first dissecting device 310 in this embodiment has a configuration obtained by omitting the electrodes 316 and 317 from the configuration in the aforementioned first embodiment.

As depicted in FIG. 31, a treating device 400 in this embodiment has a treating section 440. The treating section 440 includes plate-shaped electrodes 441 and 442. The electrodes (second electrodes) 441 are provided such as to face each other with the electrode (first electrode) 442 therebetween. In addition, an insulating plate-shaped portion 414 is sandwiched between the electrode 442 and the electrode 441 on one side, and an insulating plate-shaped portion 415 is sandwiched between the electrode 442 and the electrode 441 on the other side. In addition, a distal portion 442a of the electrode 442 protrudes from the electrodes 441 and the plate-shaped portions 414 and 415. In addition, the distal portion 442a can also function as a cutting section 430, and is sharp to such an extent as to be able to cut branch vessels 1100. Note that an insulating coating, for example, may be applied to surfaces of the electrodes 441 and 442, in place of the plate-shaped portions 414 and 415. In addition, a configuration may also be adopted wherein one electrode 441 and one electrode 442 are laminated on each other.

As depicted in FIG. 32, in a state in which the treating device 400 is inserted in a cavity section 330, the electrodes 441 and 442 are disposed such as to be situated across a boundary between grooves 313 and 323. Therefore, when the treating device 400 is slid toward the distal side while impressing a high-frequency alternating voltage between the electrodes 441 and 442, the branch vessel 1100 is extended and deformed under pressing by the distal portion 442a of the electrode 442, as depicted in FIG. 33, and is thermally coagulated by the action of an electric field generated between the electrodes 441 and 442. When the treating device 400 is further moved toward the distal side, the branch vessel 1100 is cut by the distal portion 442a, as depicted in FIG. 34.

According to this configuration, the electric field is made to act on the branch vessel 1100 in the state where the branch vessel 1100 is extended and deformed (in the state of being flattened into a flat shape), and, therefore, the branch vessel 1100 can be reliably stanched.

By the seventh embodiment as above, also, the same or equivalent effects to those of the aforementioned first embodiment can be produced.

Figure 35:
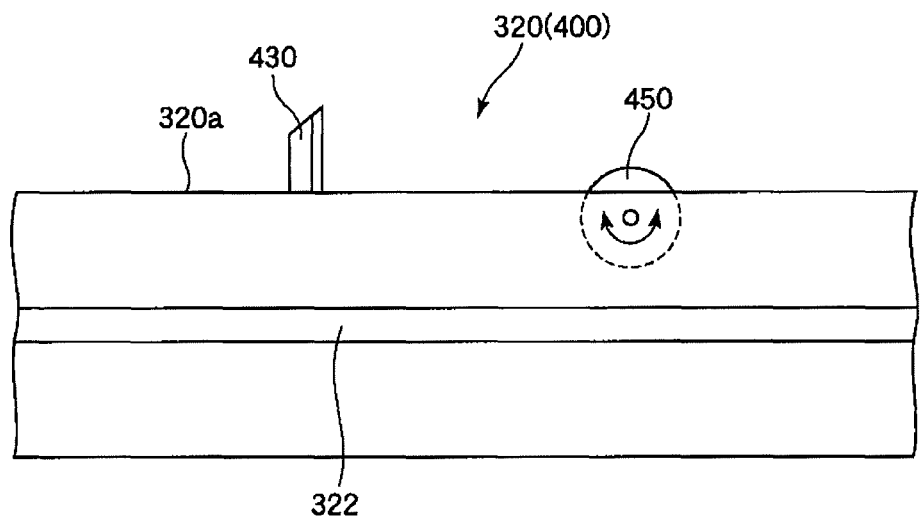
FIG. 35 is a plan view of a second dissecting device possessed by a blood vessel dissecting device according to an eighth embodiment of the present disclosure.
Figure 36:
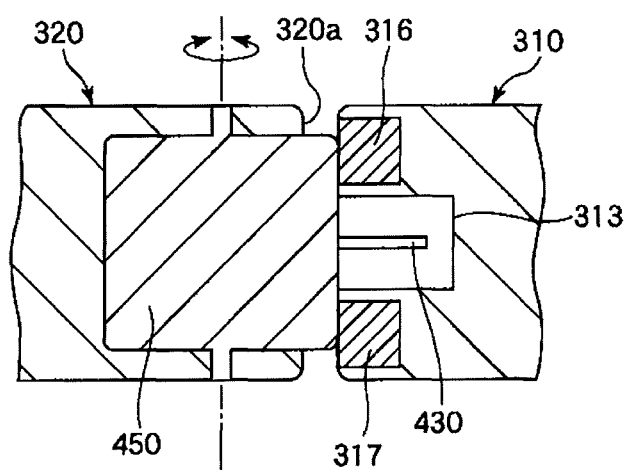
FIG. 36 is a sectional view of the second dissecting device depicted in FIG. 35.
Figure 37:
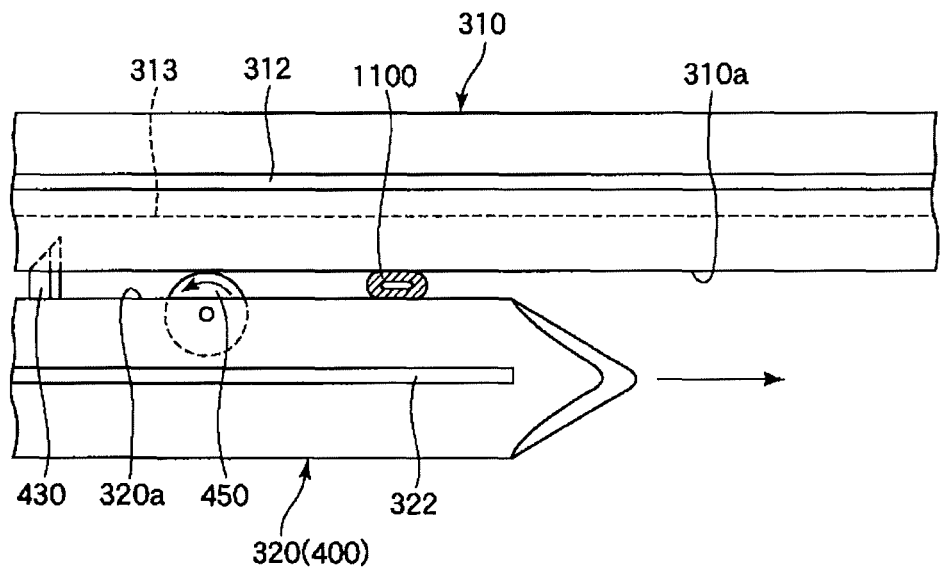
FIG. 37 illustrates a branch vessel treating method.
Figure 38:
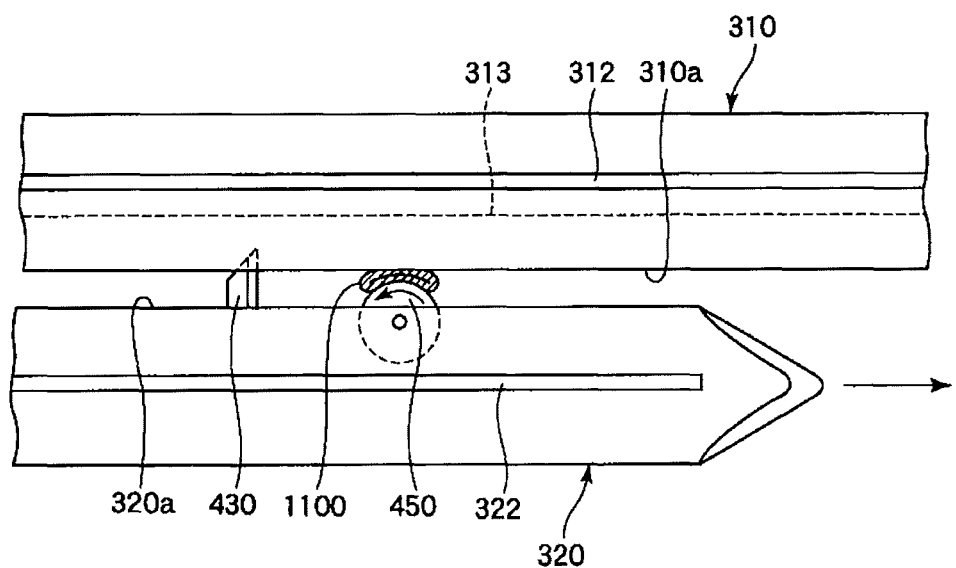
FIG. 38 illustrates the branch vessel treating method.

FIG. 35 is a plan view of a second dissecting device possessed by a blood vessel dissecting device according to an eighth embodiment of the present disclosure. FIG. 36 is a sectional view of the second dissecting device depicted in FIG. 35. FIGS. 37 and 38 illustrate a branch vessel treating method.

In describing the eighth embodiment below referring to these figures, differences from the aforementioned embodiments will be described primarily, and descriptions of the same items as above will be omitted.

This embodiment is the same as the aforementioned first embodiment except mainly that the fascia-side dissecting device functions also as the treating device.

A second dissecting device 320 in this embodiment functions also as a treating device 400. As depicted in FIG. 35, such a second dissecting device 320 includes a roller electrode 450, and a cutting section 430 disposed on the more proximal side than the roller electrode 450. The roller electrode 450 is provided such as to project from a butt surface 320a, and is supported in a rotatable manner. In addition, as depicted in FIG. 36, the roller electrode 450 faces electrodes 316 and 317 possessed by a first dissecting device 310 when the second dissecting device 320 is set along the butt surface 310a of the first dissecting device 310. In addition, the cutting section 430 is provided such as to project from the butt surface 320a, and enters into a groove 313 of the first dissecting device 310 when the second dissecting device 320 is set along the butt surface 310a of the first dissecting device 310.

In this configuration, in a state where the first dissecting device 310 is disposed on the lower side of a great saphenous vein 1000, the second dissecting device 320 is inserted into the living body along the butt surface 310a of the first dissecting device 310, as depicted in FIG. 37, while impressing a high-frequency alternating voltage between the electrodes 316 and 317 and the roller electrode 450. As a result, a branch vessel 1100 is guided to a position between the first dissecting device 310 and the second dissecting device 320, and is flattened and thermally coagulated by the roller electrode 450, as illustrated in FIG. 38. When the second dissecting device 320 is further inserted, the thermally coagulated branch vessel 1100 is cut by the cutting section 430. According to this embodiment, the branch vessels 1100 can sequentially be thermally coagulated and cut.

According to this configuration, since the second dissecting device 320 functions also as the treating device 400, the branch vessel 1100 can be treated simultaneously with the insertion of the second dissecting device 320. Therefore, the dissection of the great saphenous vein 1000 (the first step) can be carried out smoothly.

By the eighth embodiment as above, also, the same or equivalent effects to those of the aforementioned first embodiment can be exhibited.

Figure 39:
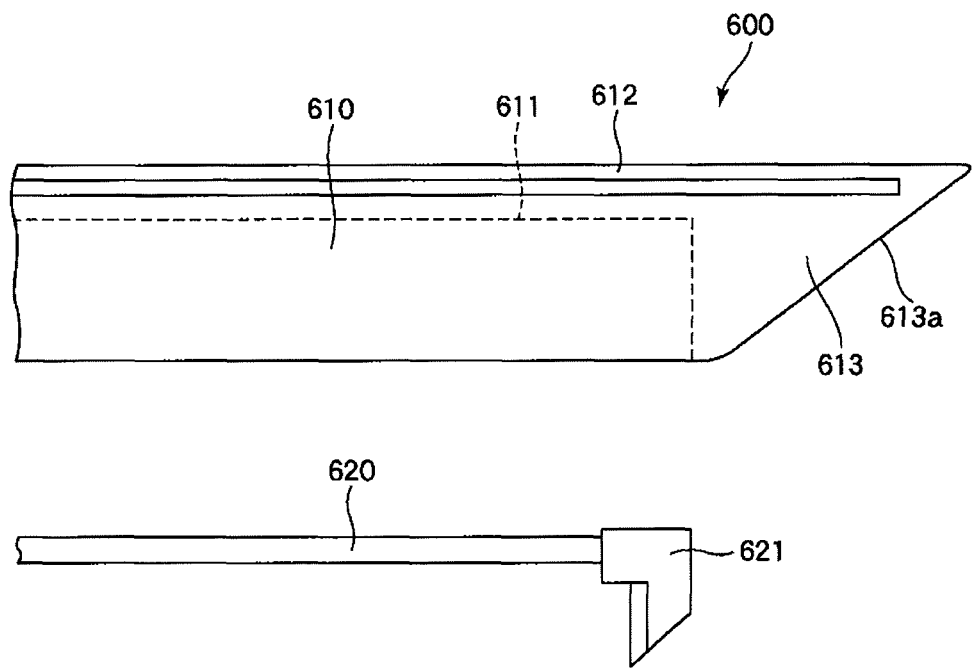
FIG. 39 is a lateral view of a cutting device possessed by a blood vessel dissecting device according to a ninth embodiment of the present disclosure.
Figure 40:
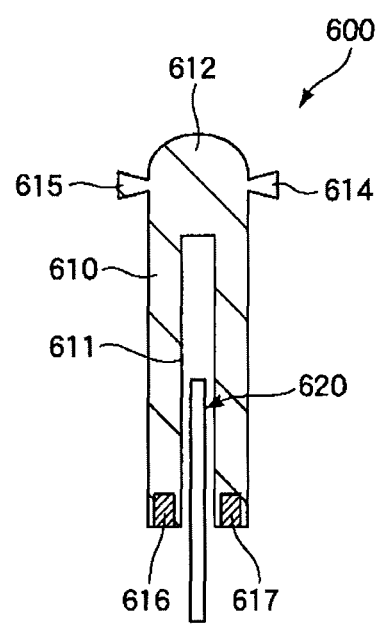
FIG. 40 is a sectional view of the cutting device depicted in FIG. 39.
Figure 41:
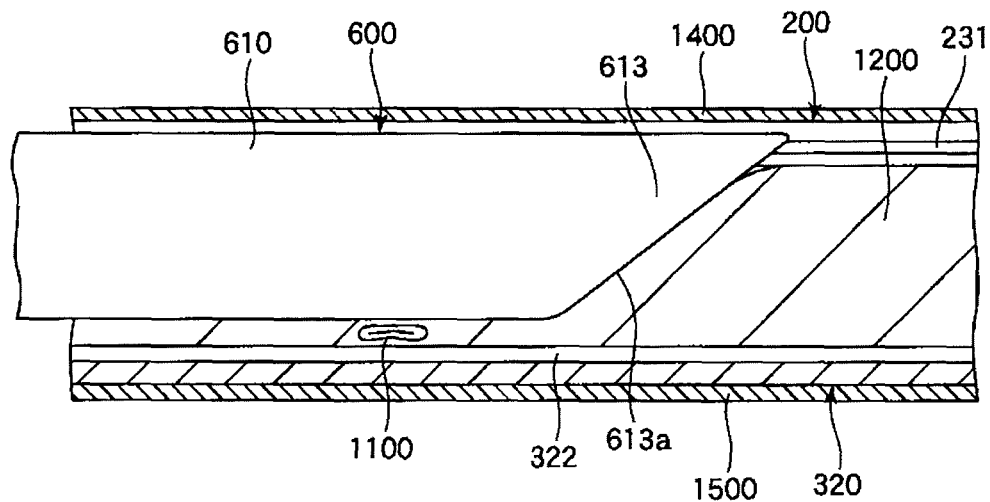
FIG. 41 illustrates a branch vessel treating method.
Figure 42:
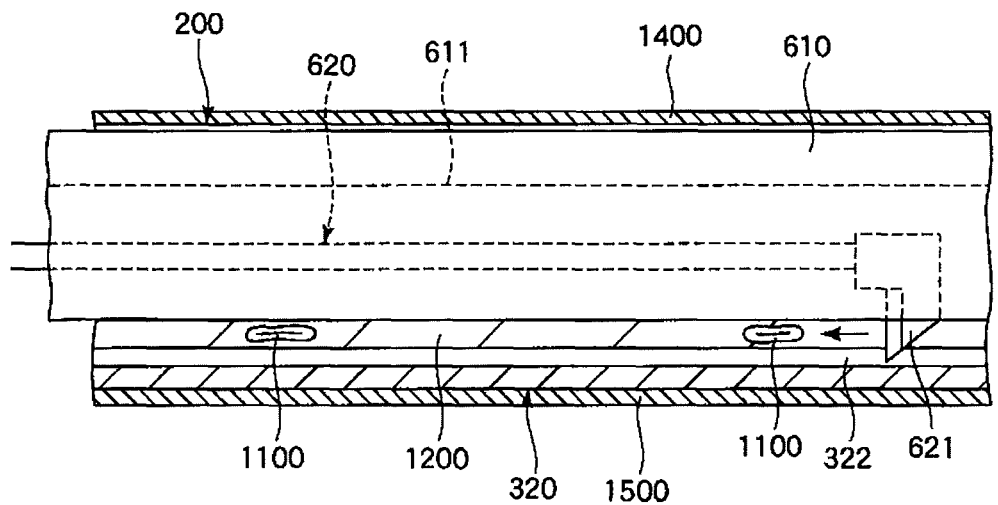
FIG. 42 illustrates the branch vessel treating method.

FIG. 39 is a lateral view of a cutting device possessed by a blood vessel dissecting device according to a ninth embodiment of the present disclosure. FIG. 40 is a sectional view of the cutting device depicted in FIG. 39. FIGS. 41 and 42 illustrate a branch vessel treating method.

In describing the ninth embodiment below referring to these figures, differences from the aforementioned embodiments will be described primarily, and descriptions of the same items as above will be omitted.

This embodiment is the same as the aforementioned first embodiment except mainly for a difference in the configuration of the cutting device.

As depicted in FIGS. 39 and 40, a cutting device 600 in this embodiment includes a main body section 610, and a cutting section 620 movable in the main body section 610.

In accordance with an exemplary embodiment, the main body section 610 is elongated plate-like in shape. In addition, the main body section 610 has a groove 611 opening on the lower side thereof. The groove 611 opens also at a proximal end of the main body section 610, to constitute an insertion hole for insertion of the cutting section 620. In addition, the main body section 610 has a protection section 612 provided on the upper side (one side in regard of the width direction) thereof. The protection section 612 extends in the axial direction of the main body section 610, and its peripheral surface is rounded. The protection section 612 exhibits a function equivalent to that of the protection section 541 possessed by the cutting device 500 in the aforementioned first embodiment.

In addition, the main body section 610 is provided at its distal portion with a guide portion 613. The guide portion 613 has a guide surface 613a inclined and facing downward, and has a function of guiding fat 1200 and branch vessels 1100 toward the lower side (between the groove 611 and a fascia-side dissecting device 300) by use of the guide surface 613a when the main body section 610 advances in a living body.

In addition, the main body section 610 has connection sections 614 and 615 capable of connection with rails 231 and 232 of a skin-side dissecting device 200. In addition, the main body section 610 is provided with electrodes 616 and 617, with the groove 611 therebetween. Specifically, for example, the electrode (first electrode) 616 is disposed on one side of the groove 611, whereas the electrode (second electrode) 617 is disposed on the other side of the groove 611.

On the other hand, the cutting section 620 can be inserted into the groove 611, and can be slid within the groove 611. In addition, a distal portion of the cutting section 620 is a cutting edge portion 621 which can protrude from the groove 611. Note that rails (stretches of recess) 312 and 322 possessed by the fascia-side dissecting device 300 function as grooves in which to insert the cutting edge portion 621 in this embodiment.

A treatment of a branch vessel 1100 by the cutting device 600 in this embodiment can include a step of dissecting fat 1200 along a great saphenous vein 1000, a step of pressing the dissected fat 1200, a step of cauterizing the branch vessel 1100 contained in the pressed fat 1200, and a step of cutting the cauterized branch vessel 1100.

Specifically, first, a skin-side dissecting device 200 and a fascia-side dissecting device 300 are inserted into a living body, and the fat 1200 present on the upper and lower sides of the great saphenous vein 1000 is dissected. Next, the connection section 614 is connected to the rail 231 of the skin-side dissecting device 200, and the main body section 610 is inserted into the living body while being guided by the skin-side dissecting device 200, whereon the fat 1200 and the branch vessel 1100 are guided by the guide portion 613 to between the main body section 610 and the second dissecting device 320, as depicted in FIG. 41. As a result, the fat 1200 and the branch vessel 1100 are sandwiched between the main body section 610 and the second dissecting device 320 in a flattened state (pressed (compressed) state). In this instance, the insertion is preferably performed while pressing the skin-side dissecting device 200 from the skin 1400 side and thereby pressing the main body section 610 against a second dissecting device 320. Next, a high-frequency alternating voltage is impressed between the electrodes 616 and 617, whereby the branch vessels 1100 held between the main body section 610 and the second dissecting device 320 are cauterized and thermally coagulated.

Subsequently, the cutting section 620 is inserted into the groove 611, and, as depicted in FIG. 42, the cutting edge portion 621 is protruded from the distal side of the groove 611 to enter into the rail 322 of the second dissecting device 320. Next, the cutting edge section 620 is slid toward the proximal side, whereby the branch vessels 1100 and the fat 1200 are cut by the cutting edge portion 621. By these operations, the fat 1200 present at a lateral side of the great saphenous vein 1000 is cut in the left-right direction, and the branch vessels 1100 are thermally coagulated and cut. Note that with the branch vessels 1100 and the fat 1200 held between the main body section 610 and the second dissecting device 320, displacement of them is restrained, and the treatment of them can be performed reliably. In addition, the fat 1200 held between the main body section 610 and the second dissecting device 320 is cauterized at the time of thermal coagulation of the branch vessels 1100 conducted precedingly, so that the cutting of the fat 1200 by the cutting edge portion 621 can be performed smoothly.

With the same operation as above conducted also on the opposite side (the first dissecting device 310 side), the fat 1200 surrounding the great saphenous vein 1000 is dissected over the entire circumference thereof, and the great saphenous vein 1000 is dissected in the state of being covered with the surrounding fat 1200.

According to the ninth embodiment configured in this manner, also, the same or equivalent effects to those of the aforementioned first embodiment can be produced.

Note that while the voltage is impressed between the electrodes 616 and 617 in the cutting device 600 in this embodiment, a configuration may be adopted wherein the pair of electrodes 616 and 617 are connected to be the same in potential so as to constitute the electrode (first electrode) on one side, whereas the cutting edge portion 621 of the cutting section 620 functions also as the electrode (second electrode) on the other side. In such a configuration, the main body section 610 is inserted into the living body, the cutting section 620 is inserted into the main body section 610, and thereafter the cutting section 620 is slid toward the proximal side while impressing a high-frequency alternating voltage between the electrodes 616 and 617 and the cutting edge portion 621, whereby the branch vessel 1100 can be thermally coagulated and cut. According to this configuration, a region in which an electric field is generated can be narrowed, so that the electric field can be made to effectively act on the branch vessel 1100, and the branch vessel 1100 can be reliably thermally coagulated.

In addition, while the fascia-side dissecting device 300 has the first dissecting device 310 and the second dissecting device 320 in this embodiment like in the aforesaid embodiments, the number of the dissecting devices possessed by the fascia-side dissecting device, for example, is not limited to this, and may be one or may be three or more.

Figure 43:
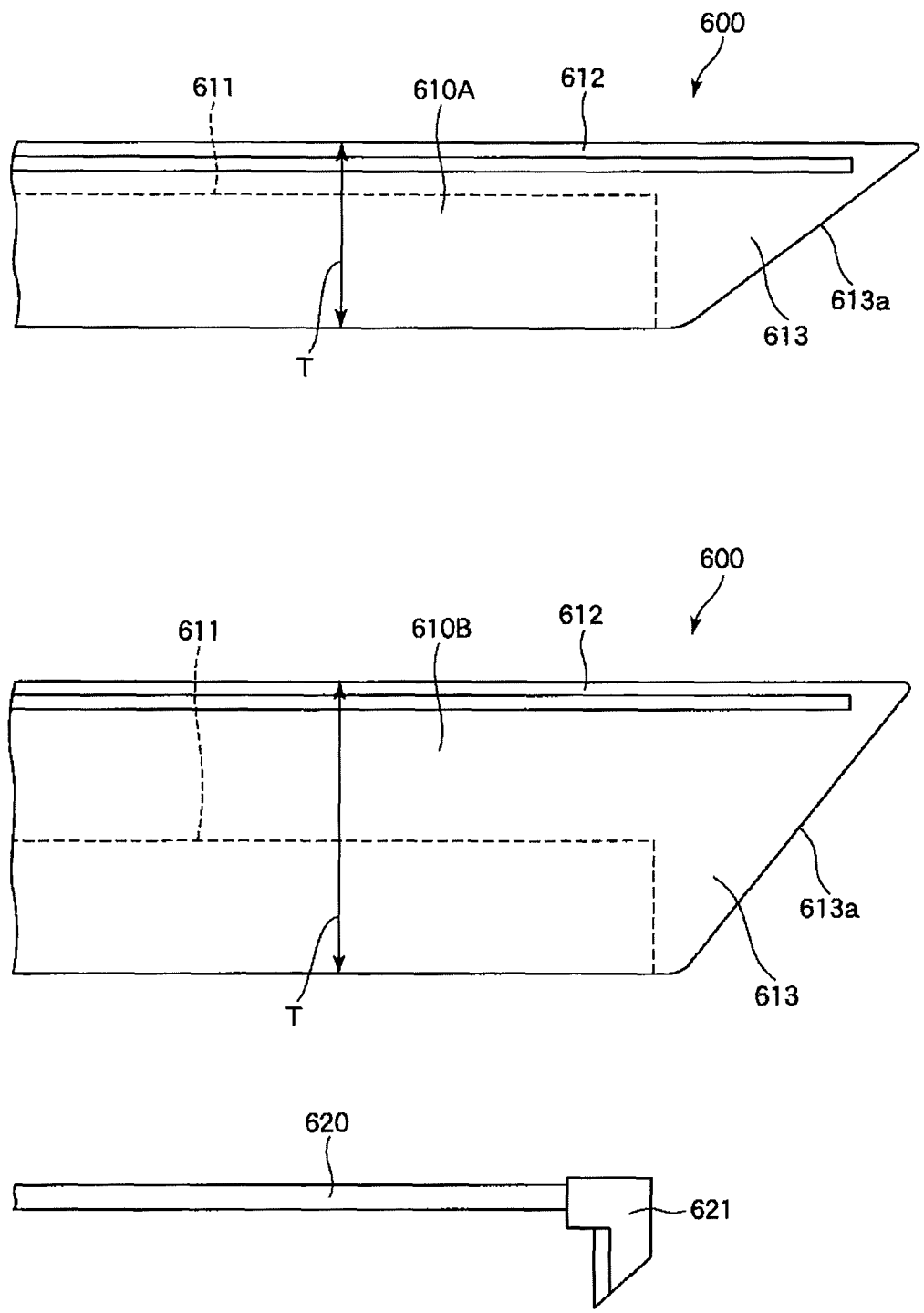
FIG. 43 is a lateral view of a cutting device possessed by a blood vessel dissecting device according to a tenth embodiment of the present disclosure.
Figure 44:
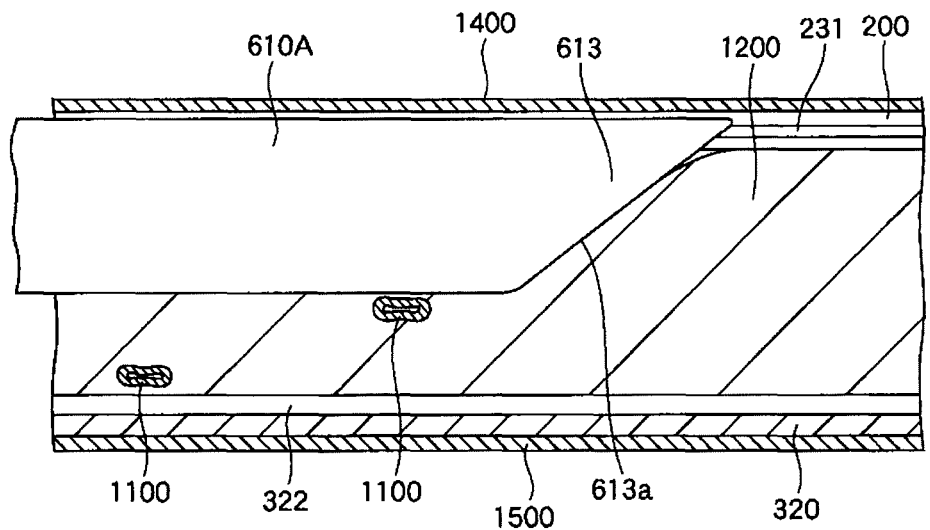
FIG. 44 illustrates a branch vessel treating method.
Figure 45:
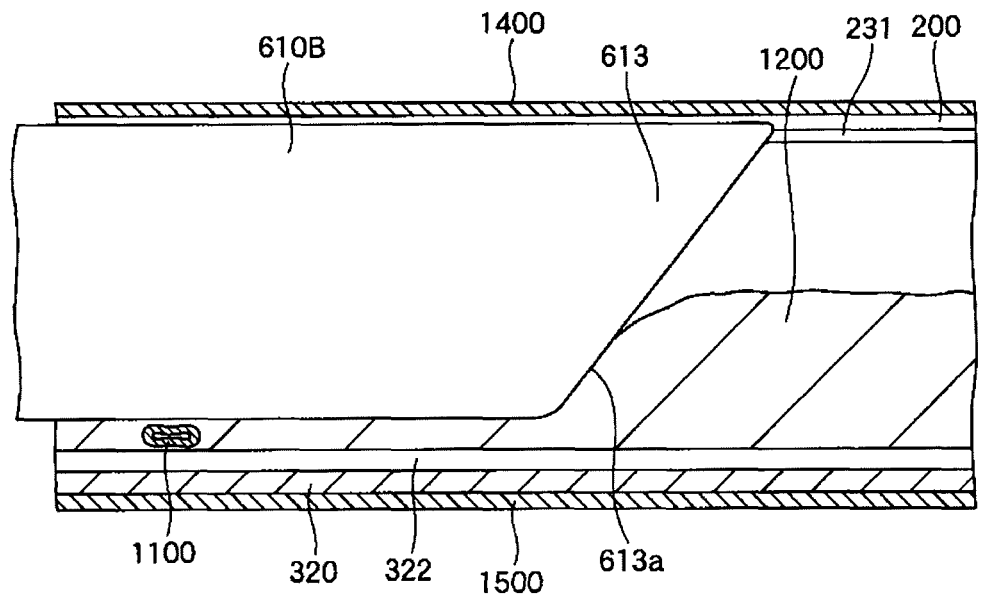
FIG. 45 illustrates the branch vessel treating method.

FIG. 43 is a lateral view of a cutting device possessed by a blood vessel dissecting device according to a tenth embodiment of the present disclosure. FIGS. 44 and 45 illustrate a branch vessel treating method.

In describing the tenth embodiment below referring to these figures, differences from the aforementioned embodiments will be described primarily, and descriptions of the same items as above will be omitted.

This embodiment is the same as the aforementioned ninth embodiment except mainly that the cutting device has a plurality of main body sections.

As depicted in FIG. 43, a cutting device 600 in this embodiment can include two main body sections 610A and 610B differing in thickness T, and a cutting section 620. The main body sections 610A and 610B are configured in the same manner as the main body section 610 in the aforementioned ninth embodiment. Note that while the two main body sections 610A and 610B are prepared in this embodiment, the number of the main body sections to be prepared is not limited to two, and may be three or more.

In the aforementioned ninth embodiment, for example, it is necessary for the fat 1200 and the branch vessel 1100 to be guided to between the main body section 610 and the fascia-side dissecting device 300 by a single inserting operation of the main body section 610. Depending on the separated distance between the skin-side dissecting device 200 and the fascia-side dissecting device 300, however, a situation may occur in which the fat 1200 to be guided to between the main body section 610 and the fascia-side dissecting device 300 is so thick that it cannot be guided appropriately or that even though it can be guided, an excessive force is needed for cutting the fat 1200 by the cutting section 620.

In view of such a problem, in this embodiment, the main body sections 610A and 610B differing in thickness T are prepared, and the fat 1200 and the branch vessel 1100 are cut by cutting two times, whereby the operation can be smoothly carried out without needing an excessive force. Specifically, first, as depicted in FIG. 44, the main body section 610A smaller in thickness T is inserted. Then, a high-frequency alternating voltage is impressed between electrodes 616 and 617 to thermally coagulate the branch vessel 1100, and thereafter the branch vessels 1100 and the fat 1200 are cut by use of the cutting section 620. It follows that the fat 1200 is cut to an intermediate position. Next, the main body section 610A is drawn out, after which the main body section 610B is inserted as depicted in FIG. 45. Then, a high-frequency alternating voltage is impressed between the electrodes 616 and 617 to thermally coagulate the branch vessel 1100, and thereafter the branch vessel 1100 and the fat 1200 are cut by use of the cutting section 620. By these operations, the fat 1200 present on a lateral side of a great saphenous vein 1000 is cut in the left-right direction, and the branch vessels 1100 are stanched and cut.

The same operation is conducted also on the opposite side (the first dissecting device 310 side), whereby the fat 1200 surrounding the great saphenous vein 1000 is dissected over the entire circumference thereof, and the great saphenous vein 1000 is dissected in the state of being covered with the surrounding fat 1200.

By the tenth embodiment as above, also, the same or equivalent effects to those of the aforementioned first embodiment can be exhibited.

Figure 46:
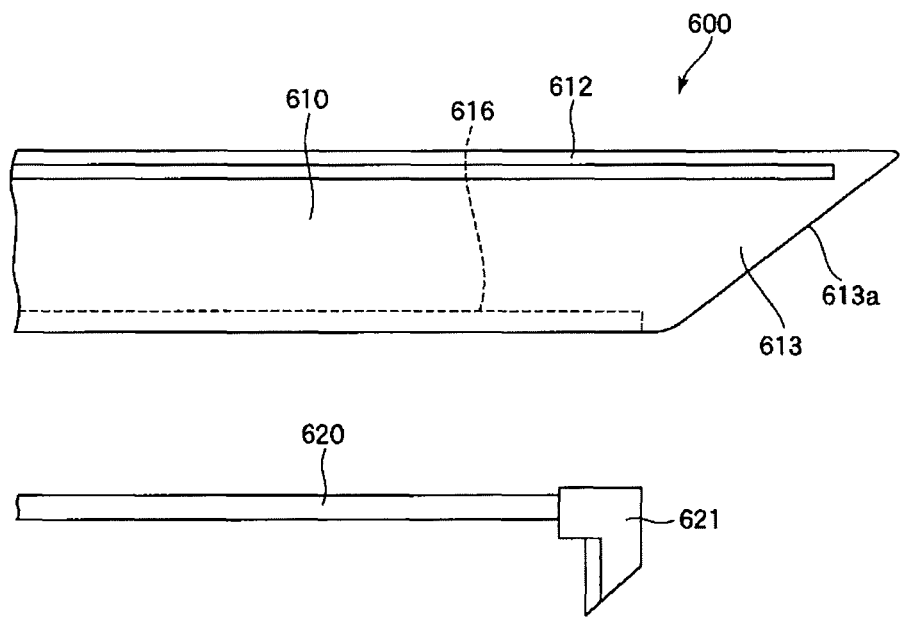
FIG. 46 is a lateral view of a cutting device possessed by a blood vessel dissecting device according to an eleventh embodiment of the present disclosure.
Figure 47:
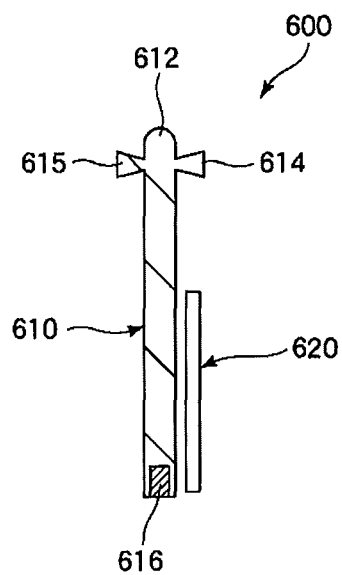
FIG. 47 is a sectional view of the cutting device depicted in FIG. 46.
Figure 48:
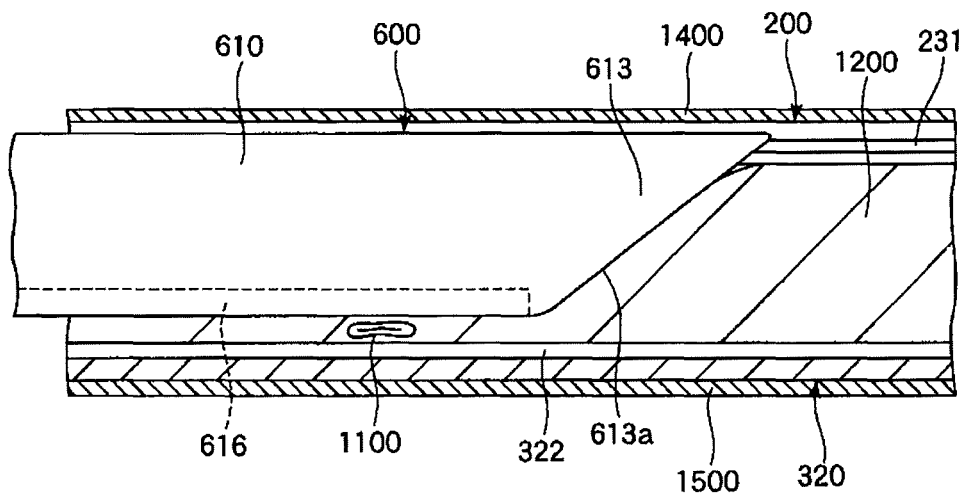
FIG. 48 illustrates a branch vessel treating method.
Figure 49:
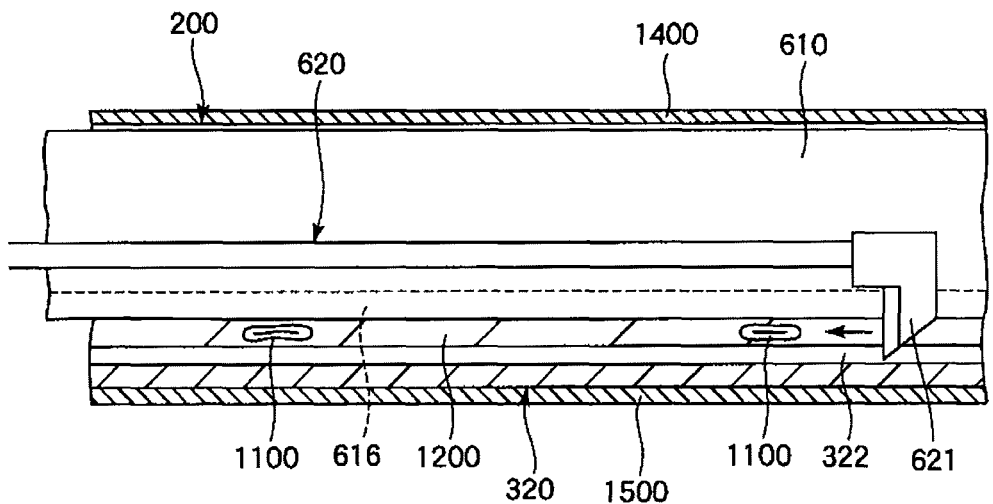
FIG. 49 illustrates the branch vessel treating method.

FIG. 46 is a lateral view of a cutting device possessed by a blood vessel dissecting device according to an eleventh embodiment of the present disclosure. FIG. 47 is a sectional view of the cutting device depicted in FIG. 46. FIGS. 48 and 49 illustrate a branch vessel treating method.

In describing the eleventh embodiment below referring to these figures, differences from the aforementioned embodiments will be described primarily, and descriptions of the same items as above will be omitted.

This embodiment is the same as the aforementioned ninth embodiment except mainly for a difference in the configuration of the cutting device.

As illustrated in FIGS. 46 and 47, a cutting device 600 in this embodiment can include a main body section 610, and a cutting section 620 moved along the main body section 610. The main body section 610 is elongated plate-like in shape. In addition, the main body section 610 is provided with an electrode (first electrode) 616 on a lower side thereof. On the other hand, the cutting section 620 is configured in substantially the same manner as in the aforementioned ninth embodiment, and a cutting edge portion 621 functions as an electrode (second electrode).

A treatment of a branch vessel 1100 by the cutting device 600 in this embodiment can include a step of dissecting fat 1200 along a great saphenous vein 1000, a step of pressing the dissected fat 1200, and a step of cauterizing and cutting the branch vessels 1100 contained in the pressed fat 1200.

Specifically, first, a skin-side dissecting device 200 and a fascia-side dissecting device 300 are inserted into a living body, and the fat 1200 present on the upper and lower sides of the great saphenous vein 1000 is dissected. Next, a connection section 614 is connected to a rail 231 of the skin-side dissecting device 200, and the main body section 610 is inserted into the living body while guiding it with the skin-side dissecting device 200. As a result, as depicted in FIG. 48, the fat 1200 and the branch vessels 1100 are guided to between the main body section 610 and a second dissecting device 320 by a guide portion 613, and clamped between them in a flattened state. Next, the cutting section 620 is inserted along a side surface of the main body section 610, and, as depicted in FIG. 49, a cutting edge portion 621 is protruded from a lower surface of the main body section 610 to enter into a rail 322 of a second dissecting device 320. Then, the cutting section 620 is slid toward the proximal side while impressing a high-frequency alternating voltage between the electrode 616 and the cutting edge portion 621, whereby the branch vessels 1100 are thermally coagulated and cut by the cutting section 620.

The same operation is conducted also on the opposite side (the first dissecting device 310 side), whereby the fat 1200 surrounding the great saphenous vein 1000 is dissected over the entire circumference thereof, and the great saphenous vein 1000 is dissected in the state of being covered with the surrounding fat 1200.

By the eleventh embodiment as above, also, the same or equivalent effects to those of the aforementioned first embodiment can be produced.

Figure 50:
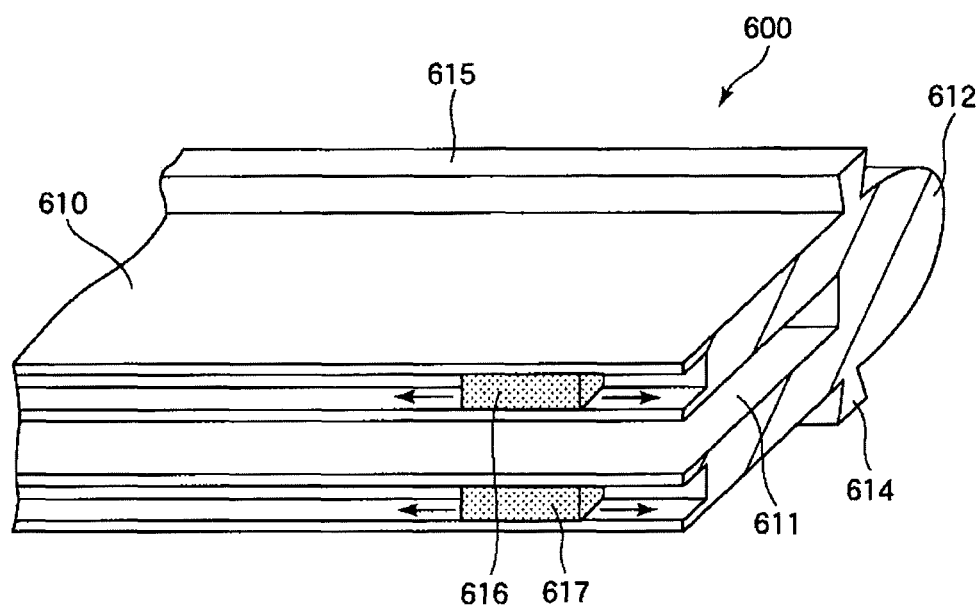
FIG. 50 is a perspective view of a cutting device possessed by a blood vessel dissecting device according to a twelfth embodiment of the present disclosure.
Figure 51:
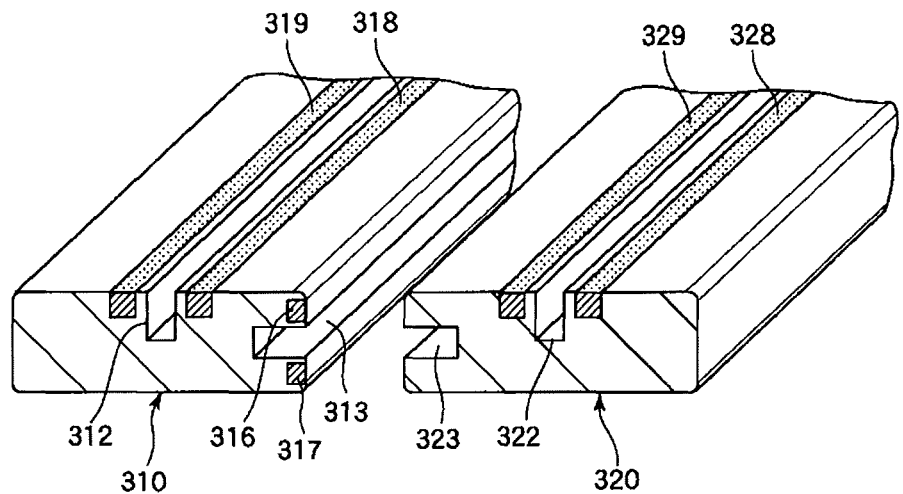
FIG. 51 is a perspective view of a fascia-side dissecting device possessed by the blood vessel dissecting device according to the twelfth embodiment of the present disclosure.
Figure 52:
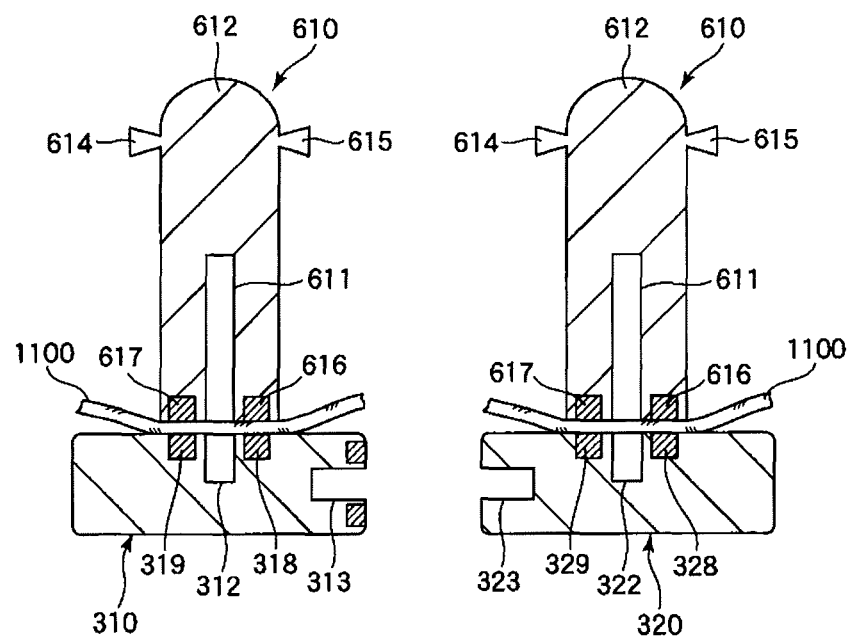
FIG. 52 is a sectional view depicting a state in which the cutting device and the fascia-side dissecting device are made to face each other.
Figure 53:
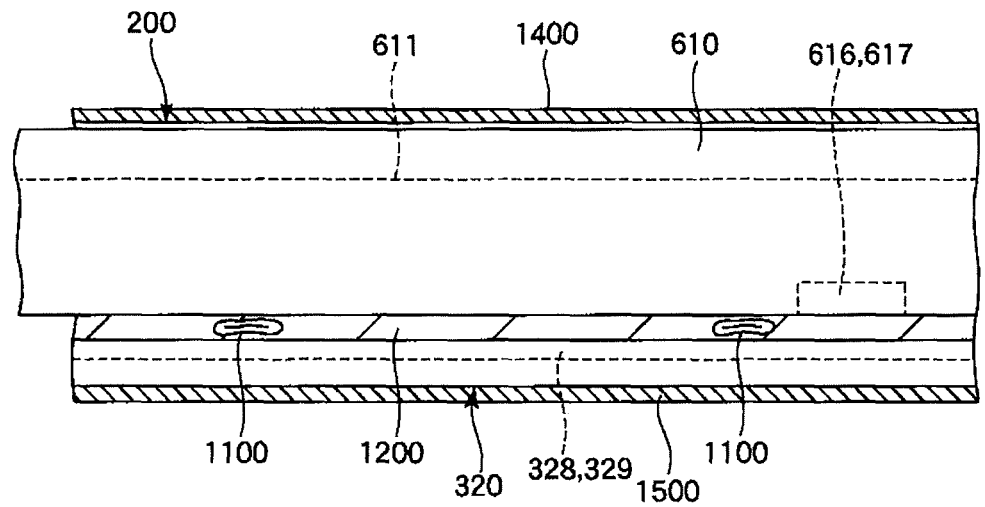
FIG. 53 illustrates a branch vessel treating method.
Figure 54:
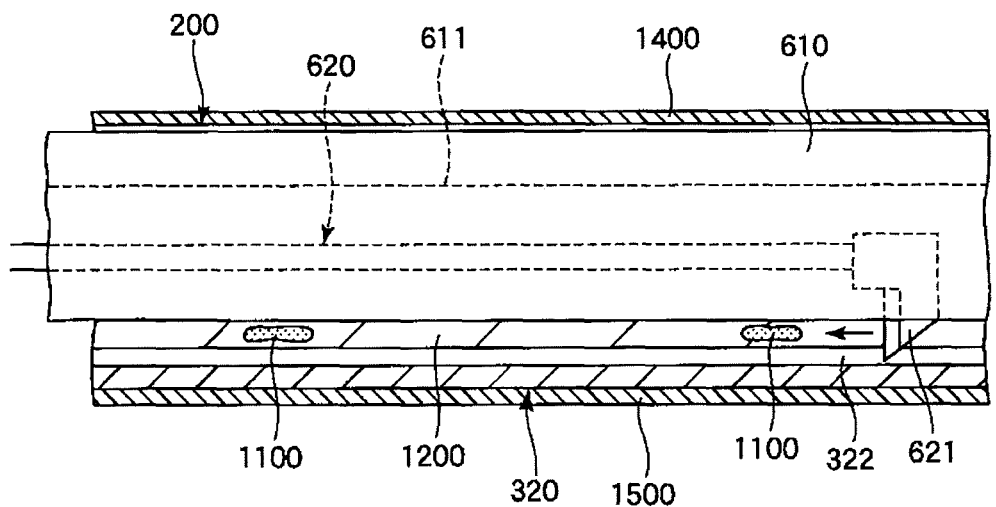
FIG. 54 illustrates the branch vessel treating method.

FIG. 50 is a perspective view of a cutting device possessed by a blood vessel dissecting device according to a twelfth embodiment of the present disclosure. FIG. 51 is a perspective view of a fascia-side dissecting device possessed by the blood vessel dissecting device according to the twelfth embodiment. FIG. 52 is a sectional view illustrating a state where the cutting device and the fascia-side dissecting device are set facing each other. FIGS. 53 and 54 illustrate a branch vessel treating method.

In describing the twelfth embodiment below referring to these figures, differences from the aforementioned embodiments will be described primarily, and descriptions of the same items as above will be omitted.

This embodiment is the same as the aforementioned ninth embodiment except mainly for differences in the configurations of the cutting device and the fascia-side dissecting device.

As illustrated in FIG. 50, in a main body section 610 of a cutting device 600 in this embodiment, electrodes (first electrodes) 616 and 617 are formed to be shorter than those in the aforementioned ninth embodiment. In addition, the electrodes 616 and 617 are integrally movable in the axial direction relative to a main body section 610. In addition, the electrodes 616 and 617 are connected to be the same in potential. Note that the length of the electrodes 616 and 617 is not particularly limited, and may be, for example, approximately 5 mm to 2 cm.

On the other hand, as depicted in FIG. 51, a first dissecting device 310 has electrodes (second electrodes) 318 and 319 disposed to face each other, with a rail 312 therebetween. In addition, the electrodes 318 and 319 extend in the axial direction of the first dissecting device 310. In addition, as depicted in FIG. 52, the electrodes 318 and 319 face the electrodes 616 and 617 when the first dissecting device 310 and the main body section 610 are disposed with the groove 611 and the rail 312 facing each other. Similarly, a second dissecting device 320 has electrodes (second electrodes) 328 and 329 disposed to face each other, with a rail 322 therebetween. In addition, the electrodes 328 and 329 extend in the axial direction of the second dissecting device 320. In addition, the electrodes 328 and 329 face the electrodes 616 and 617 when the second dissecting device 320 and the main body section 610 are disposed with the groove 611 and the rail 322 facing each other.

In such a configuration, first, the main body section 610 is inserted into a living body, and a state is obtained in which fat 1200 and branch vessels 1100 are clamped between the main body section 610 and the second dissecting device 320. Next, as depicted in FIG. 53, the electrodes 616 and 617 are slid relative to the main body section 610 while impressing a high-frequency alternating voltage between the electrodes 616 and 617 and the electrodes 328 and 329, thereby thermally coagulating the branch vessels 1100. Subsequently, as depicted in FIG. 54, the thermally coagulated branch vessels 1100 are cut by a cutting section 620.

The same operation is conducted also on the opposite side (the first dissecting device 310 side), whereby the fat 1200 surrounding a great saphenous vein 1000 is dissected over the entire circumference thereof, and the great saphenous vein 1000 is dissected in the state of being covered with the surrounding fat 1200.

By the twelfth embodiment as above, also, the same or equivalent effects to those of the aforementioned first embodiment can be produced.

Figure 55:
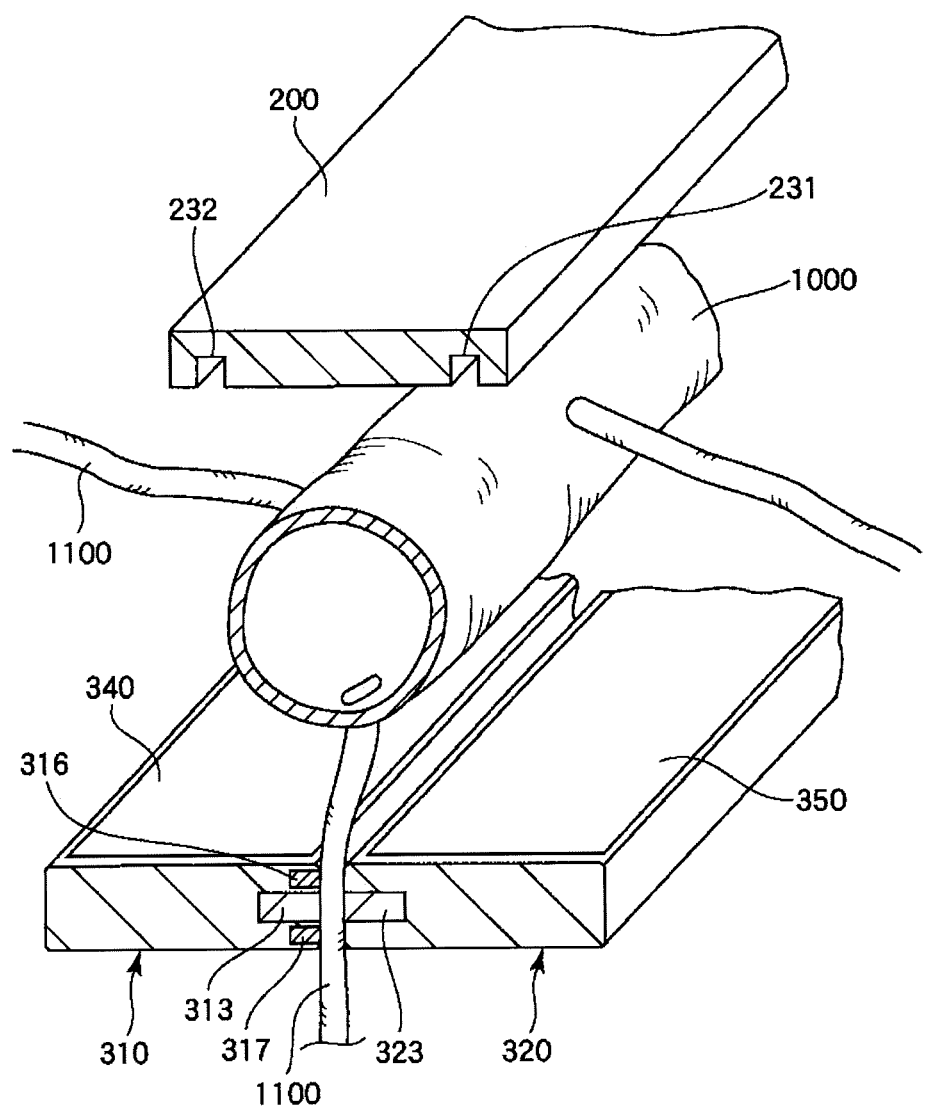
FIG. 55 is a perspective view of a skin-side dissecting device and a fascia-side dissecting device possessed by a blood vessel dissecting device according to a thirteenth embodiment of the present disclosure.
Figure 56:
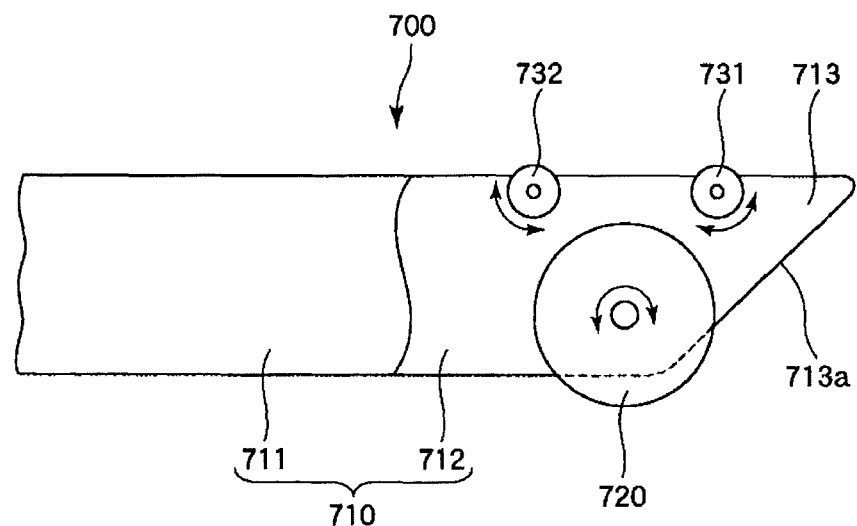
FIG. 56 is a lateral view of a cutting device possessed by the blood vessel dissecting device according to the thirteenth embodiment of the present disclosure.
Figure 57:
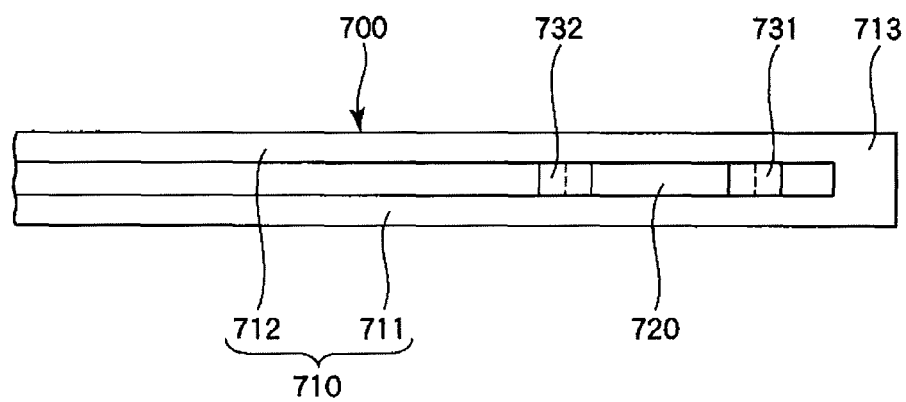
FIG. 57 is a top plan view of the cutting device depicted in FIG. 56.
Figure 58:
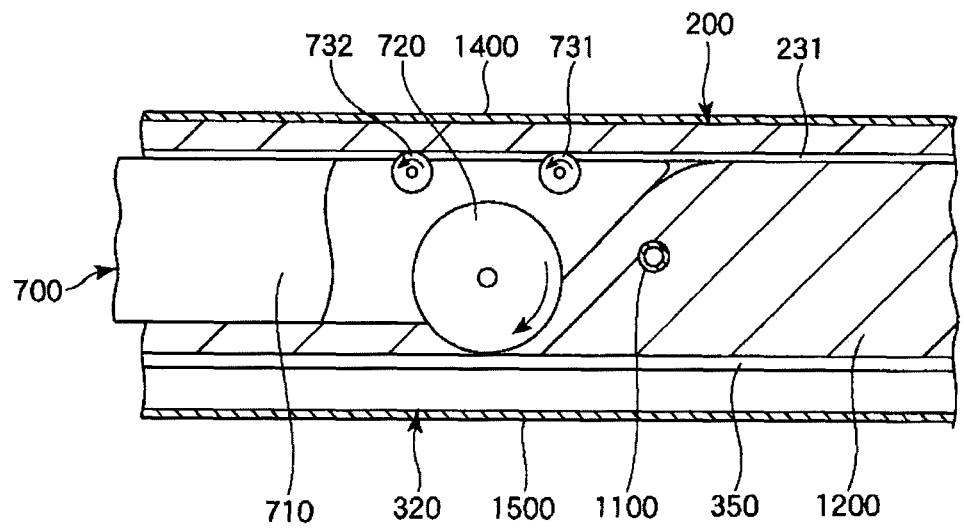
FIG. 58 illustrates a branch vessel treating method.
Figure 59:
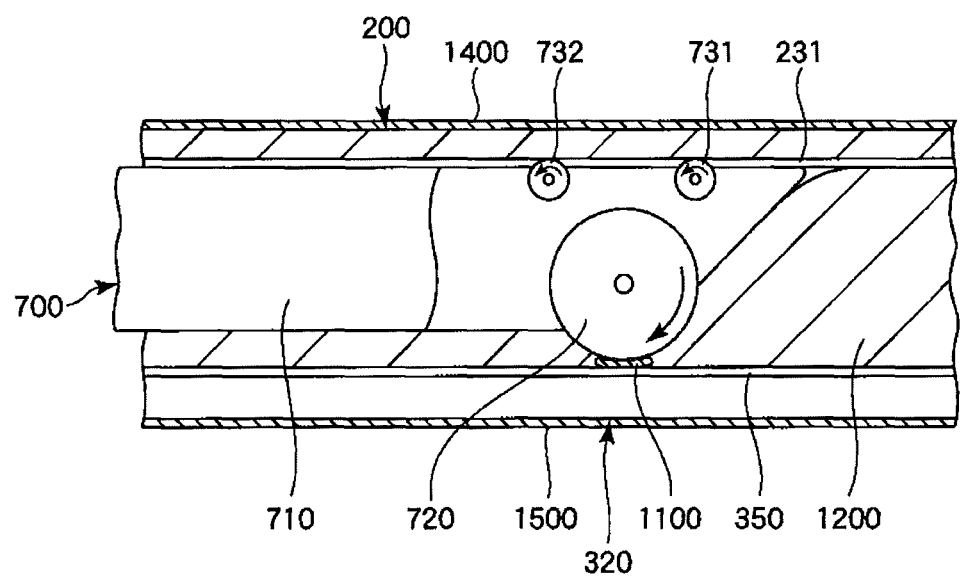
FIG. 59 illustrates the branch vessel treating method.

FIG. 55 is a perspective view of a skin-side dissecting device and a fascia-side dissecting device possessed by a blood vessel dissecting device according to a thirteenth embodiment of the present disclosure. FIG. 56 is a lateral view of a cutting device possessed by the blood vessel dissecting device according to the thirteenth embodiment. FIG. 57 is a top plan view of the cutting device depicted in FIG. 56. FIGS. 58 and 59 illustrate a branch vessel treating method.

In describing the thirteenth embodiment below referring to these figures, differences from the aforementioned embodiments will be described primarily, and descriptions of the same items as above will be omitted.

This embodiment is the same as the aforementioned first embodiment except mainly for a difference in the configuration of the cutting device.

As depicted in FIG. 55, a skin-side dissecting device 200 in this embodiment has a substantially rectangular cross-sectional shape with, for example, rounded corners. In addition, rails 231 and 232 are provided in a lower surface of the skin-side dissecting device 200.

In addition, a first dissecting device 310 in this embodiment has a configuration obtained by omitting the rail 312 and, instead, providing an electrode (first electrode) 340 at an upper surface, as compared to the configuration in the aforementioned first embodiment. Similarly, a second dissecting device 320 in this embodiment has a configuration obtained by omitting the rail 322 and, instead, providing an electrode (first electrode) 350 at the upper surface, as compared to the configuration in the aforementioned first embodiment.

In addition, as depicted in FIGS. 56 and 57, a cutting device 700 in this embodiment can include an elongated main body section (guide device) 710, and a roller electrode (second electrode) 720 and rollers 731 and 732 which are rotatably provided on the main body section 710.

The main body section 710 has such a shape that the roller electrode 720 and the rollers 731 and 732 are held from both sides by two plate-shaped pieces 711 and 712. In addition, the main body section 710 is provided at its distal portion with a tapered guide portion 713. The guide portion 713 has a guide surface 713a inclined to face downward, and has a function of guiding fat 1200 and branch vessels 1100 toward the lower side (between the main body section 710 and a fascia-side dissecting device 300) by use of the guide surface 713a when the main body section 710 advances in a living body.

The roller electrode 720 is provided to protrude to the lower side of the main body section 710. In addition, the roller electrode 720 is provided to protrude from the guide portion 713 (guide surface 713a). Such a roller electrode 720 is an electrode for cauterizing the branch vessels 1100 and the fat 1200 guided to between the main body section 710 and the fascia-side dissecting device 300 by the guide portion 713 by the action of an electric field, and functions also as a cutting section for cutting the cauterized branch vessels 1100 and fat 1200. Note that the cutting section may be provided separately from the roller electrode 720. In that case, the cutting section may be disposed to protrude to the lower side of the main body section 710 at a position on the more proximal side than the roller electrode 720.

The rollers 731 and 732 are provided to protrude to the upper side of the main body section 710. When the main body section 710 is inserted into the living body, the rollers 731 and 732 engage with rails 231 and 232 of a skin-side dissecting device 200, whereby the cutting device 700 can be smoothly inserted into the living body.

In accordance with an exemplary embodiment, a treatment of the branch vessels 1100 by the cutting device 600 in this embodiment can include a step of dissecting the fat 1200 along a great saphenous vein 1000, a step of pressing the dissected fat 1200, a step of cauterizing the branch vessels 1100 contained in the pressed fat 1200, and a step of cutting the cauterized branch vessels 1100.

Specifically, first, the skin-side dissecting device 200 and the fascia-side dissecting device 300 are inserted into the living body, and fat 1200 present on the upper and lower sides of a great saphenous vein 1000 is thereby dissected. Next, while impressing a high-frequency alternating voltage between the electrode 350 and the roller electrode 720, the cutting device 700 is inserted between the skin-side dissecting device 200 and the second dissecting device 320, as depicted in FIG. 58. In this instance, the insertion is preferably conducted while pressing the skin-dissecting device 200 from the skin 1400 side and thereby pressing the cutting device 700 against the second dissecting device 320. As a result, the branch vessels 1100 and the fat 1200 are guided to between the main body section 710 and the second dissecting device 320 in a flattened state (pressed (compressed) state) by the guide portion 713, and are cauterized, thermally coagulated and are cut when passing between the roller electrode 720 and the second dissecting device 320 (electrode 350), as depicted in FIG. 59. In this way, with the branch vessels 1100 and the fat 1200 passed between the roller electrode 720 and the electrode 350, an electric field can be made to act thereon more effectively, whereby they can be cauterized sufficiently.

Particularly, as aforementioned, the branch vessels 1100 are cauterized in a flattened state, so that the branch vessels 1100 can be thermally coagulated more reliably. In addition, since the roller electrode 720 is rotatable, the branch vessels 1100 and the fat 1200 can be smoothly passed between the roller electrode 720 and the second dissecting device 320, so that the aforesaid operation can be carried out smoothly. Further, with the main boy section 710 provided with the roller electrode 720 as an electrode on one side, and with the second dissecting device 320 (first dissecting device 310) provided with the electrode 350 (electrode 340) as an electrode on the other side, the branch vessels 1100 and the fat 1200 can be passed between the roller electrode 720 and the electrode 350 (electrode 340) while adopting a comparatively simple configuration.

Note that while the timing of thermal coagulation of the branch vessels 1100 and the timing of cutting of the branch vessels 1100 are coincident in this embodiment, the thermal coagulation may be performed after the cutting, or the cutting may be performed after the thermal coagulation, as required.

The same operation is conducted also on the opposite side (the first dissecting device 310 side), whereby the fat 1200 surrounding the great saphenous vein 1000 is dissected over the entire circumference thereof, and the great saphenous vein 1000 is dissected in the state of being covered with the surrounding fat 1200.

By the thirteenth embodiment as above, also, the branch vessels 1100 and fat 1200 which are present on the left and right sides of the great saphenous vein 1000 can be treated easily.

Note that while the electrode 340 is disposed over the whole area of the upper surface of the first dissecting device 310 in this embodiment, the disposition of the electrode 340 is not particularly restricted so long as the branch vessels 1100 can be cauterized (thermally coagulated) by the electric field generated between the electrode 340 and the roller electrode 720. For example, the electrode 340 may be disposed in the form of a plurality of lines, or may be disposed in a tortuous shape according to the shape (state of extension) of the great saphenous vein 1000. In that case, it can be preferable that the rails 231 and 232 of the skin-side dissecting device 200 are also disposed in a tortuous shape.

Figure 60:
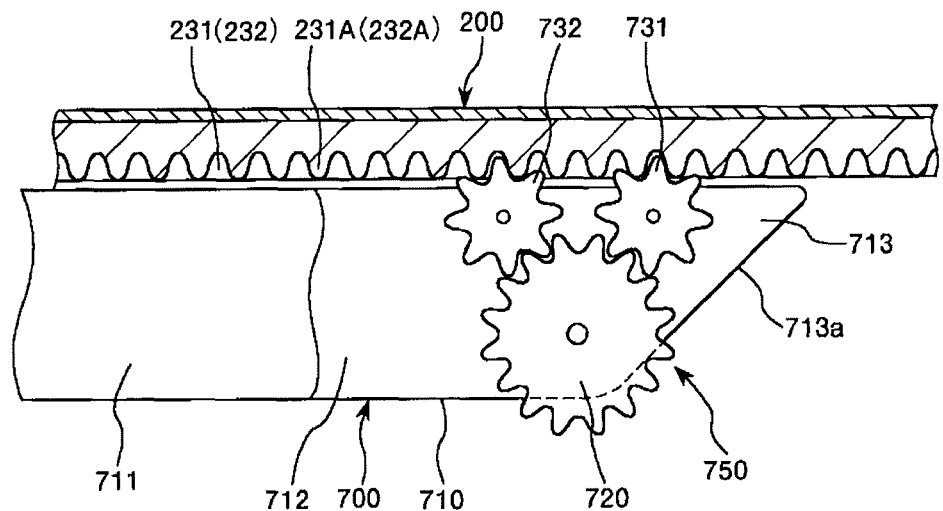
FIG. 60 is a lateral view of a skin-side dissecting device and a cutting device possessed by a blood vessel dissecting device according to a fourteenth embodiment of the present disclosure.
Figure 61:
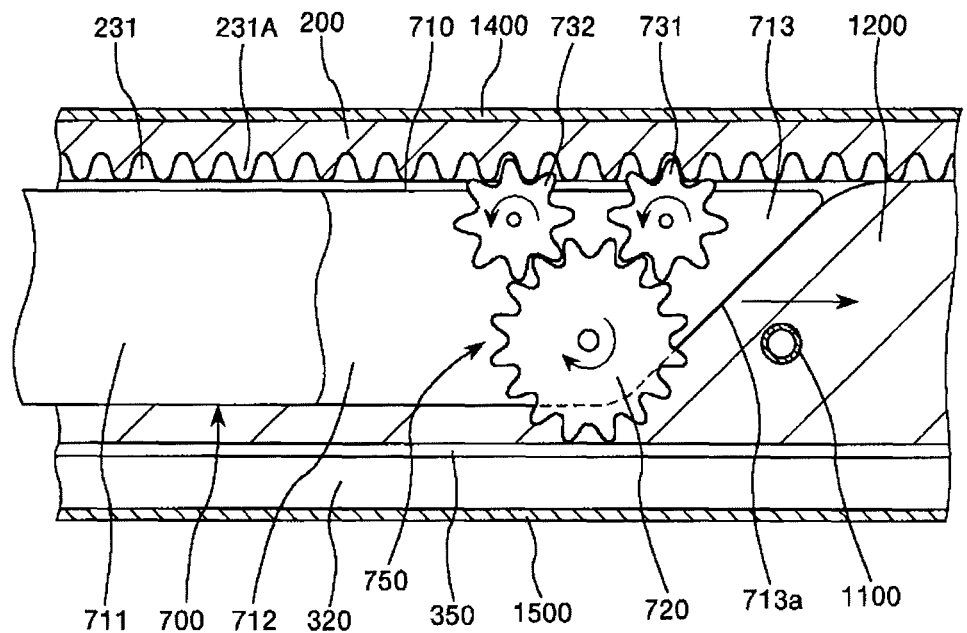
FIG. 61 illustrates a branch vessel treating method.

FIG. 60 is a lateral view of a skin-side dissecting device and a cutting device possessed by a blood vessel dissecting device according to a fourteenth embodiment of the present disclosure. FIG. 61 illustrates a branch vessel treating method.

In describing the fourteenth embodiment below referring to these figures, differences from the aforementioned embodiments will be described primarily, and description of the same items as above will be omitted.

This embodiment is the same as the aforementioned thirteenth embodiment except mainly for differences in the configurations of the skin-side dissecting device and the cutting device.

As depicted in FIG. 60, a skin-side dissecting device 200 in this embodiment includes a rack gear 231A rectilinearly gear-cut in a bottom surface of a rail 231, and a rack gear 232A also rectilinearly gear-cut in a bottom surface of a rail 232.

In addition, a cutting device 700 in this embodiment has rollers 731 and 732 having peripheral surfaces toothed to constitute pinion gears, which can mesh with the rails 231 and 232. Similarly, a roller electrode (rotating body) 720 also includes a pinion gear, which is in mesh with the rollers 731 and 732. The rollers 731 and 732 and the roller electrode 720 configured in this way constitute a guiding section 750 by which branch vessels 1100 and fat 1200 are positively guided to between a main body section 710 and a second dissecting device 320. With the roller electrode 720 thus functioning also as a rotating body, the configuration of the cutting device 700 can be simplified.

In such a configuration, as depicted in FIG. 61, when the cutting device 700 is inserted into a living body with the rollers 731 and 732 in mesh with the rail 231 of the skin-side dissecting device 200, the rollers 731 and 732 are rotated, and, further, the roller electrode 720 is rotated attendant on the rotation of the rollers 731 and 732. The roller electrode 720 is rotated in such a manner as to bias the branch vessels 1100 and the fat 1200 toward the rear side in regard of the inserting direction, in other words, in such a manner as to guide the branch vessels 1100 and the fat 1200 to between the main body section 710 and the second dissecting device 320. Therefore, the branch vessels 1100 and the fat 1200 can be positively guided to between the main body section 710 and the second dissecting device 320. Particularly, since the roller electrode 720 is provided to protrude from a guide portion 713 (guide surface 713*a*), the aforesaid effect is exhibited more conspicuously. In addition, since the friction with the fat 1200 is enhanced by the teeth provided at the peripheral surface of the roller electrode 720, the aforesaid effect can be enhanced.

The same operation is conducted also on the opposite side (the first dissecting device 310 side), whereby the fat 1200 surrounding a great saphenous vein 1000 is dissected over the entire circumference thereof, and the great saphenous vein 1000 is dissected in the state of being covered with the surrounding fat 1200.

By the fourteenth embodiment as above, also, the branch vessels 1100 and fat 1200 which are present on the left and right sides of the great saphenous vein 1000 can be easily treated.

Figure 62:
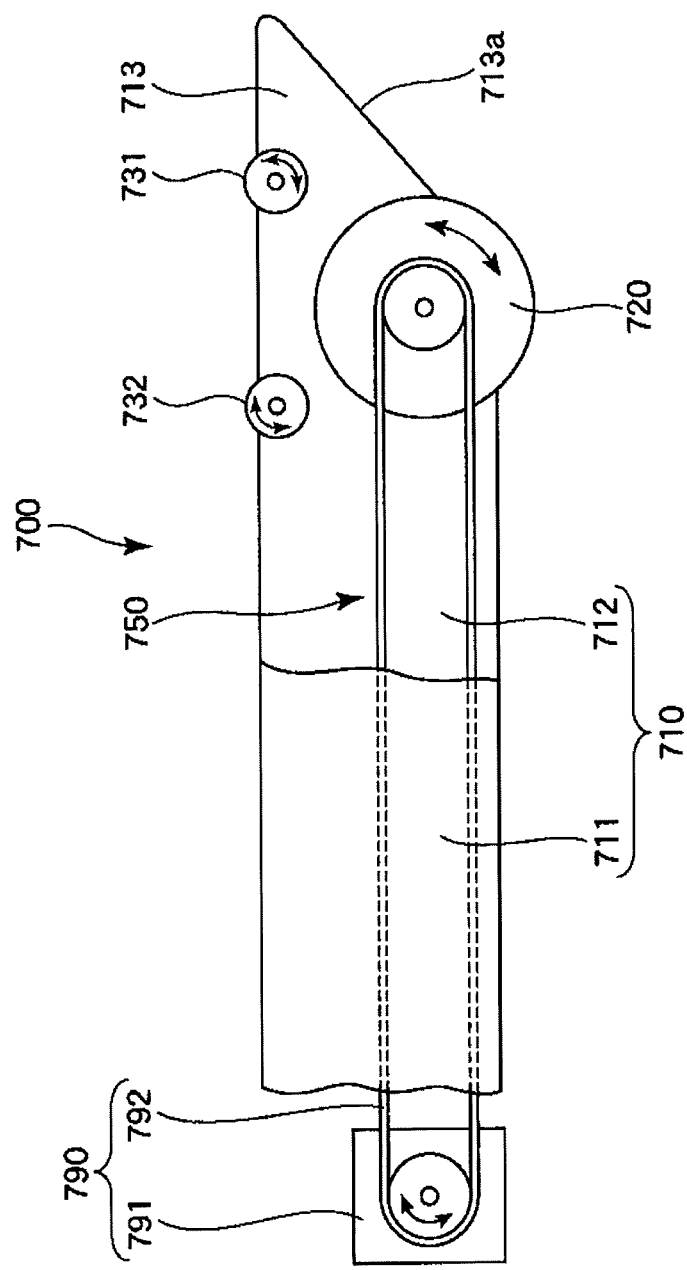
FIG. 62 is a lateral view of a cutting device possessed by a blood vessel dissecting device according to a fifteenth embodiment of the present disclosure.

FIG. 62 is a lateral view of a cutting device possessed by a blood vessel dissecting device according to a fifteenth embodiment of the present disclosure.

In describing the fifteenth embodiment below referring to this figure, differences from the aforementioned embodiments will be described primarily, and descriptions of the same items as above will be omitted.

This embodiment is the same as the aforementioned thirteenth embodiment except mainly for a difference in the configuration of the cutting device.

As illustrated in FIG. 62, a cutting device 700 in this embodiment has a driving section 790 for rotating a roller electrode (rotating body) 720. The driving section 790 can include a drive source 791 such as a motor, and an endless belt 792 for transmitting power generated from the drive source 791 to the roller electrode 720, wherein the rotation of the drive source 791 rotates the roller electrode 720. The roller electrode 720 and the driving section 790 constitute a guiding section 750. Note that the configuration of the driving section 790 is not specifically restricted so long as the roller electrode 720 can be rotated thereby.

In such a configuration, while the roller electrode 720 is rotated by the driving section 790 in such a direction that branch vessels 1100 and fat 1200 are guided to between a main body section 710 and a second dissecting device 320, the cutting device 700 is inserted into the living body. By this, the branch vessels 1100 and the fat 1200 can be guided to between the main body section 710 and the second dissecting device 320 in a more positive manner.

By the fifteenth embodiment as above, also, the branch vessels 1100 and fat 1200 present on the left and right sides of the great saphenous vein 1000 can be easily treated.

Figure 63:
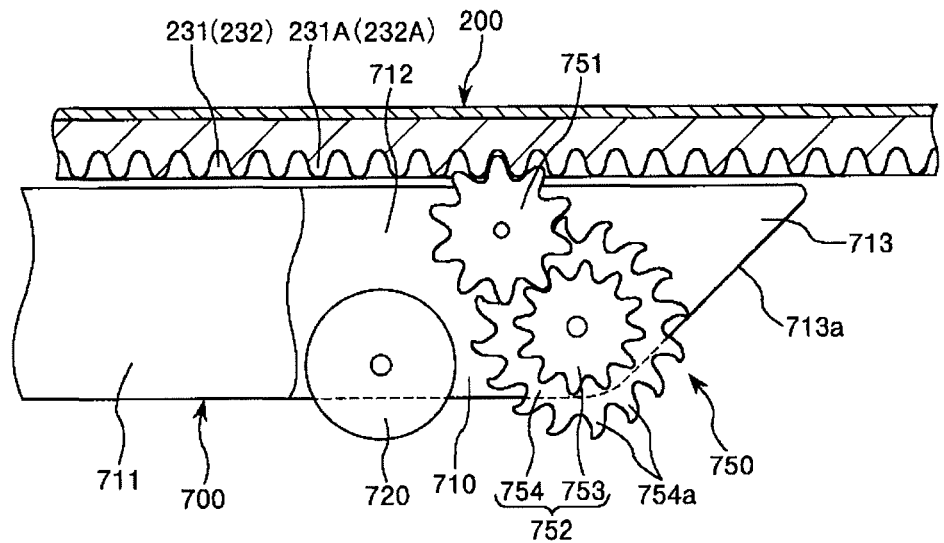
FIG. 63 is a lateral view of a skin-side dissecting device and a cutting device possessed by a blood vessel dissecting device according to a sixteenth embodiment of the present disclosure.
Figure 64:
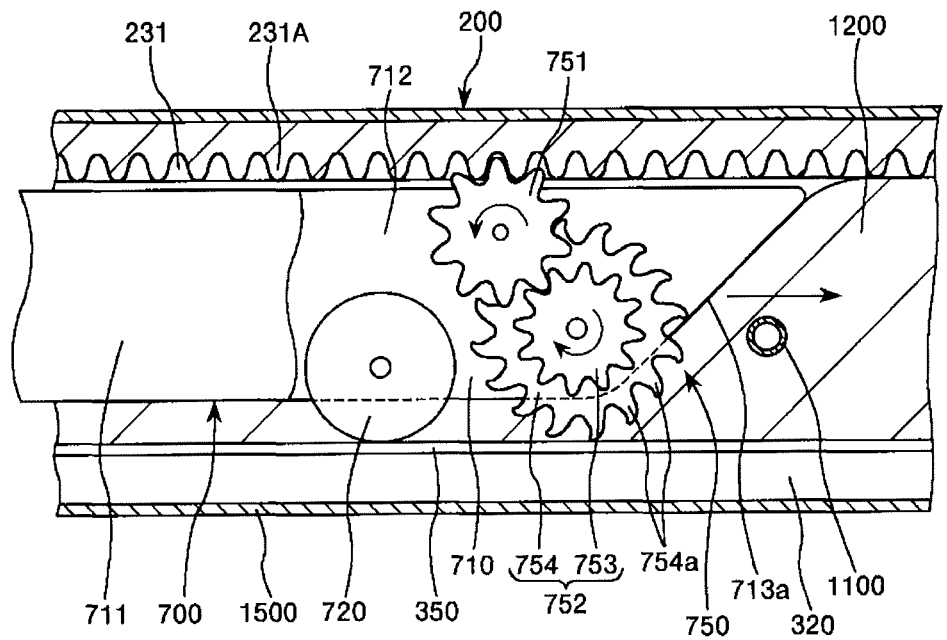
FIG. 64 illustrates a branch vessel treating method.

FIG. 63 is a lateral view of a skin-side dissecting device and a cutting device possessed by a blood vessel dissecting device according to a sixteenth embodiment of the present disclosure. FIG. 64 illustrates a branch vessel treating method.

In describing the sixteenth embodiment below referring to these figures, differences from the aforementioned embodiments will be described primarily, and descriptions of the same items as above will be omitted.

This embodiment is the same as the aforementioned thirteenth embodiment except mainly for differences in the configurations of the skin-side dissecting device and the cutting device.

A skin-side dissecting device 200 in this embodiment is configured in the same manner as that in the aforementioned fourteenth embodiment described.

A cutting device 700 in this embodiment has a guiding section 750 by which branch vessels 1100 and fat 1200 are positively guided to between a main body section 710 and a second dissecting device 320. As depicted in FIG. 63, the guiding section 750 can include a first gear portion 751 which is rotatably provided on the main body section 710 and in mesh with rails 231 and 232, and a second gear portion 752 which is rotatably provided on the main body section 710 and in mesh with the first gear portion 751. In addition, the second gear portion 752 can include a small-diameter part 753 in mesh with the first gear portion 751, and a large-diameter part 754 provided coaxially with the small-diameter part 753, wherein claw portions 754*a* are alignedly provided at a peripheral surface of the large-diameter part 754. The claw portions 754*a* protrude from a guide surface 713*a* of a guide portion 713.

In such a configuration, while a high-frequency alternating voltage is impressed between a roller electrode 720 and an electrode 350, the cutting device 700 is inserted into a living body with the first gear portion 751 in mesh with the rail 231 of the skin-side dissecting device 200, as depicted in FIG. 64, whereon the second gear portion 752 is rotated in such a manner as to bias the branch vessels 1100 and the fat 1200 toward the rear side in regard of the inserting direction, in other words, in such a manner as to guide the branch vessels 1100 and the fat 1200 to between the main body section 710 and the second dissecting device 320. Therefore, the branch vessels 1100 and the fat 1200 can be positively guided to between the main body section 710 and the second dissecting device 320. In addition, since friction with the fat 1200 is enhanced by the claw portions 754a provided at the peripheral surface of the second gear portion 752, the aforesaid effect is enhanced more. Then, the branch vessels 1100 and the fat 1200 guided to between the main body section 710 and the second dissecting device 320 are cauterized and cut when passing between the roller electrode 720, which is located on the rear side of the second gear portion 752, and the second dissecting device 320 (electrode 350).

The same operation is conducted also on the opposite side (the first dissecting device 310 side), whereby the fat 1200 surrounding a great saphenous vein 1000 is dissected over the entire circumference thereof, and the great saphenous vein 1000 is dissected in the state of being covered with the surrounding fat 1200.

By the sixteenth embodiment as above, also, the branch vessels 1100 and fat 1200 present on the left and right sides of the great saphenous vein 1000 can be easily treated.

Figure 65:
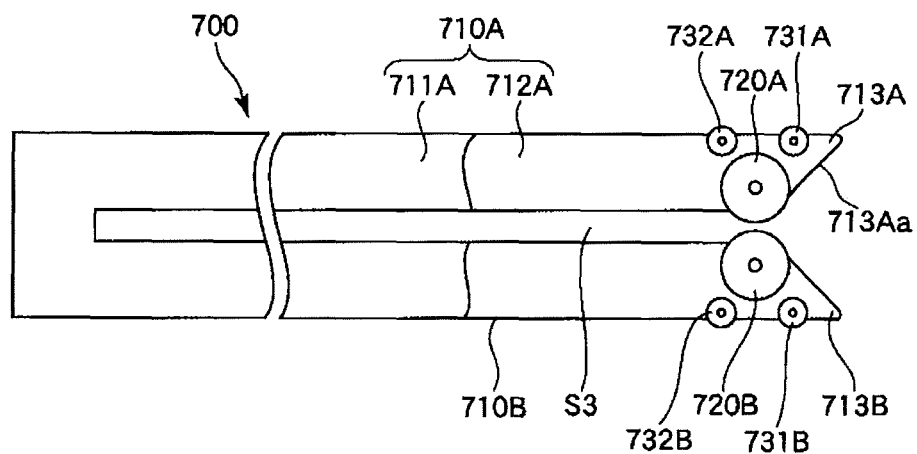
FIG. 65 is a lateral view of a cutting device possessed by a blood vessel dissecting device according to a seventeenth embodiment of the present disclosure.
Figure 66:
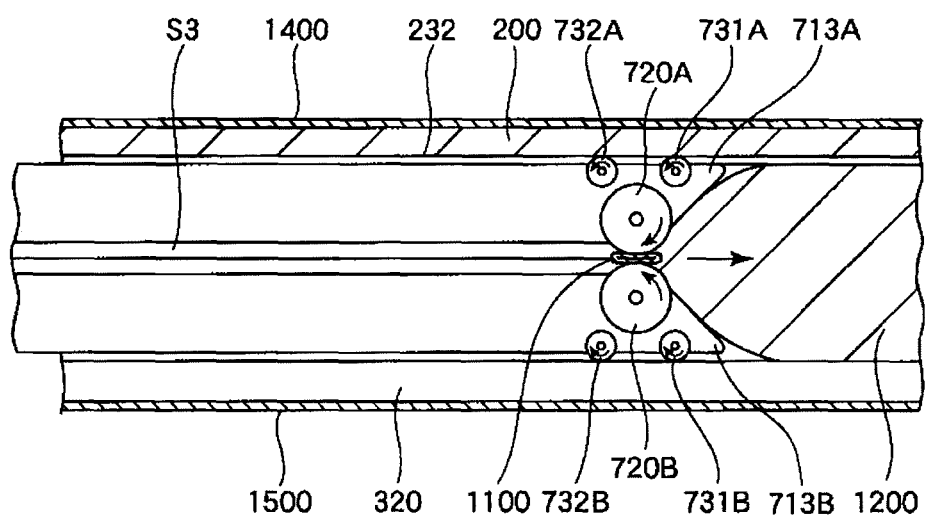
FIG. 66 illustrates a branch vessel treating method.

FIG. 65 is a lateral view of a cutting device possessed by a blood vessel dissecting device according to a seventeenth embodiment of the present disclosure. FIG. 66 illustrates a branch vessel treating method.

In describing the seventeenth embodiment below referring to these figures, differences from the aforementioned embodiments will be described primarily, and descriptions of the same items as above will be omitted.

This embodiment is the same as the aforementioned thirteenth embodiment except mainly for differences in the configurations of the fascia-side dissecting device and the cutting device.

A first dissecting device 310 in this embodiment has a configuration obtained by omitting the electrode 340 from the configuration in the aforementioned thirteenth embodiment described. Similarly, a second dissecting device 320 in this embodiment has a configuration obtained by omitting the electrode 350 from the configuration in the aforementioned thirteenth embodiment.

As depicted in FIG. 65, a cutting device 700 in this embodiment can include a pair of main body sections 710A and 710B disposed to face each other, a roller electrode (first electrode) 720A and rollers 731A and 732A provided on the main body section (first main body section) 710A, and a roller electrode (second electrode) 720B and rollers 731B and 732B provided on the main body section (second main body section) 710B. The main body sections 710A and 710B are disposed to face each other, with a space S3 therebetween, and are interlocked by a proximal portion. The space S3 is a space for guiding branch vessels 1100 and fat 1200 when the cutting device 700 is inserted into a living body.

The main body section 710A is elongated plate-like in shape. In addition, the main body section 710A has a configuration wherein the roller electrode 720A and the rollers 731A and 732A are clamped by two plate-shaped pieces 711A and 712A from both sides. In addition, the main body section 710A is provided at its distal portion with a tapered guide portion 713A. The guide portion 713A has a guide surface 713Aa inclined to face downward, and has a function of guiding the fat 1200 and the branch vessels 1100 into the space S3 when the main body section 710A advances in the living body. Note that the main body section 710B is configured in symmetry with the main body section 710A, with the space S3 therebetween.

The roller electrodes 720A and 720B are disposed to face each other, and are both provided to project into the space S3. Such roller electrodes 720A and 720B are electrodes for cauterizing the branch vessels 1100 and the fat 1200 guided to between the main body sections 710A and 710B by the guide portions 713A and 713B by applying an electric field, and function also as cutting sections for cutting the cauterized branch vessels 1100 and fat 1200.

The rollers 731A and 732A are provided to project to the upper side of the main body section 710A. Similarly, the rollers 731B and 732B are provided to project to the lower side of the main body section 710B. When the main body sections 710 are inserted into the living body, the rollers 731A and 732A engage with rails 231 and 232 of a skin-side dissecting device 200, and the rollers 731B and 732B are rotated along a fascia-side dissecting device 300, whereby the cutting device 700 can be smoothly inserted into the living body.

In such a configuration, in a state in which the skin-side dissecting device 200 and the fascia-side dissecting device 300 are disposed in the living body, the cutting device 700 is inserted between the skin-side dissecting device 200 and the second dissecting device 320 while impressing a high-frequency alternating voltage between the roller electrodes 720A and 720B. As a result, the branch vessels 1100 and the fat 1200 are guided into the space S3 (between the main body sections 710A and 710B) by the guide portions 713A and 713B, and are cauterized and cut when passing between the roller electrodes 720A and 720B, as depicted in FIG. 66. According to such a configuration, the fat 1200 on the upper and lower sides is compressed in the manner of being concentrated into a central area; therefore, the branch vessels 1100 and the fat 1200 can be guided into the space S3 more smoothly as compared to the case where the fat 1200 on the upper and lower sides is compressed in the manner of being concentrated to the lower side, as in the aforementioned thirteenth embodiment, for example.

The same operation is conducted also on the opposite side (the first dissecting device 310 side), whereby the fat 1200 surrounding a great saphenous vein 1000 is dissected over the entire circumference thereof, and the great saphenous vein 1000 is dissected in the state of being covered with the surrounding fat 1200.

By the seventeenth embodiment as above, also, the branch vessels 1100 and fat 1200 present on the left and right sides of the great saphenous vein 1000 can be easily treated.

Note that the space S3 may not necessarily be provided if the branch vessels 1100 and the fat 1200 can be reliably cut reliably without the space S3.

Figure 67:
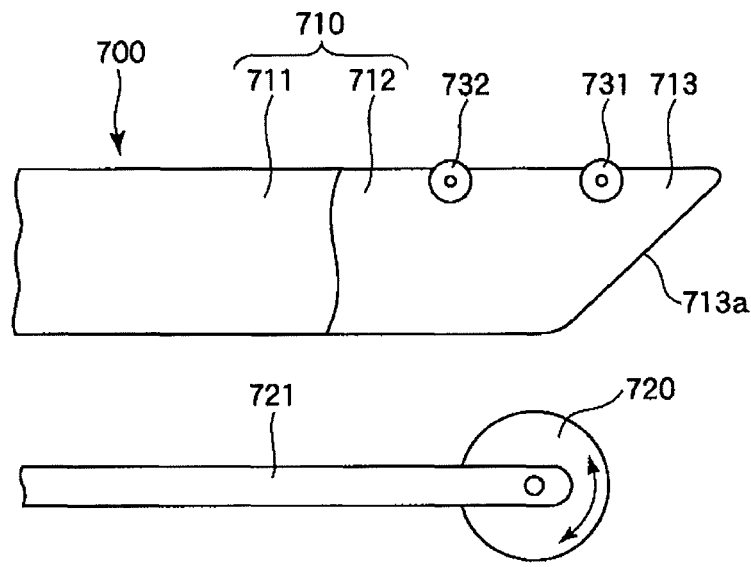
FIG. 67 is a lateral view of a cutting device possessed by a blood vessel dissecting device according to an eighteenth embodiment of the present disclosure.
Figure 68:
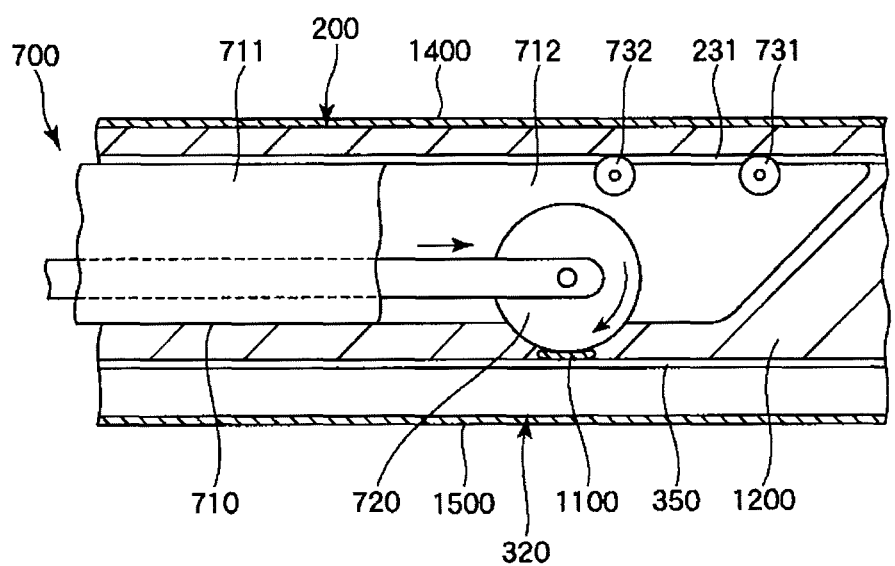
FIG. 68 illustrates a branch vessel treating method.

FIG. 67 is a lateral view of a cutting device possessed by a blood vessel dissecting device according to an eighteenth embodiment of the present disclosure. FIG. 68 illustrates a branch vessel treating method.

In describing the eighteenth embodiment below referring to these figures, differences from the aforementioned embodiments will be described primarily, and descriptions of the same items as above will be omitted.

This embodiment is the same as the aforementioned thirteenth embodiment except mainly for a difference in the configuration of the cutting device.

As depicted in FIG. 67, a cutting device 700 in this embodiment can include a main body section 710 and a roller electrode 720 as separate bodies. In addition, the roller electrode 720 is rotatably supported by an elongated operation section 721. Such a roller electrode 720 is movable on the inside (in a gap between plate-shaped pieces 711 and 712) of a main body section 710.

In such a configuration, first, the main body section 710 is inserted in a living body. Next, as illustrated in FIG. 68, the roller electrode 720 is advanced in the inside of the main body section 710 while being pressed against branch vessels 1100 and fat 1200 and while impressing a high-frequency alternating voltage between the roller electrode 720 and an electrode 350. By this, the branch vessels 1100 and the fat 1200 can be cauterized and cut.

By the eighteenth embodiment as above, also, the branch vessels 1100 and fat 1200 present on the left and right sides of the great saphenous vein 1000 can be treated easily.

Figure 69:
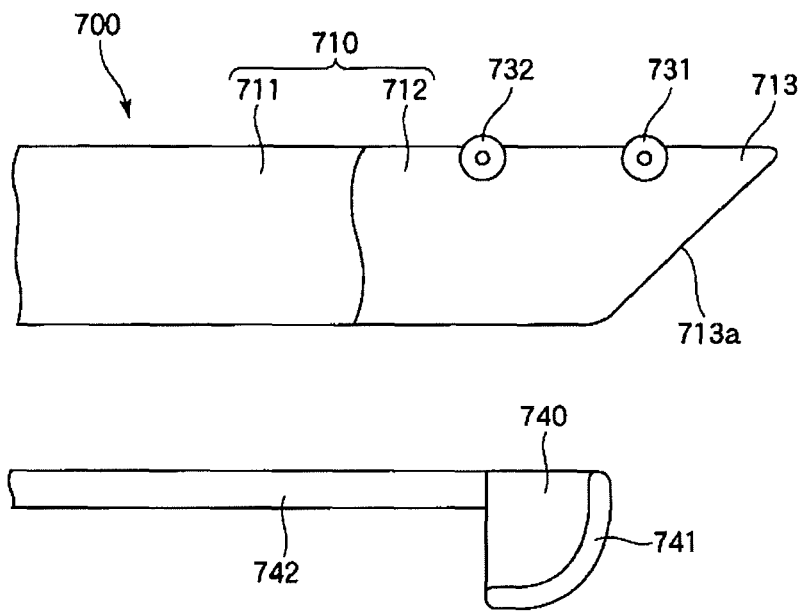
FIG. 69 is a lateral view of a cutting device possessed by a blood vessel dissecting device according to a nineteenth embodiment of the present disclosure.
Figure 70:
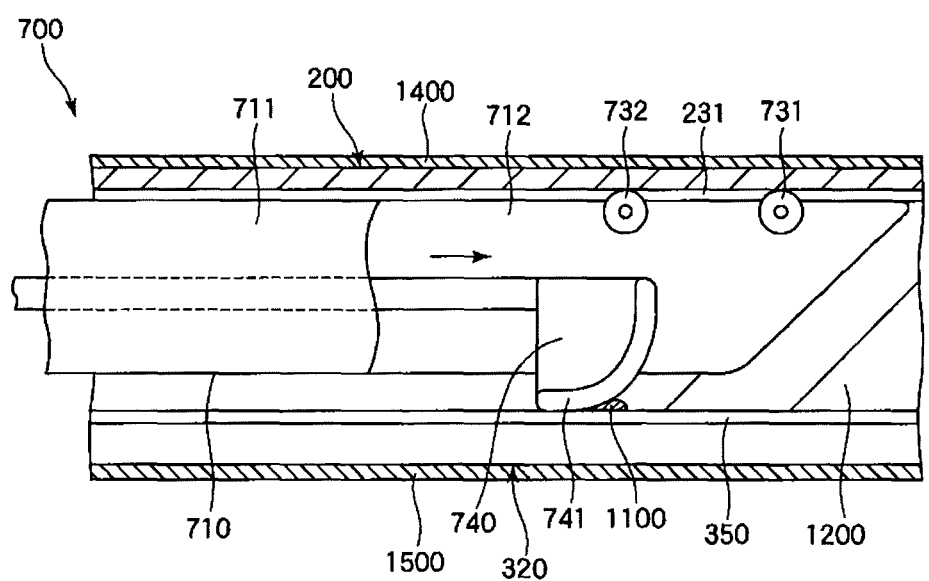
FIG. 70 illustrates a branch vessel treating method.

FIG. 69 is a lateral view of a cutting device possessed by a blood vessel dissecting device according to a nineteenth embodiment of the present disclosure. FIG. 70 illustrates a branch vessel treating method.

In describing the nineteenth embodiment below referring to these figures, differences from the aforementioned embodiments will be described primarily, and descriptions of the same items as above will be omitted.

This embodiment is the same as the aforementioned eighteenth embodiment except mainly for a difference in the configuration of the cutting device.

A cutting device 700 in this embodiment has an electrode 740 having a cutting edge portion 741 in place of the roller electrode 720 in the aforementioned eighteenth embodiment. The electrode 740 is fixed to a distal portion of an elongated operation section 742. Such an electrode 740 is movable on the inside (in a gap between plate-shaped pieces 711 and 712) of a main body section 710.

In such a configuration, first, the main body section 710 is inserted in a living body. Next, as depicted in FIG. 70, the electrode 740 is advanced in the inside of the main body section 710 while being pressed against branch vessels 1100 and fat 1200 and while impressing a high-frequency alternating voltage between the electrode 740 and an electrode 350. By this, the branch vessels 1100 and the fat 1200 can be cauterized and cut.

According to the nineteenth embodiment as above, also, the branch vessels 1100 and fat 1200 present on the left and right sides of the great saphenous vein 1000 can be easily treated.

Note that in the roller electrode 720, an insulating coating or the like may be applied to roller side surface portions such that only a roller end surface portion (circumferential portion) serves as an electrode. In addition, only a part near the cutting edge portion of the electrode 740 having the cutting edge portion 741 may serve as an electrode. In that case, a current passing part is limited, so that thermal coagulation can be performed more efficiently.

While the blood vessel dissecting device and the blood vessel dissecting method according to the present disclosure have been described above based on the embodiments illustrated in the drawings, the present disclosure is not limited to the embodiments. The configuration of each component may be replaced by an arbitrary configuration that has the same or equivalent function to the original. In addition, other arbitrary structure or component may be added to those in the present disclosure. In addition, the embodiments may be combined as required.

In addition, while the great saphenous vein is dissected in the state in which its circumference is entirely covered with fat in the aforementioned embodiments, this is not restrictive. Specifically, the great saphenous vein may be dissected in the state in which part of its circumference is covered with fat, or may be dissected in the state of being not covered with fat. For example, the great saphenous vein upon dissection may be covered with flat-shaped fat wherein the fat is thin on the upper and lower sides (or the fat 1200 is absent on the upper and lower sides) and the fat is thick on the left and right sides. In such a condition, the state (for example, the presence/absence of damage, shape, torsion, etc.) of the great saphenous vein can be easily confirmed from the upper and lower sides. Therefore, the great saphenous vein can be appropriately used as a bypass vessel or the like after confirming the state thereof.

Figure 71:
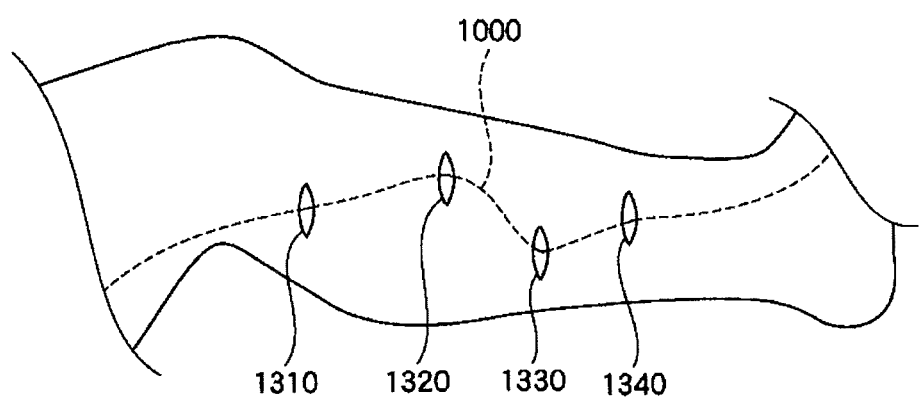
FIG. 71 illustrates a blood vessel dissecting method.

In addition, in the case where the great saphenous vein 1000 is largely tortuous as depicted in FIG. 71, for example, the great saphenous vein 1000 may be dissected by incising it on the basis of each of comparatively rectilinearly extending portions of the great saphenous vein 1000 and repeating the above-mentioned operation multiple times. Referring to FIG. 71, a method may be adopted wherein, first, the great saphenous vein 1000 is dissected between incisions 1310 and 1320, next the great saphenous vein 1000 is dissected between the incisions 1320 and 1330, and thereafter the great saphenous vein 1000 is dissected between the incisions 1330 and 1340. Then, it is sufficient that the great saphenous vein 1000 is ligated through the incisions 1310 and 1340, and extracted through either of the incisions 1310 and 1340. By this, the great saphenous vein 1000 with a larger length (predetermined length) can be harvested, independently of the state of the great saphenous vein 1000.

In addition, while the case of harvesting a bypass vessel in performing blood vessel bypass grafting has been described in the aforementioned embodiments, the use of the harvested blood vessel is not limited to a bypass vessel.

According to an aspect of the present disclosure, there is provided a blood vessel dissecting device including at least two dissecting devices which are inserted into a living body along a blood vessel to dissect tissue in a direction of alignment thereof with the blood vessel, wherein the at least two dissecting devices include a first dissecting device and a second dissecting device, and the first dissecting device and the second dissecting device are disposed juxtaposedly in the living body, and a branch vessel branched from the blood vessel is located between the first dissecting device and the second dissecting device. According to such a configuration, when a treating device for treating branch vessels is inserted while guiding it by the first and second dissecting devices, for example, it is possible to easily treat the branch vessels by the treating device. Therefore, a blood vessel dissecting device excellent in workability in blood vessel dissection can be realized.

According to another aspect of the present disclosure, there is provided a blood vessel dissecting method including: a step of inserting at least two dissecting devices into a living body along a blood vessel and disposing a branch vessel branched from the blood vessel between the two dissecting devices; and a step of inserting a treating device for treating the branch vessel between the two dissecting devices and treating the branch vessel. According to such a method, branch vessels can be treated easily.

Accordingly, the blood vessel dissecting device disclosed herein is industrially applicable.

The detailed description above describes a blood vessel dissecting device. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A blood vessel dissecting device comprising:
a fascia-side dissecting device configured to be inserted into a living body along a blood vessel, the fascia-side dissecting device configured to dissect tissue in a direction of alignment with the blood vessel;
a cutting device configured to be inserted into the living body along the blood vessel and to be individually inserted with the fascia-side dissecting device and configured to cut tissue surrounding the blood vessel in the direction of alignment with the blood vessel, and wherein the fascia-side dissecting device and the cutting device are configured to be slidably attached and detached from one another;
a skin-side dissecting device configured to be inserted into a living body and to be individually inserted with the fascia-side dissecting device, the skin-side dissecting device comprising a rail in axial direction;
the cutting device being located between the fascia-side dissecting device and the skin-side dissecting device;
the cutting device including a main body section and a movable cutting section, the main body section configured to be inserted into the living body and to hold the tissue between the cutting device and the fascia-side dissecting device, and the main body section including a groove and a connection section extending in an axial direction, the connection section configured to be connect with the rail and to be insert along the skin-side dissecting device, the groove being open on a side of the main body section facing the fascia-side dissecting device, and wherein the groove includes an opening on a proximal end of the main body section and a distal-most end of the groove in the axial direction is closed on a distal portion of the main body section, the opening on the proximal end of the main body section forming an insertion hole configured to receive the movable cutting section; and
wherein the movable cutting section is configured to cut the tissue held between the main body section and the fascia-side dissecting device.

2. The blood vessel dissecting device according to claim 1, wherein the main body section has a guide section on a distal end of the main body section, the guide section configured to guide the tissue to between the main body section and the fascia-side dissecting device.

3. The blood vessel dissecting device according to claim 2, wherein the guide section has an inclined guide surface, which faces toward the fascia-side dissecting device.

4. The blood vessel dissecting device according to claim 1,
wherein the tissue is configured to be held between the main body section and the fascia-side dissecting device is configured to receive a branch vessel branched from the blood vessel, and
the cutting device is configured to cut the branch vessel.

5. The blood vessel dissecting device according to claim 4, further comprising a first electrode and a second electrode which apply an electric field to the branch vessel.

6. The blood vessel dissecting device according to claim 5, wherein the first electrode and the second electrode are both provided in the cutting device.

7. The blood vessel dissecting device according to claim 6, wherein the movable cutting section functions also as the second electrode.

8. The blood vessel dissecting device according to claim 5,
wherein the first electrode is provided in the cutting device, and
the second electrode is provided in the fascia-side dissecting device.

9. The blood vessel dissecting device according to claim 1, wherein the fascia-side dissecting device comprises:
a first dissecting device and a second dissecting device, the first dissecting device and the second dissecting device are configured to be disposed juxtaposedly in the living body, and a branch vessel branched from the blood vessel is configured to be located between the first dissecting device and the second dissecting device.

10. The blood vessel dissecting device according to claim 9, wherein the branch vessel is configured to be held between the first dissecting device and the second dissecting device.

11. The blood vessel dissecting device according to claim 1, wherein the main body section has an elongated plate-like shape, and a protection section provided an a side opposite the side facing the fascia-side dissecting device, the protection section extending in an axial direction of the main body section and a peripheral surface of the protection section is rounded.

12. The blood vessel dissecting device according to claim 1, wherein the main body section has connection sections configured to be connected with rails of a skin-side dissecting device.

13. A blood vessel dissecting device comprising:
a fascia-side dissecting device configured to be inserted into a living body along a blood vessel, the fascia-side dissecting device configured to dissect tissue in a direction of alignment with the blood vessel,
wherein the fascia-side dissecting device comprises:
a first dissecting device and a second dissecting device, the first dissecting device and the second dissecting device are configured to be disposed juxtaposedly in the living body and to receive a branch vessel branched from the blood vessel between the first dissecting device and the second dissecting device, and
wherein the fascia-side dissecting device comprises a cavity section between the first dissecting device and the second dissecting device;
a cutting device configured to be inserted into the living body along the blood vessel and to be individually inserted with the fascia-side dissecting device, and wherein the fascia-side dissecting device and the cutting device are configured to be slidably attached and detached from one another, the cutting device configured to cut tissue surrounding the blood vessel in the direction of alignment with the blood vessel, wherein the cutting device includes a main body section and a movable first cutting section, the main body section configured to be inserted into the living body and to hold the tissue between the cutting device and the fascia-side dissecting device, and the main body section including a groove extending in an axial direction, the groove being open on a side of the main body section facing the fascia-side dissecting device, and wherein the groove includes an opening on a proximal end of the main body section and a distal-most end of the groove in the axial direction is closed on a distal portion of the main body section, the opening on the proximal end of the main body section forming an insertion hole configured to receive the movable first cutting section, and the movable first cutting section is configured to cut the tissue held between the main body section and the fascia-side dissecting device; and a treating device configured to be inserted into the cavity section of the fascia-side dissecting device, the treating device includes a bar-shaped elongated operation section, an electrode provided at a proximal portion of the operation section, and a second cutting section provided at a proximal portion of the electrode, wherein the first cutting section is different from the second cutting section, a cross-sectional shape of the first cutting section is orthogonal of a cross-sectional shape of the second cutting section.

14. The blood vessel dissecting device according to claim 13, wherein the main body section has a guide section on a distal end of the main body section configured to guide the tissue to between the main body section and the fascia-side dissecting device.

15. The blood vessel dissecting device according to claim 13, wherein the tissue is configured to be held between the main body section and the fascia-side dissecting device is configured to receive a branch vessel branched from the blood vessel, and the cutting device is configured to cut the branch vessel; and a first electrode and a second electrode configured to apply an electric field to the branch vessel, wherein the first electrode and the second electrode are both provided in the cutting device.

16. A blood vessel dissecting method comprising:

inserting a fascia-side dissecting device into a living body along a blood vessel, the fascia-side dissecting device configured to dissect tissue in a direction of alignment with the blood vessel;

inserting a cutting device into the living body along the blood vessel after the inserting the fascia-side dissecting device into a living body along a blood vessel, and wherein the fascia-side dissecting device and the cutting device are configured to be slidably attached and detached from one another, the cutting device configured to cut tissue surrounding the blood vessel in the direction of alignment with the blood vessel, wherein the cutting device includes a main body section and a movable cutting section, the main body section configured to be inserted into the living body and to hold the tissue between the cutting device and the fascia-side dissecting devicel;

providing the main body section of the cutting device with a groove extending in an axial direction, the groove being open on a side of the main body section facing the fascia-side dissecting device, and wherein the groove includes an opening on a proximal end of the main body section and a distal-most end of the groove in the axial direction is closed on a distal portion of the main body section, the opening on the proximal end of the main body section forming an insertion hole configured to receive the movable cutting section;

inserting the movable cutting section into the insertion hole on the proximal end of the main body section of the cutting device; and cutting the tissue being held between the main body section and the fascia-side dissecting device with the movable cutting section of the cutting device.

17. The blood vessel dissecting method according to claim 16, comprising:

guiding the tissue to between the main body section and the fascia-side dissecting device with a guide section on a distal end of the main body section.

18. The blood vessel dissecting method according to claim 16, comprising:

holding the tissue between the main body section and the fascia-side dissecting device with a branch vessel branched from the blood vessel, and cutting the branch vessel with the movable cutting device.

19. The blood vessel dissecting method according to claim 18, comprising:

applying an electric field to the branch vessel with a first electrode and a second electrode.

20. The blood vessel dissecting method according to claim 19, comprising:

providing both the first electrode and the second electrode in the cutting device.

* * * * *